United States Patent
Zolotukhin et al.

(10) Patent No.: US 12,188,037 B2
(45) Date of Patent: Jan. 7, 2025

(54) SYNTHETIC COMBINATORIAL AAV3 CAPSID LIBRARY

(71) Applicant: University of Florida Research Foundation, Incorporated, Gainesville, FL (US)

(72) Inventors: Sergei Zolotukhin, Gainesville, FL (US); Damien Marsic, Rockville, MD (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1194 days.

(21) Appl. No.: 15/769,615

(22) PCT Filed: Oct. 21, 2016

(86) PCT No.: PCT/US2016/058130
§ 371 (c)(1),
(2) Date: Apr. 19, 2018

(87) PCT Pub. No.: WO2017/070476
PCT Pub. Date: Apr. 27, 2017

(65) Prior Publication Data
US 2020/0181644 A1 Jun. 11, 2020

Related U.S. Application Data

(60) Provisional application No. 62/245,025, filed on Oct. 22, 2015.

(51) Int. Cl.
| | |
|---|---|
| *C12N 15/86* | (2006.01) |
| *C07K 14/005* | (2006.01) |
| *C12N 7/00* | (2006.01) |
| *C40B 40/08* | (2006.01) |

(52) U.S. Cl.
CPC ............ *C12N 15/86* (2013.01); *C07K 14/005* (2013.01); *C12N 7/00* (2013.01); *C40B 40/08* (2013.01); *C12N 2750/14122* (2013.01); *C12N 2750/14143* (2013.01); *C12N 2810/6027* (2013.01)

(58) Field of Classification Search
CPC ............... C12N 15/86; C12N 7/00; C12N 2750/14122; C12N 2750/14143; C12N 2810/6027; C07K 14/005; C40B 40/08
See application file for complete search history.

(56) References Cited

U.S. PATENT DOCUMENTS

| | | | |
|---|---|---|---|
| 6,156,303 A | 12/2000 | Russell et al. | |
| 7,186,552 B2 | 3/2007 | Wilson et al. | |
| 7,220,577 B2 | 5/2007 | Zolotukhin | |
| 7,927,585 B2 | 4/2011 | Snyder | |
| 8,445,267 B2 | 5/2013 | Zhong et al. | |
| 9,157,098 B2 | 10/2015 | Zhong et al. | |
| 9,677,088 B2 | 6/2017 | Nakai et al. | |
| 9,725,485 B2 | 8/2017 | Srivastava et al. | |
| 9,775,918 B2 * | 10/2017 | Zhong | A61K 35/76 |
| 10,011,640 B2 | 7/2018 | Srivastava et al. | |
| 10,308,957 B2 | 6/2019 | Boye et al. | |
| 10,426,844 B2 | 10/2019 | Agbandje-McKenna et al. | |
| 10,648,000 B2 | 5/2020 | Hauswirth et al. | |
| 10,723,768 B2 * | 7/2020 | Zhong | C12N 7/00 |
| 10,793,606 B2 | 10/2020 | Zolotukhin et al. | |
| 10,815,279 B2 | 10/2020 | Srivastava et al. | |
| 2006/0188484 A1 | 8/2006 | Rabinowitz et al. | |
| 2007/0036760 A1 * | 2/2007 | Wilson | A61K 48/00 435/235.1 |
| 2008/0269149 A1 | 10/2008 | Bowles et al. | |
| 2009/0075357 A1 | 3/2009 | Snyder | |
| 2009/0197338 A1 * | 8/2009 | Vandenberghe | A61K 48/0091 435/471 |
| 2010/0104561 A1 | 4/2010 | Zhong et al. | |
| 2013/0109742 A1 | 5/2013 | Hewitt et al. | |
| 2014/0341852 A1 | 11/2014 | Srivastava et al. | |
| 2016/0017005 A1 | 1/2016 | Asokan et al. | |
| 2016/0369298 A1 | 3/2016 | Marsic et al. | |
| 2016/0289275 A1 | 10/2016 | Chiorini et al. | |
| 2018/0066285 A1 | 3/2018 | Ojala et al. | |
| 2018/0193489 A1 | 7/2018 | Hobbs et al. | |

(Continued)

FOREIGN PATENT DOCUMENTS

| | | |
|---|---|---|
| EP | 1 487 501 B1 | 12/2012 |
| JP | 2008-523813 A | 7/2008 |

(Continued)

OTHER PUBLICATIONS

Zinn et al. "In silico reconstruction of the viral evolutionary lineage yields a potent gene therapy vector." Cell reports 12.6 (2015): 1056-1068 (Year: 2015).*

(Continued)

*Primary Examiner* — Jeremy C Flinders
*Assistant Examiner* — Alexander W Nicol
(74) *Attorney, Agent, or Firm* — Wolf, Greenfield & Sacks, P.C.

(57) ABSTRACT

Compositions and methods for producing modified AAV Cap genes and combinatorial libraries of chimeric AAV vectors and virions in an AAV serotype 3 background. Selecting for modified AAV3 virions displaying cell- or tissue-specific tropisms differing from WT AAV3. Using the synthetic combinatorial AAV3 capsid libraries for introducing into a selected target host cells one or more nucleic acid molecules useful in diagnostic and/or therapeutic gene-therapy regimens.

4 Claims, 9 Drawing Sheets
Specification includes a Sequence Listing.

(56) References Cited

U.S. PATENT DOCUMENTS

| | | | |
|---|---|---|---|
| 2018/0244727 | A1 | 8/2018 | Zhong et al. |
| 2018/0245098 | A1 | 8/2018 | Yazicioglu et al. |
| 2019/0048041 | A1 | 2/2019 | Asokan et al. |
| 2019/0127424 | A1 | 5/2019 | Srivastava et al. |
| 2019/0249195 | A1 | 8/2019 | Marsic et al. |
| 2020/0002386 | A1 | 1/2020 | Zolotukhin et al. |
| 2021/0040156 | A1* | 2/2021 | Zhong .......... C07K 14/005 |
| 2021/0061863 | A1 | 3/2021 | Zolotukhin et al. |
| 2021/0253644 | A1* | 8/2021 | Srivastava .......... A61K 48/005 |
| 2023/0049066 | A1 | 2/2023 | Zolotukhin et al. |

FOREIGN PATENT DOCUMENTS

| | | | | |
|---|---|---|---|---|
| WO | WO 2004/112727 | A2 | 12/2004 | |
| WO | WO 2005/033321 | A2 | 4/2005 | |
| WO | WO 2008/124724 | A1 | 10/2008 | |
| WO | WO 2010/011404 | A2 | 1/2010 | |
| WO | WO 2012/057363 | A1 | 5/2012 | |
| WO | WO 2012/109570 | A1 | 8/2012 | |
| WO | WO 2013/170078 | A1 | 11/2013 | |
| WO | WO 2014/193716 | A2 | 12/2014 | |
| WO | WO-2015048534 | A1 * | 4/2015 | .......... C07K 14/005 |
| WO | WO 2015/108610 | A1 | 7/2015 | |
| WO | WO 2015/121501 | A1 | 8/2015 | |
| WO | WO 2015/134643 | A1 | 9/2015 | |
| WO | WO 2017/070476 | A2 | 4/2017 | |
| WO | WO 2018/200419 | A1 | 11/2018 | |

OTHER PUBLICATIONS

Invitation to Pay Additional Fees for Application No. PCT/US2020/062114, mailed Mar. 8, 2021.
International Search Report and Written Opinion for Application No. PCT/US2020/062114, mailed Apr. 29, 2021.
Invitation to Pay Additional Fees for Application No. PCT/US2020/062113, mailed Feb. 17, 2021.
International Search Report and Written Opinion for Application No. PCT/US2020/062113, mailed Apr. 21, 2021.
Chen, Adeno-associated virus vectors for human gene therapy. World Journal of Medical Genetics. Aug. 27, 2015;5(3):28-45.
International Search Report and Written Opinion for International Application No. PCT/US2016/058130 mailed Apr. 7, 2017.
International Preliminary Report on Patentability for International Application No. PCT/US2016/058130 mailed May 3, 2018.
Appleyard et al., Pretreatment with the probiotic VSL#3 delays transition from inflammation to dysplasia in a rat model of colitis-associated cancer. Am J Physiol Gastrointest Liver Physiol. Dec. 2011;301(6):G1004-13. doi: 10.1152/ajpgi.00167.2011. Epub Sep. 8, 2011.
Bowles et al., Phase 1 gene therapy for Duchenne muscular dystrophy using a translational optimized AAV vector. Mol Ther. Feb. 2012;20(2):443-55. doi: 10.1038/mt.2011.237. Epub Nov. 8, 2011.
Bozzetti et al., Metabolic Bone Disease in preterm newborn: an update on nutritional issues. Ital J Pediatr. Jul. 14, 2009;35(1):20. doi: 10.1186/1824-7288-35-20.
Galindo, Alkaline Phosphatase (ALP). Aug. 2, 20103. Retrieved on May 8, 2018. http://www2.isu.edu/~galisusa/alp_sop.html. 4 pages.
Gao et al., Clades of Adeno-associated viruses are widely disseminated in human tissues. J Virol. Jun. 2004;78(12):6381-8.
Lan et al., IA-2, a transmembrane protein of the protein tyrosine phosphatase family, is a major autoantigen in insulin-dependent diabetes mellitus. Proc Natl Acad Sci U S A. Jun. 25, 1996;93(13):6367-70.
Lerch et al., The structure of adeno-associated virus serotype 3B (AAV-3B): insights into receptor binding and immune evasion. Virology. Jul. 20, 2010;403(1):26-36. doi: 10.1016/j.virol.2010.03.027. Epub May 4, 2010.
Lochrie et al., Mutations on the external surfaces of adeno-associated virus type 2 capsids that affect transduction and neutralization. J Virol. Jan. 2006;80(2):821-34.

Marsic et al., Vector design Tour de Force: integrating combinatorial and rational approaches to derive novel adeno-associated virus variants. Mol Ther. Nov. 2014;22(11):1900-9. doi: 10.1038/mt.2014.139. Epub Jul. 22, 2014.
Muramatsu et al., Nucleotide sequencing and generation of an infectious clone of adeno-associated virus 3. Virology. Jul. 1, 1996;221(1):208-17.
International Preliminary Report on Patentability for Application No. PCT/US2020/062114, mailed Jun. 9, 2022.
International Preliminary Report on Patentability for Application No. PCT/US2020/062113, mailed Jun. 9, 2022.
Ito et al., Engineered adeno-associated virus 3 vector with reduced reactivity to serum antibodies. Sci Rep. Apr. 29, 2021;11(1):9322. doi: 10.1038/s41598-021-88614-9.
Aslanidi et al., High-efficiency transduction of human monocyte-derived dendritic cells by capsid-modified recombinant AAV2 vectors. Vaccine. Jun. 6, 2012;30(26):3908-17. doi: 10.1016/j.vaccine.2012.03.079. Epub Apr. 10, 2012.
Aslanidi et al., Optimization of the capsid of recombinant adeno-associated virus 2 (AAV2) vectors: the final threshold? PLoS One. 2013;8(3):e59142. doi: 10.1371/journal.pone.0059142. Epub Mar. 19, 2013.
Choudhury et al., Novel Methodology for Creating Macaque Retinas with Sortable Photoreceptors and Ganglion Cells. Front Neurosci. Dec. 1, 2016;10:551. eCollection 2016.
Gao et al., Clades of Adeno-associated viruses are widely disseminated in human tissues. J Virol. Jun. 2004;78(12):6381-8. Novel adeno-associated viruses from rhesus monkeys as vectors for human gene therapy. Proc Natl Acad Sci U S A. Sep. 3, 2002;99(18):11854-9. Epub Aug. 21, 2002.
Genbank Submission; NIH/NCBI, Accesion No. AAS99272.1. Gao et al., Jun. 24, 2004.
Grimm et al., E Pluribus Unum: 50 Years of Research, Millions of Viruses, and One Goal Tailored Acceleration of AAV Evolution. Mol Ther. Dec. 2015;23(12):1819-31.
Guo et al., Protein tolerance to random amino acid change. PNAS. Jun. 22, 2004;101(25):9205-10.
Gurda et al., Capsid antibodies to different adeno-associated virus serotypes bind common regions. J Virol. Aug. 2013;87(16):9111-24. doi: 10.1128/JVI.00622-13. Epub Jun. 12, 2013.
Klimczak, Molecular evolution of adeno-associated virus for improved retinal gene therapies. University of California, Berkeley. Jan. 1, 2010. Retrieved from the internet <https://digitalassets.lib.berkeley.edu/etd/ucb/text/Klimczak_berkeley_0028E_10444.pdf> 116 pages.
Koerber et al., DNA shuffling of adeno-associated virus yields functionally diverse viral progeny. Mol Ther. Oct. 2008;16(10):1703-9. doi: 10.1038/mt.2008.167. Epub Aug. 26, 2008.
Maersch et al., Optimization of stealth adeno-associated virus vectors by randomization of immunogenic epitopes. Virology. Feb. 5, 2010;397(1):167-75. doi: 10.1016/j.virol.2009.10.021. Epub Nov. 18, 2009.
Maguire et al., Directed evolution of adeno-associated virus for glioma cell transduction. J Neurooncol. Feb. 2010;96(3):337-47. doi: 10.1007/s11060-009-9972-7. Epub Jul. 19, 2009.
Maheshri et al., Directed evolution of adeno-associated virus yields enhanced gene delivery vectors. Nat Biotechnol. Feb. 2006;24(2):198-204. doi: 10.1038/nbt1182. Epub Jan. 22, 2006.
Opie et al., Identification of amino acid residues in the capsid proteins of adeno-associated virus type 2 that contribute to heparan sulfate proteoglycan binding. J Virol. Jun. 2003;77(12):6995-7006.
Ozawa, [Gene therapy using AAV]. Uirusu. Jun. 2007;57(1):47-55. Article in Japanese.
Pang et al., AAV-mediated cone rescue in a naturally occurring mouse model of CNGA3-achromatopsia. PLoS One. 2012;7(4):e35250. doi: 10.1371/journal.pone.0035250. Epub Apr. 11, 2012.
Perabo et al., Combinatorial engineering of a gene therapy vector: directed evolution of adeno-associated virus. J Gene Med. Feb. 2006;8(2):155-62.
Romero et al., Exploring protein fitness landscapes by directed evolution. Nat Rev Mol Cell Biol. Dec. 2009; 10(12):866-76.
Shannon et al., ID of Optimal Gene Delivery Vectors in Primate Retina for Treatment of Human Disorders: Labels Non-Human Primate Eyes with Fluorescent Proteins and/or Fluorescent Dyes,

(56) References Cited

OTHER PUBLICATIONS

Creating Sortable Cell Populations, Allowing for Screening of Capsid and Promoter Libraries. Office of Technology Licensing, University of Florida. Feb. 11, 2017. Retrieved from the Internet: <http://technologylicensing.research.ufl.edu/technologies/16134.pdf> on Apr. 12, 2017. 4 pages.

Tseng et al., Mapping the AAV Capsid Host Antibody Response toward the Development of Second Generation Gene Delivery Vectors. Front Immunol. Jan. 30, 2014;5:9. doi: 10.3389/fimmu.2014.00009. eCollection 2014.

Wu et al., Mutational analysis of the adeno-associated virus type 2 (AAV2) capsid gene and construction of AAV2 vectors with altered tropism. J Virol. Sep. 2000;74(18):8635-47. doi: 10.1128/jvi.74.

Xie et al., The atomic structure of adeno-associated virus (AAV-2), a vector for human gene therapy. Proc Natl Acad Sci U S A. Aug. 6, 2002;99(16):10405-10. doi: 10.1073/pnas.162250899. Epub Jul. 22, 2002.

Zhong et al., Next generation of adeno-associated virus 2 vectors: point mutations in tyrosines lead to high-efficiency transduction at lower doses. Proc Natl Acad Sci U S A. Jun. 3, 2008;105(22):7827-32. doi: 10.1073/pnas.0802866105. Epub May 29, 2008. Erratum in Proc Natl Acad Sci U S A. Aug. 5, 2008;105(31):11032.

Zolotukhin et al., Improved Adeno-associated Viral Gene Transfer to Murine Glioma. J Genet Syndr Gene Ther. Apr. 29, 2013;4(133):12815. doi: 10.4172/2157-7412.

U.S. Appl. No. 17/779,505, filed May 24, 2022, Zolotukhin et al.
U.S. Appl. No. 17/779,510, filed May 24, 2022, Zolotukhin et al.
PCT/US2020/062114, Jun. 9, 2022, International Preliminary Report on Patentability.
PCT/US2020/062113, Jun. 9, 2022, International Preliminary Report on Patentability.
U.S. Appl. No. 16/208,127, filed Dec. 3, 2018, Marsic et al.
U.S. Appl. No. 17/009,536, filed Sep. 1, 2020, Zolotukhin et al.

\* cited by examiner

Figure 1A

```
241 T  T  S  T  R  T  W  A  L  P  T  Y  N  N  H  L  Y  K  Q  I
721 ACCACCAGCACCAGAACCTGGGCCCTGCCCACTTACAACAACCATCTCTACAAGCAAATC

261 S  S  Q  S  G  A  S  N  D  N  H  Y  F  G  Y  S  T  P  W  G
781 TCCAGCCAATCAGGAGCTTCAAACGACAACCACTACTTTGGCTACAGCACCCCTTGGGGG
        VVMD        ASC

281 Y  F  D  F  N  R  F  H  C  H  F  S  P  R  D  W  Q  R  L  I
841 TATTTTGACTTTAACAGATTCCACTGCCACTTCTCACCACGTGACTGGCAGCGACTCATT

301 N  N  N  W  G  F  R  P  K  K  L  S  F  K  L  F  N  I  Q  V
901 AACAACAACTGGGGATTCCGGCCCAAGAAACTCAGCTTCAAGCTCTTCAACATCCAAGTT

321 R  G  V  T  Q  N  D  G  T  T  T  I  A  N  N  L  T  S  T  V
961 AGAGGGGTCACGCAGAACGATGGCACGACGACTATTGCCAATAACCTTACCAGCACGGTT

341 Q  V  F  T  D  S  E  Y  Q  L  P  Y  V  L  G  S  A  H  Q  G
1021 CAAGTGTTTACGGACTCGGAGTATCAGCTCCCGTACGTGCTCGGGTCGGCGCACCAAGGC

361 C  L  P  P  F  P  A  D  V  F  M  V  P  Q  Y  G  Y  L  T  L
1081 TGTCTCCCGCCGTTTCCAGCGGACGTCTTCATGGTCCCTCAGTATGGATACCTCACCCTG

381 N  N  G  S  Q  A  V  G  R  S  S  F  Y  C  L  E  Y  F  P  S
1141 AACAACGGAAGTCAAGCGGTGGGACGCTCATCCTTTTACTGCCTGGAGTACTTCCCTTCG

401 Q  M  L  R  T  G  N  N  F  Q  F  S  Y  T  F  E  D  V  P  F
1201 CAGATGCTAAGGACTGGAAATAACTTCCAATTCAGCTATACCTTCGAGGATGTACCTTTT

421 H  S  S  Y  A  H  S  Q  S  L  D  R  L  M  N  P  L  I  D  Q
1261 CACAGCAGCTACGCTCACAGCCAGAGTTTGGATCGCTTGATGAATCCTCTTATTGATCAG

441 Y  L  Y  Y  L  N  R  T  Q  G  T  T  S  G  T  T  N  Q  S  R
1321 TATCTGTACTACCTGAACAGAACGCAAGGAACAACCTCTGGAACAACCAACCAATCACGG
                              RGCAMCVCNRGC    RCCRVCMHSMRSVVS

461 L  L  F  S  Q  A  G  P  Q  S  M  S  L  Q  A  R  N  W  L  P
1381 CTGCTTTTTAGCCAGGCTGGGCCTCAGTCTATGTCTTTGCAGGCCAGAAATTGGCTACCT
       VNG

481 G  P  C  Y  R  Q  Q  R  L  S  K  T  A  N  D  N  N  N  S  N
1441 GGGCCCTGCTACCGGCAACAGAGACTTTCAAGACTGCTAACGACAACAACAACAGTAAC
                                  MARYCBMCRVCSRS              R  S

501 F  P  W  T  A  A  S  K  Y  H  L  N  G  R  D  S  L  V  N  P
1501 TTTCCTTGGACAGCGGCCAGCAAATATCATCTCAATGGCCGCGACTCGCTGGTGAATCCA
              M            M
```

Figure 1B

```
521 G   P   A   M   A   S   H   K   D   D   E   E   K   F   F   P   M   H   G   N
1561 GGACCAGCTATGGCCAGTCACAAGGACGATGAAGAAAAATTTTTCCCTATGCACGGCAAT
                                RR         RMSGRS R

541 L   I   F   G   K   E   G   T   T   A   S   N   A   E   L   D   N   V   M   I
1621 CTAATATTTGGCAAAGAAGGGACAACGGCAAGTAACGCAGAATTAGATAATGTAATGATT
                    S   RRCRSCRVSRV RVCR TRYC MSDWC RSVRS

561 T   D   E   E   E   I   R   T   T   N   P   V   A   T   E   Q   Y   G   T   V
1681 ACGGATGAAGAAGAGATTCGTACCACCAATCCTGTGGCAACAGAGCAGTATGGAACTGTG

581 A   N   N   L   Q   S   S   N   T   A   P   T   T   G   T   V   N   H   Q   G
1741 GCAAATAACTTGCAGAGCTCAAATACAGCTCCCACGACTGGAACTGTCAATCATCAGGGG
                    RVSVVSMRSRVCVVS       DH VVSRNS    VMS

601 A   L   P   G   M   V   W   Q   D   R   D   V   Y   L   Q   G   P   I   W   A
1801 GCCTTACCTGGCATGGTGTGGCAAGATCGTGACGTCTACCTTCAAGGACCTATCTGGGCA

621 K   I   P   H   T   D   G   H   F   H   P   S   P   L   M   G   G   F   G   L
1861 AAGATTCCTCACACGGATGGACACTTTCATCCTTCTCCTCTGATGGGAGGCTTTGGACTG

641 K   H   P   P   P   Q   I   M   I   K   N   T   P   V   P   A   N   P   P   T
1921 AAACATCCGCCTCCTCAAATCATGATCAAAAATACTCCGGTACCGGCAAATCCTCCGACG

661 T   F   S   P   A   K   F   A   S   F   I   T   Q   Y   S   T   G   Q   V   S
1981 ACTTTCAGCCCGGCCAAGTTTGCTTCATTTATCACTCAGTACTCCACTGGACAGGTCAGC

681 V   E   I   E   W   E   L   Q   K   E   N   S   K   R   W   N   P   E   I   Q
2041 GTGGAAATTGAGTGGGAGCTACAGAAAGAAAACAGCAAACGTTGGAATCCAGAGATTCAG

701 Y   T   S   N   Y   N   K   S   V   N   V   D   F   T   V   D   T   N   G   V
2101 TACACTTCCAACTACAACAAGTCTGTTAATGTGGACTTTACTGTAGACACTAATGGTGTT

721 Y   S   E   P   R   P   I   G   T   R   Y   L   T   R   N   L   *      (SEQ ID NO: 4)
2161 TATAGTGAACCTCGCCCTATTGGAACCCGGTATCTCACACGAAACTTGTGA           (SEQ ID NO: 3)
```

Figure 2

```
                    ApaI
ACCACCAGCACCAGAACCTGGGCCCTGCCCACTTACAACAACCATCTCTACAAGCAAATC
TCCAGCVVMDCAGGAGCTASCAACGACAACCACTACTTTGGCTACAGCACCCCTTGGGGG
TATTTGACTTTAACAGATTCCACTGCCACTTCTCACCACGTGACTGGCAGCGACTCATT
AACAACAACTGGGGATTCCGGCCCAAGAAACTCAGCTTCAAGCTCTTCAACATCCAAGTT
AGAGGGGTCACGCAGAACGATGGCACGACGACTATTGCCAATAACCTTACCAGCACGGTT
CAAGTGTTTACGGACTCGGAGTATCAGCTCCCGTACGTGCTCGGGTCGGCGCACCAAGGC
TGTCTCCCGCCGTTTCCAGCGGACGTCTTCATGGTCCCTCAGTATGGATACCTCACCCTG
AACAACGGAAGTCAAGCGGTGGGACGCTCATCCTTTACTGCCTGGAGTACTTCCCTTCG
CAGATGCTAAGGACTGGAAATAACTTCCAATTCAGCTATACCTTCGAGGATGTACCTTTT
CACAGCAGCTACGCTCACAGCCAGAGTTTGGATCGCTTGATGAATCCTCTTATTGATCAG
TATCTGTACTACCTGAACAGAACGCAARGCAMCVCNRGCGGAACARCCRVCMHSMRSVVS
CTGVNGTTTAGCCAGGCTGGGCCTCAGTCTATGTCTTTGCAGGCCAGAAATTGGCTACCT
GGGCCCTGCTACCGGCAACAGAGACTTTCAAMARYCBMCRVCSRSAACAACAACAGTRAS
TTTCCTTGGMCAGCGGCCAGCAMATATCATCTCAATGGCCGCGACTCGCTGGTGAATCCA
GGACCAGCTATGGCCAGTCACRRGGACGATRMSGRSARATTTTTCCCTATGCACGGCAAT
CTAATATTTGGCAAASAARRCRSCRVSRVARVCRATRYCGMSDWCGRSVRSGTAATGATT
ACGGATGAAGAAGAGATTCGTACCACCAATCCTGTGGCAACAGAGCAGTATGGAACTGTG
GCAAATAACTTGCAGRVSVVSMRSRVCVVSCCCACGDHTVVSRNSGTCVMSCATCAGGGG
GCCTTACCTGGCATGGTGTGGCAAGATCGTGACGTCTACCTTCAAGGACCTATCTGGGCA
(SEQ NO: 5)
                              AatII
```

Figure 3

```
MAADGYLPDWLEDNLSEGIREWWALKPGVPQPKANQQHQDNRRGLVLPGYKYLGPGNGLD
KGEPVNEADAAALEHDKAYDQQLKAGDNPYLKYNHADAEFQERLQEDTSFGGNLGRAVFQ
AKKRILEPLGLVEEAAKTAPGKKGAVDQSPQEPDSSSGVGKSGKQPARKRLNFGQTGDSE
SVPDPQPLGEPPAAPTSLGSNTMASGGGAPMADNNEGADGVGNSSGNWHCDSQWLGDRVI
TTSTRTWALPTYNNHLYKQISSXXGAXNDNHYFGYSTPWGYFDFNRFHCHFSPRDWQRLI
NNNWGFRPKKLSFKLFNIQVRGVTQNDGTTTIANNLTSTVQVFTDSEYQLPYVLGSAHQG
CLPPFPADVFMVPQYGYLTLNNGSQAVGRSSFYCLEYFPSQMLRTGNNFQFSYTFEDVPF
HSSYAHSQSLDRLMNPLIDQYLYYLNRTQXXXXGTXXXXXLXFSQAGPQSMSLQARNWLP
GPCYRQQRLSXXXXXNNNSXFPWXAASXYHLNGRDSLVNPGPAMASHKDDXXXFFPMHGN
LIFGKKXXXXXXXXXXXVMITDEEEIRTTNPVATEQYGTVANNLQXXXXXKPTXXXVKHQG
ALPGMVWQDRDVYLQGPIWA (SEQ ID NO: 2)
```

Figure 4

| | | |
|---|---|---|
| 259 Q | 491 KT | 539 G |
| 260 I | 492 TIAV (SEQ ID NO: 119) | 540 N |
| 261 S | 493 APHDSY (SEQ ID NO: 120) | 541 L |
| 262 S | 494 NTSDAG (SEQ ID NO: 114) | 542 I |
| (SEQ ID NO: 113) 263 QNKTSRHPDEAG | 495 DEGQHR (SEQ ID NO: 121) | 543 F |
| 264 STA | 496 N | 544 G |
| VR-I 265 G | 497 N | 545 K |
| 266 A     VR-V | 498 N | 546 EQ |
| 267 ST | 499 S | 547 GNSD (SEQ ID NO: 125) |
| 268 N | 500 NKED (SEQ ID NO: 122) | 548 TSGA (SEQ ID NO: 126) |
| 269 D | 501 F | 549 TKNRSEDAG |
| 270 N | 502 P       (SEQ ID NO: 127) | 550 AKTREG |
| ... | 503 W      (SEQ ID NO: 128) | 551 SNTDAG |
| 445 L | 504 TP     (SEQ ID NO: 129) | 552 ND |
| 446 N | 505 A       VR-VII | 553 ATIV (SEQ ID NO: 130) |
| 447 R | 506 A | 554 EAD |
| 448 T | 507 S       (SEQ ID NO: 131) | 555 LNIDVYF |
| 449 Q | 508 KT | 556 DEG |
| 450 GS | 509 Y       (SEQ ID NO: 132) | 557 NKRSQHEDG |
| 451 TN | 510 H | 558 V |
| 452 TPA | 511 L | 559 M |
| 453 SG | 512 N | 560 I |
| 454 G | 513 G | ... |
| 455 T | 514 R | 580 V |
| VR-IV 456 TA | 515 D | 581 A |
| 457 NTSDAG (SEQ ID NO: 114) | 516 S | 582 N |
| 458 QHPLKNTMI (SEQ ID NO: 115) | 517 L | 583 N |
| 459 SQHRKN (SEQ ID NO: 116) | 518 V | 584 L |
| (SEQ ID NO: 117) 460 RKNTSQHPEDAG | 519 N | 585 Q |
| 461 L | 520 P       (SEQ ID NO: 133) | 586 SKNTREDAG |
| (SEQ ID NO: 118) 462 LKTRMQPEAGV | 521 G      (SEQ ID NO: 134) | 587 SKNTRQHPEDAG |
| 463 F | 522 P       (SEQ ID NO: 135) | 588 NQHRKS |
| 464 S | 523 A       (SEQ ID NO: 136) | 589 TNSDAG |
| 465 Q | 524 M      (SEQ ID NO: 137) | 590 AKNTRSQHPEDG |
| ... | 525 A       VR-VIII | 591 P |
| 485 R | 526 S | 592 T |
| 486 Q | 527 H       (SEQ ID NO: 138) | 593 TNIDAVYSF |
| 487 Q       (SEQ ID NO: 123) | 528 KREG   (SEQ ID NO: 139) | 594 GKNTRSQHPEDA |
| 488 R | 529 D       (SEQ ID NO: 140) | 595 TKNRSMIEDAGV |
| 489 L       VR-VI | 530 D | 596 V |
| 490 S       (SEQ ID NO: 124) | 531 ETKNAD (SEQ ID NO: 141) | 597 NTKPQHAED |
| | 532 EDG | 598 H |
| | 533 KR | 599 Q |
| | 534 F | 600 G |
| | 535 F | |
| | 536 P | |
| | 537 M | |
| | 538 H | |

SYNTHETIC COMBINATORIAL AAV3 CAPSID LIBRARY

CROSS REFERENCE TO RELATED APPLICATIONS

This Application is a national stage filing under 35 U.S.C. § 371 of International Patent Application Serial No. PCT/US2016/058130, filed Oct. 21, 2016, entitled "SYNTHETIC COMBINATORIAL AAV3 CAPSID LIBRARY", which claims priority under 35 USC § 119(e) to U.S. Provisional Application Ser. No. 62/245,025, filed Oct. 22, 2015, entitled "SYNTHETIC COMBINATORIAL AAV3 CAPSID LIBRARY". The entire contents of these applications are incorporated herein by reference in their entirety.

GOVERNMENT SUPPORT

The invention was made with government support under Grant No. HL097088 awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jan. 22, 2024, is named U119670028US01-SUBSEQ-PRW and is 80,664 bytes in size.

BACKGROUND OF THE INVENTION

Adeno-associated virus (AAV) is a single-stranded DNA virus belonging to the Parvoviridae family (Muzyczka and Berns, 2001). AAV-derived vectors are promising tools for human gene therapy applications because of their absence of pathogenicity, low immunogenicity, episomal localization and stable transgene expression. However, significant limitations to the clinical use of AAV are its promiscuity and its susceptibility to neutralization by human antibodies (Jeune et al., 2013). Both of these limitations are determined by nature of the amino acid residues exposed at the surface of the capsid. Therefore, major efforts aiming at developing useful and effective gene therapy vectors have been devoted to obtaining and studying capsid variants (Wu et al., 2006). The first approach was to study naturally occurring AAV isolates. So far, 13 serotypes have been formally characterized and hundreds of variant isolates have been sequenced. Additional capsid variation has been investigated through the generation of mosaics (viral particles made of capsid proteins from more than one serotype) (Hauck et al., 2003; Stachler and Bartlett, 2006; Gigout et al., 2005), chimeras (capsid proteins with domains from various origins) (Shen et al., 2007), and various substitutional or insertional mutants (Wu et al., 2000). However, the most significant advances are expected to result from directed evolution approaches through the development of capsid libraries.

The various strategies to generate capsid libraries that have been developed so far all suffer from sequence bias or limited diversity. Random display peptide libraries (Govindasamy et al., 2006) are limited to an insertion at one particular capsid location. Libraries generated using error-prone PCR contain a very small fraction of gene variants encoding proteins that can fold properly and assemble into a functional capsid, due to the randomness of the mutations. DNA shuffling and staggered extension processes are more efficient because they recombine naturally-occurring parental sequences and therefore are more likely to generate actual capsid variants. However, they can only recombine blocks of DNA as opposed to single nucleotide positions, which results in sequence bias (parental polymorphisms will tend to cluster together instead of being randomly distributed).

SUMMARY OF THE INVENTION

An embodiment of a non-naturally occurring nucleic acid of these teachings includes (a) a first nucleotide sequence encoding at least one AAV Rep protein from serotype 3; (b) a second nucleotide sequence encoding at least one AAV Cap protein differing from wildtype serotype 3 at least at one nucleotide position; and (c) a first AAV terminal repeat from serotype 3 and a second AAV terminal repeat from serotype 3, where the first and second nucleotide sequences are interposed between the first and second AAV terminal repeat.

An aspect of an embodiment of the non-naturally occurring nucleic acid of these teachings further includes a third nucleotide sequence encoding at least one molecule providing helper function. The third nucleotide sequence can be a polynucleotide from an adenovirus or a herpes virus, preferably adenovirus.

An embodiment of a vector library of these teachings includes at least a first vector and a second vector, and each vector includes (a) a first nucleotide sequence encoding at least one AAV Rep protein from serotype 3; (b) a second nucleotide sequence encoding at least one AAV Cap protein differing from wildtype serotype 3 at least at one nucleotide position; and (c) a first AAV terminal repeat from serotype 3 and a second AAV terminal repeat from serotype 3, where the first and second nucleotide sequences are interposed between the first and second AAV terminal repeat, and the second vector differs from the first vector by at least one nucleotide.

An aspect of an embodiment of the vector library of these teachings includes the vector library being incorporated into at least one host cell. Examples of suitable host cells include HEK293 embryonic kidney cells, HeLa cells, Cos cells, U87 cells, KB cells, HepG2 cells and Vero cells, preferably HEK293 embryonic kidney cells.

An aspect of an embodiment of the vector library of these teachings further includes a third nucleotide sequence encoding at least one molecule providing helper function. The third nucleotide sequence can be a polynucleotide from an adenovirus or a herpes virus, preferably adenovirus.

An embodiment of an AAV virion of these teachings includes (a) a first nucleotide sequence encoding at least one AAV Rep protein from serotype 3; (b) a second nucleotide sequence encoding at least one AAV Cap protein differing from wildtype serotype 3 at least at one nucleotide position; and (c) a first AAV terminal repeat from serotype 3 and a second AAV terminal repeat from serotype 3, where the first and second nucleotide sequences are interposed between the first and second AAV terminal repeat.

An aspect of an embodiment of the AAV virion of these teachings includes the AAV virion being incorporated into at least one host cell. Examples of suitable host cells are mammalian cells including human host cells, including, for example blood cells, stem cells, hematopoietic cells, CD34' cells, liver cells, cancer cells, vascular cells, pancreatic cells, neural cells, ocular or retinal cells, epithelial or endothelial cells, dendritic cells, fibroblasts, or any other cell of mammalian origin, including, without limitation, hepatic (i.e., liver) cells, lung cells, cardiac cells, pancreatic cells, intestinal cells, diaphragmatic cells, renal (i.e., kidney) cells, neural cells, blood cells, bone marrow cells, or any one or more selected tissues of a mammal for which viral-based gene therapy is contemplated. Preferably, the host cells are liver cells.

An aspect of an embodiment of the AAV virion of these teachings further includes a third nucleotide sequence encoding at least one molecule providing helper function. The third nucleotide sequence can be a polynucleotide from an adenovirus or a herpes virus, preferably adenovirus.

Certain embodiments of the non-naturally occurring nucleic acid and the vector library and the AAV virion of these teachings include the second nucleotide having the sequence:

```
                                                  (SEQ ID NO: 1)
TGCCCACTTACAACAACCATCTCTACAAGCAAATC

TCCAGCVVMDCAGGAGCTASCAACGACAACCACTACTTTGGCTACAGCAC

CCCTTGGGGGTATTTTGACTTTAACAGATTCCACTGCCACTTCTCACCAC

GTGACTGGCAGCGACTCATTAACAACAACTGGGGATTCCGGCCCAAGAAA

CTCAGCTTCAAGCTCTTCAACATCCAAGTTAGAGGGGTCACGCAGAACGA

TGGCACGACGACTATTGCCAATAACCTTACCAGCACGGTTCAAGTGTTTA

CGGACTCGGAGTATCAGCTCCCGTACGTGCTCGGGTCGGCGCACCAAGGC

TGTCTCCCGCCGTTTCCAGCGGACGTCTTCATGGTCCCTCAGTATGGATA

CCTCACCCTGAACAACGGAAGTCAAGCGGTGGGACGCTCATCCTTTTACT

GCCTGGAGTACTTCCCTTCGCAGATGCTAAGGACTGGAAATAACTTCCAA

TTCAGCTATACCTTCGAGGATGTACCTTTTCACAGCAGCTACGCTCACAG

CCAGAGTTTGGATCGCTTGATGAATCCTCTTATTGATCAGTATCTGTACT

ACCTGAACAGAACGCAARGCAMCVCNRGCGGAACARCCRVCMHSMRSVVS

CTGVNGTTTAGCCAGGCTGGGCCTCAGTCTATGTCTTTGCAGGCCAGAAA

TTGGCTACCTGGGCCCTGCTACCGGCAACAGAGACTTTCAAMARYCBMCR

VCSRSAACAACAACAGTRASTTTCCTTGGMCAGCGGCCAGCAMATATCAT

CTCAATGGCCGCGACTCGCTGGTGAATCCAGGACCAGCTATGGCCAGTCA

CRRGGACGATRMSGRSARATTTTTCCCTATGCACGGCAATCTAATATTTG

GCAAASAARRCRSCRVSRVARVCRATRYCGMSDWCGRSVRSGTAATGATT

ACGGATGAAGAAGAGATTCGTACCACCAATCCTGTGGCAACAGAGCAGTA

TGGAACTGTGGCAAATAACTTGCAGRVSVVSMRSRVCVVSCCCACGDHTV

VSRNSGTCVMSCATCAGGGGGCCTTACCTGGCATGGTGTGGCAAGATCG

T.
```

Certain embodiments of the non-naturally occurring nucleic acid and the vector library and the AAV virion of these teachings include the second nucleotide sequence encoding an AAV Cap protein that differs from wildtype serotype 3 at least at one amino position. The at least one differing amino acid position is preferably in a variable region (VR), and can be in VR-I, VR-IV, VR-V, VR-VI, VR-VII, VR-VIII and combinations thereof.

Certain aspects of the non-naturally occurring nucleic acid and the vector library and the AAV virion of these teachings include VR-I encoding amino acid sequence $X_1X_2GAX_3$ where $X_1$ is independently Q, N, K, T, S, R, H, P, D, E, A or G; $X_2$ is independently S, T or A; and $X_3$ is independently S or T.

Certain aspects of the non-naturally occurring nucleic acid and the vector library and the AAV virion of these teachings include VR-IV encoding amino acid sequence $X_4X_5X_6X_7GTX_8X_9X_{10}X_{11}X_{12}LX_{13}$ where $X_4$ is independently G or S; $X_5$ is independently T or N; $X_6$ is independently T, P or A; $X_7$ is independently S or G; $X_8$ is independently T or A; $X_9$ is independently N, T, S, D, A or G; $X_{10}$ is independently Q, H, P, L, K, N, T, M or I; $X_{11}$ is independently S, Q, H, R, K or N; $X_{12}$ is independently R, K, N, T, S, Q, H, P, E, D, A or G; and $X_{13}$ is independently L, K, T, R, M, Q, P, E, A, G or V.

Certain aspects of the non-naturally occurring nucleic acid and the vector library and the AAV virion of these teachings include VR-V encoding amino acid sequence $X_{14}X_{15}X_{16}X_{17}X_{18}NNNSX_{19}FPWX_{20}AASX_{21}$ where $X_{14}$ is independently K or T; $X_{15}$ is independently T, I, A or V; $X_{16}$ is independently A, P, H, D, S or Y; $X_{17}$ is independently N, T, S, D, A or G; $X_{18}$ is independently D, E, G, Q, H or R; $X_{19}$ is independently N, K, E or D; $X_{20}$ is independently T or P; and $X_{21}$ is independently K or T.

Certain aspects of the non-naturally occurring nucleic acid and the vector library and the AAV virion of these teachings include VR-VI encoding amino acid sequence $X_{22}DDX_{23}X_{24}X_{25}$ where $X_{22}$ is independently K, R, E or G; $X_{23}$ is independently E, T, K, N, A or D; $X_{24}$ is independently E, D or G; and $X_{25}$ is independently K or R.

Certain aspects of the non-naturally occurring nucleic acid and the vector library and the AAV virion of these teachings include VR-VII encoding amino acid sequence $X_{26}X_{27}X_{28}X_{29}X_{30}X_{31}X_{32}X_{33}X_{34}X_{35}X_{36}X_{37}$ where $X_{26}$ is independently E or Q; $X_{27}$ is independently G, N, S or D; $X_{28}$ is independently T, S, G or A; $X_{29}$ is independently T, K, N, R, S, E, D, A or G; $X_{30}$ is independently A, K, T, R, E or G; $X_{31}$ is independently S, N, T, D, A or G; $X_{32}$ is independently N or D; $X_{33}$ is independently A, T, I or V; $X_{34}$ is independently E, A or D; $X_{35}$ is independently L, N, I, D, V, Y or F; $X_{36}$ is independently D, E or G; and $X_{37}$ is independently N, K, R, S, Q, H, E, D or G.

Certain aspects of the non-naturally occurring nucleic acid and the vector library and the AAV virion of these teachings include VR-VIII encoding amino acid sequence $X_{38}X_{39}X_{40}X_{41}X_{42}PTX_{43}X_{44}X_{45}VX_{46}$ where $X_{38}$ is independently S, K, N, T, R, E, D, A or G; $X_{39}$ is independently S, K, N, T, R, Q, H, P, E, D, A or G; $X_{40}$ is independently N, Q, H, R, K or S; $X_{41}$ is independently T, N, S, D, A or G; $X_{42}$ is independently A, K, N, T, R, S, Q, H, P, E, D or G; $X_{43}$ is independently T, N, I, D, A, V, Y, S or F; $X_{44}$ is independently G, K, N, T, R, S, Q, H, P, E, D or A; $X_{45}$ is independently T, K, N, R, S, M, I, E, D, A, G, or V; and $X_{46}$ is independently N, T, K, P, Q, H, A, E or D.

Certain aspects of the non-naturally occurring nucleic acid and the vector library and the AAV virion of these teachings include the second nucleotide sequence encoding an AAV Cap protein having the sequence:

```
                                                  (SEQ ID NO: 2)
MAADGYLPDWLEDNLSEGIREWWALKPGVPQPKANQQHQDNRRGLVLPGY

KYLGPGNGLDKGEPVNEADAAALEHDKAYDQQLKAGDNPYLKYNHADAEF

QERLQEDTSFGGNLGRAVFQAKKRILEPLGLVEEAAKTAPGKKGAVDQSP

QEPDSSSGVGKSGKQPARKRLNFGQTGDSESVPDPQPLGEPPAAPTSLGS

NTMASGGGAPMADNNEGADGVGNSSGNWHCDSQWLGDRVITTSTRTWALP

TYNNHLYKQISSXXGAXNDNHYFGYSTPWGYFDFNRFHCHFSPRDWQRLI
```

-continued

```
NNNWGFRPKKLSFKLFNIQVRGVTQNDGTTTIANNLTSTVQVFTDSEYQL

PYVLGSAHQGCLPPFPADVFMVPQYGYLTLNNGSQAVGRSSFYCLEYFPS

QMLRTGNNFQFSYTFEDVPFHSSYAHSQSLDRLMNPLIDQYLYYLNRTQX

XXXGTXXXXXLXFSQAGPQSMSLQARNWLPGPCYRQQRLSXXXXXNNNSX

FPWXAASXYHLNGRDSLVNPGPAMASHXDDXXXFFPMHGNLIFGKXXXXX

XXXXXXXVMITDEEEIRTTNPVATEQYGTVANNLQXXXXXPTXXXVXHQG

ALPGMVWQDRDVYLQGPIWA.
```

Certain aspects of the non-naturally occurring nucleic acid and the vector library and the AAV virion of these teachings include the second nucleotide encoding variants of an AAV Cap protein as listed in Table 4 (sequences numbered 2-86).

An embodiment of an AAV virion of these teachings includes (a) a first nucleotide sequence encoding at least one therapeutic molecule; (b) a second nucleotide sequence comprising a regulatory sequence; (c) a third nucleotide sequence comprising a first AAV terminal repeat from serotype 3; (d) a fourth nucleotide sequence comprising a second AAV terminal repeat from serotype 3; and (e) a capsid comprising at least one AAV Cap protein that differs from wildtype serotype 3 at least at one amino acid position. The first nucleotide sequence is operably linked to the second nucleotide sequence and the first and second nucleotide sequences are interposed between the first and second AAV terminal repeat to form a transgene, and the resulting transgene is packaged within the capsid. Examples of suitable regulatory sequences include promoters and enhancers, preferably a tissue specific promoter. Examples of suitable therapeutic molecules include polypeptides, peptides, antibody, antigen binding fragment, ribozyme, peptide nucleic acid, siRNA, RNAi, antisense oligonucleotide, antisense polynucleotide, and any combination thereof, preferably a polypeptide, a peptide or an RNA.

An embodiment of a method of treating a disease of these teachings includes administering an effective amount of an AAV virion of these teachings. Such an AAV virion includes (a) a first nucleotide sequence encoding at least one therapeutic molecule; (b) a second nucleotide sequence comprising a regulatory sequence; (c) a third nucleotide sequence comprising a first AAV terminal repeat from serotype 3; (d) a fourth nucleotide sequence comprising a second AAV terminal repeat from serotype 3; and (e) a capsid comprising at least one AAV Cap protein that differs from wildtype serotype 3 at least at one amino acid position. The first nucleotide sequence is operably linked to the second nucleotide sequence and the first and second nucleotide sequences are interposed between the first and second AAV terminal repeat to form a transgene, and the resulting transgene is packaged within the capsid. Examples of suitable regulatory sequences include promoters and enhancers, preferably a tissue specific promoter. Examples of suitable therapeutic molecules include polypeptides, peptides, antibody, antigen binding fragment, ribozyme, peptide nucleic acid, siRNA, RNAi, antisense oligonucleotide, antisense polynucleotide, and any combination thereof, preferably a polypeptide, a peptide or an RNA.

An embodiment of a method of selecting tissue-specific or cell-specific variants of an AAV virion includes (a) introducing a plurality of AAV virions into target tissues or cells; (b) allowing sufficient time to elapse to propagate additional virions; and (c) isolating the virions. Such an AAV virion includes (a) a first nucleotide sequence encoding at least one AAV Rep protein from serotype 3; (b) a second nucleotide sequence encoding at least one AAV Cap protein differing from wildtype serotype 3 at least at one nucleotide position; and (c) a first AAV terminal repeat from serotype 3 and a second AAV terminal repeat from serotype 3, where the first and second nucleotide sequences are interposed between the first and second AAV terminal repeat. Steps (a)-(c) can be repeated one or more times to enrich for a tissue-specific or cell-specific variant. Such enriched variants exhibit a higher target tropism for the target tissues or cells as compared to AAV serotype 3.

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The application contains at least one drawing that is executed in color. Copies of this patent or patent application publication with color drawing(s) will be provided by the Patent and Trademark Office upon request and payment of the necessary fee. The invention may be better understood by reference to the following description taken in conjunction with the accompanying drawings, in which like reference numerals identify like elements.

BRIEF DESCRIPTION OF THE DRAWINGS

FIGS. 1A-1B show the wildtype (WT) nucleotide sequence (bottom rows) and corresponding WT amino acids (top rows, bold font) of AAV3B capsid gene and capsid protein, respectively. Degenerate positions within each variable region (VR) diversified in AAV serotype 3 capsid library (A3CL) are underlined. The degenerate nucleotide positions (in IUPAC code) encoded by synthetic oligonucleotides are shown in italics below the WT sequence.

FIG. 2 shows the nucleotide sequence of the synthetic fragment A3CL as designed. The degenerate nucleotide positions (in IUPAC code) are underlined. The overlap stretches of the synthetic DNA and the plasmid vector backbone are in bold.

FIG. 3 shows the amino acid sequence of AAV3B VP1. Degenerate positions are labeled by X and underlined.

FIG. 4 shows the amino acid sequences of the A3CL VRs encompassing WT AAV3B VP1 capsid residues 259-600. WT sequences are shown in black, degenerate residues—in italics. Not modified conservative residues between VRs are not shown. VRs borders are indicated by vertical lines.

DETAILED DESCRIPTION OF THE INVENTION

Figure 5:
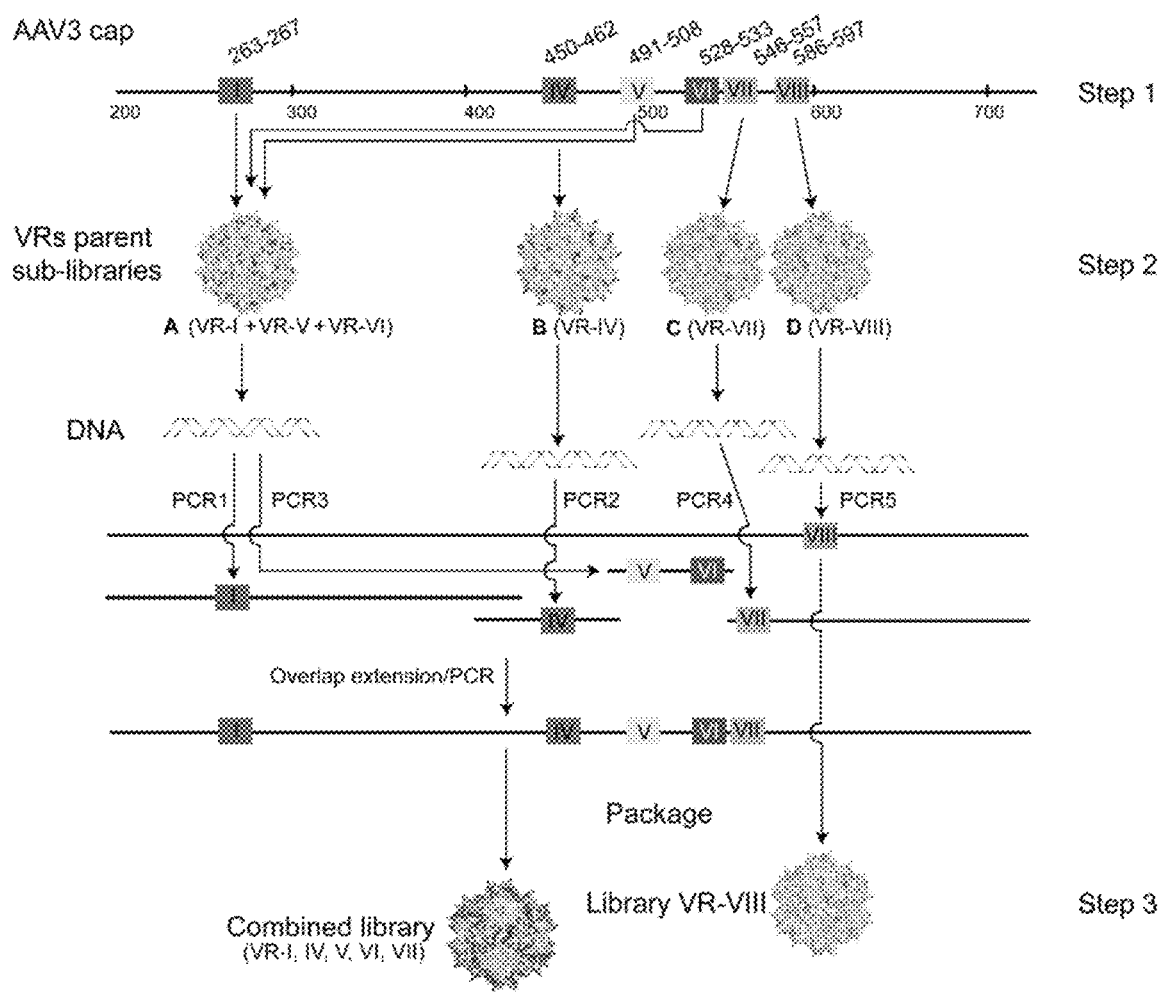
FIG. 5 is a flowchart illustrating design and construction of AAV3B (A3CL) combinatorial capsid libraries ABC and D.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

The present invention also provides improved rAAV-based genetic constructs that encode one or more therapeutic agents useful in the preparation of medicaments for the prevention, treatment, and/or amelioration of one or more diseases, disorders or dysfunctions resulting from a deficiency in one or more cellular components. In particular, the invention provides libraries of rAAV-based genetic constructs encoding one or more selected molecules of interest, such as, for example, one or more diagnostic or therapeutic agents (including, e.g., proteins, polypeptides, peptides, antibodies, antigen binding fragments, siRNAs, RNAis, antisense oligo- and poly-nucleotides, ribozymes, and variants and/or active fragments thereof), for use in the diagnosis, prevention, treatment, and/or amelioration of symptoms of mammalian diseases, disorders, dysfunctions, deficiencies, defects, trauma, injury, and such like.

The present invention also provides infectious rAAV virions, as well as nucleic acid molecules and rAAV vectors that encode the novel AAV vectors described herein, as well as nucleic acids encoding one or more selected diagnostic and/or therapeutic agents for delivery to a selected population of mammalian cells.

Preferably, the novel rAAV vectors, express constructs, and infectious virions and viral particles comprising them as disclosed herein preferably have an improved efficiency in transducing one or more of a variety of cells, tissues and organs of interest, when compared to wild-type, unmodified, expression constructs, and to the corresponding rAAV vectors and virions comprising them.

The improved rAAV vectors provided herein may transduce one or more selected host cells at higher-efficiencies (and often much higher efficiencies) than conventional, wild type (i.e., "unmodified") rAAV vectors. Likewise, vectors prepared as described herein may be of different AAV serotypes, and the mutation of one or more of the sequences described herein may result in improved viral vectors, which are capable of higher-efficiency transduction than that of the corresponding, non-substituted vectors from which the mutants were prepared.

The development of next-generation rAAV viral vectors may dramatically reduce the number of viral particles needed for a conventional gene therapy regimen. In addition to having improved transduction efficiencies for various mammalian cells, the rAAV vectors prepared as described herein may be more stable, less immunogenic, and/or can be produced at much lower cost, or in a higher titer, than an equivalent wild type viral vector prepared in conventional fashion.

In the practice of the invention, native amino acids normally present in the sequence of a viral capsid protein, may be substituted by one or more non-native amino acids, including, a substitution of one or more amino acids not normally present at a particular residue in the corresponding wild-type protein.

The invention also provides isolated and purified polynucleotides that encode one or more of the disclosed viral vectors as described herein, as well as polynucleotides that encode such vectors. Preferably, the vector constructs of the present invention further include at least promoter capable of expressing the nucleic acid segment in a suitable host cell comprising the vector.

In the practice of the invention, the transduction efficiency of a mutated rAAV vector will be higher than that of the corresponding, unmodified, wild-type vector, and as such, will preferably possess a transduction efficiency in a mammalian cell that is at least 2-fold, at least about 4-fold, at least about 6-fold, at least about 8-fold, at least about 10-fold, or at least about 12-fold or higher in a selected mammalian host cell than that of a virion that comprises a corresponding, unmodified, rAAV vector. In certain embodiments, the transduction efficiency of the rAAV vectors provided herein will be at least about 15-fold higher, at least about 20-fold higher, at least about 25-fold higher, at least about 30-fold higher, or at least about 40, 45, or 50-fold or more greater than that of a virion that comprises a corresponding, wild-type vectors.

The present invention also concerns rAAV vectors, wherein the nucleic acid segment further comprises a promoter, an enhancer, a post-transcriptional regulatory sequence, a polyadenylation signal, or any combination thereof, operably linked to the nucleic acid segment that encodes the selected polynucleotide of interest. Preferably, the promoter is a heterologous promoter, a tissue-specific promoter, a cell-specific promoter, a constitutive promoter, an inducible promoter, or any combination thereof. In certain embodiments, nucleic acid segments cloned into one or more of the novel rAAV expression vectors described herein will preferably express or encode one or more polypeptides, peptides, ribozymes, peptide nucleic acids, siRNAs, RNAis, antisense oligonucleotides, antisense polynucleotides, antibodies, antigen binding fragments, or any combination thereof.

As noted herein, the therapeutic agents useful in the invention may include one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, chemotherapeutic agents, cytotoxins, or any combination thereof.

The invention further provides populations and pluralities of such rAAV vectors as prepared herein, as well as virions, infectious viral particles, and mammalian host cells that include one or more nucleic acid segments encoding them.

Preferably, the mammalian host cells will be human host cells, including, for example blood cells, stem cells, hematopoietic cells, CD34' cells, liver cells, cancer cells, vascular cells, pancreatic cells, neural cells, ocular or retinal cells, epithelial or endothelial cells, dendritic cells, fibroblasts, or any other cell of mammalian origin, including, without limitation, hepatic (i.e., liver) cells, lung cells, cardiac cells, pancreatic cells, intestinal cells, diaphragmatic cells, renal (i.e., kidney) cells, neural cells, blood cells, bone marrow cells, retinal cells or any one or more selected tissues of a mammal for which viral-based gene therapy is contemplated.

The invention further provides composition and formulations that include one or more of the proteins nucleic acid segments viral vectors, host cells, or viral particles of the present invention together with one or more pharmaceutically-acceptable buffers, diluents, or excipients. Such compositions may be included in one or more diagnostic or therapeutic kits, for diagnosing, preventing, treating or ameliorating one or more symptoms of a mammalian disease, injury, disorder, trauma or dysfunction.

The invention further includes a method for providing a mammal in need thereof with a diagnostically- or therapeutically-effective amount of a selected biological molecule, the method comprising providing to a cell, tissue or organ of a mammal in need thereof, an amount of an rAAV vector; and for a time effective to provide the mammal with a diagnostically- or a therapeutically-effective amount of the selected biological molecule.

The invention further provides a method for diagnosing, preventing, treating, or ameliorating at least one or more symptoms of a disease, a disorder, a dysfunction, an injury, an abnormal condition, or trauma in a mammal. In an overall and general sense, the method includes at least the step of administering to a mammal in need thereof one or more of the disclosed rAAV vectors, in an amount and for a time sufficient to diagnose, prevent, treat or ameliorate the one or more symptoms of the disease, disorder, dysfunction, injury, abnormal condition, or trauma in the mammal.

The invention also provides a method of transducing a population of mammalian cells. In an overall and general sense, the method includes at least the step of introducing into one or more cells of the population, a composition that comprises an effective amount of one or more of the rAAV vectors disclosed herein.

In a further embodiment, the invention also provides isolated nucleic acid segments that encode one or more of the mutant viral capsid proteins as described herein, and provides recombinant vectors, virus particles, infectious virions, and isolated host cells that comprise one or more of the improved vector sequences described and tested herein.

Additionally, the present invention provides compositions, as well as therapeutic and/or diagnostic kits that include one or more of the disclosed AAV compositions, formulated with one or more additional ingredients, or prepared with one or more instructions for their use.

The invention also demonstrates methods for making, as well as methods of using the disclosed improved rAAV vectors in a variety of ways, including, for example, ex situ, in vitro and in vivo applications, methodologies, diagnostic procedures, and/or gene therapy regimens. Because many of the improved vectors described herein are also resistant to proteasomal degradation, they possess significantly increased transduction efficiencies in vivo making them particularly well suited for viral vector-based human gene therapy regimens, and in particular, for delivering one or more genetic constructs to selected mammalian cells in vivo and/or in vitro.

In one aspect, the invention provides compositions comprising AAV vectors, virions, viral particles, and pharmaceutical formulations thereof, useful in methods for delivering genetic material encoding one or more beneficial or therapeutic product(s) to mammalian cells and tissues. In particular, the compositions and methods of the invention provide a significant advancement in the art through their use in the treatment, prevention, and/or amelioration of symptoms of one or more mammalian diseases. It is contemplated that human gene therapy will particularly benefit from the present teachings by providing new and improved viral vector constructs for use in the treatment of a number of diverse diseases, disorders, and dysfunctions.

In another aspect, the invention concerns libraries of rAAV vector mutants that demonstrate improved properties useful in the delivery of one or more therapeutic agents to selected mammalian cells, and particularly for use in the prevention, treatment, and/or amelioration of one or more disorders in a mammal into which the vector construct may be introduced.

The rAAV vectors of the present invention may optionally further include one or more enhancer sequences that are each operably linked to the nucleic acid segment. Exemplary enhancer sequences include, but are not limited to, one or more selected from the group consisting of a CMV enhancer, a synthetic enhancer, a liver-specific enhancer, an vascular-specific enhancer, a brain-specific enhancer, a neural cell-specific enhancer, a lung-specific enhancer, a muscle-specific enhancer, a kidney-specific enhancer, a pancreas-specific enhancer, retinal-specific enhancer and an islet cell-specific enhancer.

Exemplary promoters useful in the practice of the invention include, without limitation, one or more heterologous, tissue-specific, constitutive or inducible promoters, including, for example, but not limited to, a promoter selected from the group consisting of a CMV promoter, a I3-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, a retinal-specific promoter, an elafin promoter, a cytokine promoter, an interferon promoter, a growth factor promoter, an ai-antitrypsin promoter, a brain cell-specific promoter, a neural cell-specific promoter, a central nervous system cell-specific promoter, a peripheral nervous system cell-specific promoter, an interleukin promoter, a serpin promoter, a hybrid CMV promoter, a hybrid I3-actin promoter, an EF 1 promoter, a U1 a promoter, a U1b promoter, a Tet-inducible promoter, a VP1 6-LexA promoter, or any combination thereof. In exemplary embodiments, the promoter may include a mammalian or avian I3-actin promoter.

The vector-encoding nucleic acid segments may also further include one or more post-transcriptional regulatory sequences or one or more polyadenylation signals, including, for example, but not limited to, a woodchuck hepatitis virus post-transcription regulatory element, a polyadenylation signal sequence, or any combination thereof.

Exemplary diagnostic or therapeutic agents deliverable to host cells by the present vector constructs include, but are not limited to, an agent selected from the group consisting of a polypeptide, a peptide, an antibody, an antigen binding fragment, a ribozyme, a peptide nucleic acid, a siRNA, an RNAi, an antisense oligonucleotide, an antisense polynucleotide, and any combination thereof.

In exemplary embodiments, the rAAV vectors obtained by the disclosed methods will preferably encode at least one diagnostic or therapeutic protein or polypeptide selected from the group consisting of a molecular marker, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinsase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

In certain applications, the rAAV vectors of the present invention may include one or more nucleic acid segments that encode a polypeptide selected from the group consisting of BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10 (I87A), viral IL-10, IL-11, IL-12, IL-13, IL-14, IL-15, IL-16, IL-17, IL-18, and any combination thereof.

In another embodiment, the invention concerns genetically-modified, improved-transduction-efficiency rAAV vectors that include at least a first nucleic acid segment that encodes one or more therapeutic agents that alter, inhibit, reduce, prevent, eliminate, or impair the activity of one or more endogenous biological processes in the cell. In particular embodiments, such therapeutic agents may be those that selectively inhibit or reduce the effects of one or more metabolic processes, dysfunctions, disorders, or diseases. In certain embodiments, the defect may be caused by injury or trauma to the mammal for which treatment is desired. In other embodiments, the defect may be caused the over-expression of an endogenous biological compound, while in other embodiments still; the defect may be caused by the under-expression or even lack of one or more endogenous biological compounds.

The genetically-modified rAAV vectors and expression systems of the present invention may also further optionally include a second distinct nucleic acid segment that comprises, consists essentially of, or consists of, one or more enhancers, one or more regulatory elements, one or more transcriptional elements, or any combination thereof, that alter, improve, regulate, and/or affect the transcription of the nucleotide sequence of interest expressed by the modified rAAV vectors.

For example, the rAAV vectors of the present invention may further include a second nucleic acid segment that comprises, consists essentially of, or consists of, a CMV enhancer, a synthetic enhancer, a cell-specific enhancer, a tissue-specific enhancer, or any combination thereof. The second nucleic acid segment may also further comprise, consist essentially of, or consist of, one or more intron sequences, one or more post-transcriptional regulatory elements, or any combination thereof.

The improved vectors and expression systems of the present invention may also optionally further include a polynucleotide that comprises, consists essentially of, or consists of, one or more polylinkers, restriction sites, and/or multiple cloning region(s) to facilitate insertion (cloning) of one or more selected genetic elements, genes of interest, or therapeutic or diagnostic constructs into the rAAV vector at a selected site within the vector.

In further aspects of the present invention, the exogenous polynucleotide(s) that may be delivered into suitable host cells by the improved, capsid-modified, rAAV vectors disclosed herein are preferably of mammalian origin, with polynucleotides encoding one or more polypeptides or peptides of human, non-human primate, porcine, bovine, ovine, feline, canine, equine, epine, caprine, or lupine origin being particularly preferred.

The exogenous polynucleotide(s) that may be delivered into host cells by the disclosed capsid-modified viral vectors may, in certain embodiments, encode one or more proteins, one or more polypeptides, one or more peptides, one or more enzymes, or one or more antibodies (or antigen-binding fragments thereof), or alternatively, may express one or more siRNAs, ribozymes, antisense oligonucleotides, PNA molecules, or any combination thereof. When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a therapeutic agent.

In other embodiments, the invention also provides rAAV vector mutants that are comprised within an infectious adeno-associated viral particle or a virion, as well as pluralities of such virions or infectious particles. Such vectors and virions may be comprised within one or more diluents, buffers, physiological solutions or pharmaceutical vehicles, or formulated for administration to a mammal in one or more diagnostic, therapeutic, and/or prophylactic regimens. The vectors, virus particles, virions, and pluralities thereof of the present invention may also be provided in excipient formulations that are acceptable for veterinary administration to selected livestock, exotics, domesticated animals, and companion animals (including pets and such like), as well as to non-human primates, zoological or otherwise captive specimens, and such like.

The invention also concerns host cells that comprise at least one of the disclosed rAAV expression vectors, or one or more virus particles or virions that comprise such an expression vector. Such host cells are particularly mammalian host cells, with human host cells being particularly highly preferred, and may be either isolated, in cell or tissue culture. In the case of genetically modified animal models, the transformed host cells may even be comprised within the body of a non-human animal itself.

In certain embodiments, the creation of recombinant non-human host cells, and/or isolated recombinant human host cells that comprise one or more of the disclosed rAAV vectors is also contemplated to be useful for a variety of diagnostic, and laboratory protocols, including, for example, means for the production of large-scale quantities of the rAAV vectors described herein. Such virus production methods are particularly contemplated to be an improvement over existing methodologies including in particular, those that require very high titers of the viral stocks in order to be useful as a gene therapy tool. The inventors contemplate that one very significant advantage of the present methods will be the ability to utilize lower titers of viral particles in mammalian transduction protocols, yet still retain transfection rates at a suitable level.

Compositions comprising one or more of the disclosed rAAV vectors, expression systems, infectious AAV particles, or host cells also form part of the present invention, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex; or the tyrosine-modified rAAV vectors may be comprised within a microsphere or a nanoparticle.

Pharmaceutical formulations suitable for intramuscular, intravenous, or direct injection into an organ or tissue or a plurality of cells or tissues of a human or other mammal are particularly preferred, however, the compositions disclosed herein may also find utility in administration to discreet areas of the mammalian body, including for example, formulations that are suitable for direct injection into one or more organs, tissues, or cell types in the body. Such injection sites include, but are not limited to, the brain, a joint or joint capsule, a synovium or subsynovium tissue, tendons, ligaments, cartilages, bone, peri-articular muscle or an articular space of a mammalian joint, as well as direct administration to an organ such as the heart, liver, lung, pancreas, intestine, brain, bladder, kidney, or other site within the patient's body, including, for example, introduction of the viral vectors via intraabdominal, intrathoracic, intravascular, or intracerebroventricular delivery.

Other aspects of the invention concern recombinant adeno-associated virus virion particles, compositions, and host cells that comprise, consist essentially of, or consist of, one or more of the rAAV vectors disclosed herein, such as for example pharmaceutical formulations of the vectors intended for administration to a mammal through suitable means, such as, by intramuscular, intravenous, intra-articular, or direct injection to one or more cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed rAAV vectors (as well as one or more virions, viral particles, transformed host cells or pharmaceutical compositions comprising such vectors); and instructions for using such kits in one or more therapeutic, diagnostic, and/or prophylactic clinical embodiments are also provided by the present invention. Such kits may further comprise one or more reagents, restriction enzymes, peptides, therapeutics, pharmaceutical compounds, or means for delivery of the composition(s) to host cells, or to an animal (e.g., syringes, injectables, and the like). Exemplary kits include those for treating, preventing, or ameliorating the symptoms of a disease, deficiency, dysfunction, and/or injury, or may include components for the large-scale production of the viral vectors themselves, such as for commercial sale, or for use by others, including e.g., virologists, medical professionals, and the like.

Another important aspect of the present invention concerns methods of use of the disclosed rAAV vectors, virions, expression systems, compositions, and host cells described herein in the preparation of medicaments for diagnosing, preventing, treating or ameliorating at least one or more symptoms of a disease, a dysfunction, a disorder, an abnormal condition, a deficiency, injury, or trauma in an animal, and in particular, in a vertebrate mammal. Such methods generally involve administration to a mammal in need thereof, one or more of the disclosed vectors, virions, viral particles, host cells, compositions, or pluralities thereof, in an amount and for a time sufficient to diagnose, prevent, treat, or lessen one or more symptoms of such a disease, dysfunction, disorder, abnormal condition, deficiency, injury, or trauma in the affected animal. The methods may also encompass prophylactic treatment of animals suspected of having such conditions, or administration of such compositions to those animals at risk for developing such conditions either following diagnosis, or prior to the onset of symptoms.

As described above, the exogenous polynucleotide will preferably encode one or more proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

Compositions comprising one or more of the disclosed rAAV vectors, expression systems, infectious AAV particles, host cells also form part of the present invention, and particularly those compositions that further comprise at least a first pharmaceutically-acceptable excipient for use in the manufacture of medicaments and methods involving therapeutic administration of such rAAV vectors. Such pharmaceutical compositions may optionally further comprise liposomes, a lipid, a lipid complex; or the rAAV vectors may be comprised within a microsphere or a nanoparticle. Pharmaceutical formulations suitable for intramuscular, intravenous, or direct injection into an organ or tissue of a human are particularly preferred.

Use of rAAV Vectors in Prophylaxis, Diagnosis, or Therapy

The present invention provides compositions including one or more of the disclosed rAAV vectors comprised within a kit for diagnosing, preventing, treating or ameliorating one or more symptoms of a mammalian disease, injury, disorder, trauma or dysfunction. Such kits may be useful in the diagnosis, prophylaxis, and/or therapy or a human disease, and may be particularly useful in the treatment, prevention, and/or amelioration of one or more symptoms of wet age-related macular degeneration, dry age-related macular degeneration, glaucoma, retinitis pigmentosa, diabetic retinopathy, orphan ophthalmological diseases, cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, ischemia, a 1-antitrypsin (AAT) deficiency, Batten's disease, Alzheimer's disease, sickle cell disease, f3-thalassamia, Huntington's disease, Parkinson's disease, skeletal disease, trauma, pulmonary disease in a human.

The invention also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction.

The invention also provides a method for treating or ameliorating the symptoms of such a disease, injury, disorder, or dysfunction in a mammal. Such methods generally involve at least the step of administering to a mammal in need thereof, one or more of the rAAV vectors as disclosed herein, in an amount and for a time sufficient to treat or ameliorate the symptoms of such a disease, injury, disorder, or dysfunction in the mammal. Such treatment regimens are particularly contemplated in human therapy, via administration of one or more compositions either intramuscularly, intravenously, subcutaneously, intrathecally, intraperitoneally, or by direct injection into an organ or a tissue of the mammal under care.

The invention also provides a method for providing to a mammal in need thereof, a therapeutically-effective amount of an rAAV composition of the present invention, in an amount, and for a time effective to provide the patient with a therapeutically-effective amount of the desired therapeutic agent(s) encoded by one or more nucleic acid segments comprised within the rAAV vector. Exemplary therapeutic agents include, but are not limited to, a polypeptide, a peptide, an antibody, an antigen-binding fragment, a ribozyme, a peptide nucleic acid, an siRNA, an RNAi, an antisense oligonucleotide, an antisense polynucleotide, or a combination thereof.

Pharmaceutical Compositions

The genetic constructs of the present invention may be prepared in a variety of compositions, and may also be formulated in appropriate pharmaceutical vehicles for administration to human or animal subjects.

The invention also provides compositions comprising one or more of the disclosed rAAV vectors, expression systems, virions, viral particles, mammalian cells, or combinations thereof. In certain embodiments, the present invention provides pharmaceutical formulations of one or more rAAV vectors disclosed herein for administration to a cell or an animal, either alone or in combination with one or more other modalities of therapy, and in particular, for therapy of human cells, tissues, and diseases affecting man. Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, intramuscular administration and formulation.

Library Design and Construction

Comparison of the AAV VP3 structure among various serotypes has revealed highly homologous sequences interspersed with more evolutionary divergent areas. These amino acid stretches are commonly designated as VRs I through IX (variable regions I-IX; also known as "loops"). VRs are localized at the surface of the assembled capsid and are assumed to be responsible for the capsid interaction with cell surface receptors and other host factors. Because of their location, VRs are also predicted to be less critical for capsid assembly. Therefore, the guiding principle of the library's design was to modify only surface VRs while keeping the backbone sequence unchanged to maintain the integrity of the assembling scaffold. All candidate positions for mutagenesis, in the AAV3 background, were selected from the alignment of known variants, which can be evaluated on a three dimensional model of the AAV3 capsid. The amino acid diversity of VR-I, VR-IV, VR-V, VR-VI, VR-VII and VR-VIII is shown in FIG. 4. AAV3 wildtype VR-II, VR-III and VR-IX and non-variable regions of VP3 were incorporated in the plasmid library.

The library was built in three steps: first, VR parent sub-libraries were prepared each containing mutations in only one VR (B: VR-IV, C: VR-VII, D: VR-VIII) or a subset of VRs (A: VR-I+VR-V+VR-VI), then, structurally compatible sequences were combined to generate master libraries (A+B+C: VRs I, IV, V, VI, VII) and (D: VR-VIII), and finally the master libraries were packaged. See Examples, Example 2 and FIG. 5. Methods for generating and assembling DNA fragments for the library are disclosed in WO2015/048534 and U.S. Pat. No. 7,220,577, both of which are incorporated herein in their entirety.

Tissue-Specific or Cell-Specific Virions

The master libraries can be used to select virions having capsids containing degenerate or otherwise modified Cap protein (i.e., Cap protein that differs from wildtype serotype 3 at least at one amino acid position) that are targeted to particular tissue or cell types. For example, virions made according to the invention include those that exhibit a new tropism, e.g., those capable of infecting cells normally non-permissive to AAV infection in general or at least non-permissive to AAV3 infection, as well as those that exhibit an increased or decreased ability to infect a particular cell or tissue type. As another example, virions made according to the invention include those that lack the ability to infect cells normally permissive to AAV infection in general or at least normally permissive to AAV3 infection. To select for virions having a particular cell- or tissue-specific tropism, a packaged master library is introduced into a target cell. Preferably, the target cell is also infected with a helper virus (e.g. Ad). The target cell is cultured under conditions that allow for the production of virions, resulting in a population of virions that are harvested from the target cell. This population of virions has been selected for having a tropism for that target cell.

As controls in a typical experiment in which virions having a particular tropism are selected, cells in different flasks or dishes can be simultaneously infected with WT AAV3 or rAAV using the same conditions as used for the library. After a suitable time post-infection, cells can be harvested, washed and the virions purified using a suitable purification method (See Gao et al., Hum. Gene Ther. 9:2353-62, 1998; U.S. Pat. No. 6,146,874; and Zolotukhin et al., Gene Ther. 6:973-85, 1999). AAV and helper virions (e.g., Ad) from each infection can be tittered, by real-time PCT for example, and the AAV virions can then be further propagated, resulting in a stock of selected virions.

Once the selected population of virions having a desired tropism is isolated, nucleic acid from the virions is isolated and the sequence of the nucleotide sequence encoding the at least one AAV Cap protein is determined. Virions made and selected according to the invention that can specifically target diseased cells or tissues over non-diseased cells or tissues are particularly useful.

Alternatively tissue- or cell-specific virions can be selected using an in vivo approach. For example, mice (or other suitable host) can be injected with a suitable amount viral preparation (e.g., $1 \times 10^{10}$ to $1 \times 10^{11}$ vg in the case of mice) via the tail vein. More than one round of selection can be performed by injecting original master library for the first round and target-enriched libraries in subsequent rounds. Hosts are euthanized after an incubation period (3 to 4 days for mice), and episomal DNA is purified from the target cells or tissue and used as a template to amplify capsid DNA sequences. Target-enriched libraries can then be generated, purified and quantified. After several rounds of selection, amplified capsid DNA can be inserted into an appropriate vector for cloning and random clones can be analyzed by sequencing.

Exemplary Definitions

Unless otherwise defined, all technical terms used herein have the same meaning as commonly understood by one of ordinary skill in the art to which this invention belongs. Commonly understood definitions of molecular biology terms can be found in Rieger et al., (1991); Lewin (1994). Commonly understood definitions of virology terms can be found in Granoff and Webster (1999) and Tidona and Darai (2002). Commonly understood definitions of microbiology can be found in Singleton and Sainsbury (2002).

In accordance with long standing patent law convention, the words "a" and "an" when used in this application, including the claims, denotes "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof, that is pharmaceutically acceptable for administration to the relevant animal. The use of one or more delivery vehicles for chemical compounds in general, and chemotherapeutics in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed chemotherapeutic compositions.

As used herein, the term "chimeric rcAAV" refers to a replication-competent AAV-derived nucleic acid containing at least one nucleotide sequence that 1) encodes an AAV protein and 2) differs from the corresponding native nucleotide sequence in one or more bases.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

The term "e.g.," as used herein, is used merely by way of example, without limitation intended, and should not be construed as referring only those items explicitly enumerated in the specification.

As used herein, "an effective amount" would be understood by those of ordinary skill in the art to provide a therapeutic, prophylactic, or otherwise beneficial effect against the organism, its infection, or the symptoms of the organism or its infection, or any combination thereof.

The phrase "expression control sequence" refers to any genetic element (e.g., polynucleotide sequence) that can exert a regulatory effect on the replication or expression (transcription or translation) of another genetic element. Common expression control sequences include promoters, polyadenylation (polyA) signals, transcription termination sequences, upstream regulatory domains, origins of replication, internal ribosome entry sites (IRES), enhancers, and the like. A "tissue specific expression control sequence" is one that exerts a regulatory effect on the replication or expression (transcription or translation) of another genetic element in only one type of tissue or a small subset of tissues.

The phrase "helper function" is meant as a functional activity performed by a nucleic acid or polypeptide that is derived from a virus such as Adenovirus (Ad) or herpesvirus and that facilitates AAV replication in a host cell.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

As used herein, the term "kit" may be used to describe variations of the portable, self-contained enclosure that includes at least one set of components to conduct one or more of the diagnostic or therapeutic methods of the invention.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The term "library" refers to a collection of elements that differ from one another in at least one aspect. For example, a vector library is a collection of at least two vectors that differ from one another by at least one nucleotide. As another example, a "virion library" is a collection of at least two virions that differ from one another by at least one nucleotide or at least one capsid protein.

As used herein, the term "master library" or "combined library" refers to a pool of rAAV virions composed of chimeric rcAAV vectors encapsidated in cognate chimeric capsids (e.g., capsids containing a degenerate or otherwise modified Cap protein).

As used herein, the term "parent sub-library" refers to a pool of rAAV virions composed of chimeric rcAAV vectors encapsidated in cognate chimeric capsids (e.g., capsids containing degenerate or otherwise modified Cap protein). More than one parent sub-library can be combined to create a master library or combined library.

When referring to a nucleic acid molecule or polypeptide, the term "native" refers to a naturally-occurring (e.g., a WT) nucleic acid or polypeptide.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, the phrase "nucleic acid" means a chain of two or more nucleotides such as RNA (ribonucleic acid) and DNA (deoxyribonucleic acid). Conventional nomenclature exists in the art for polynucleotide and polypeptide structures. For example, one-letter abbreviations are widely employed to describe nucleotides: Adenine (A), Guanine (G), Cytosine (C), Thymine (T), Uracil (U), Purine, i.e. A or G (R), Pyrimidine, i.e. C or T (Y), any nucleotide (N), Weak, i.e. A or T (W), Strong, i.e. G or C (S), Amino, i.e. A or C (M), Keto, i.e. G or T (K), not A, i.e. G or C or T (B), not G, i.e. A or C or T (H), not C, i.e. A or G or T (D) and not T, i.e. A or G or C (V).

The phrases "cap nucleic acid," "cap gene," and "capsid gene" as used herein mean a nucleic acid that encodes a Cap protein. Examples of cap nucleic acids include "wild-type" (WT) Cap-encoding nucleic acid sequences from AAV serotypes 1, 2, 3, 4, 5, 6, 7, 8, 9, 10, 11, 12, 13; a native form cap cDNA; a nucleic acid having sequences from which a cap cDNA can be transcribed; and/or allelic variants and homologs of the foregoing.

"VR", "VRs", "variable region" or "variable regions" refer to amino acid stretches of capsid protein that do not have a high degree of homology between AAV variants. These amino acid stretches are commonly designated as VRs I through IX (also known as "loops"). VRs are localized at the surface of the assembled capsid and interact with host cell surface receptors and other host factors.

As used herein, the term "patient" (also interchangeably referred to as "host" or "subject") refers to any host that can receive one or more of the pharmaceutical compositions disclosed herein. Preferably, the subject is a vertebrate animal, which is intended to denote any animal species (and preferably, a mammalian species such as a human being). In certain embodiments, a "patient" refers to any animal host including without limitation any mammalian host. Preferably, the term refers to any mammalian host, the latter including but not limited to, human and non-human primates, bovines, canines, caprines, cavines, corvines, epines, equines, felines, hircines, lapines, leporines, lupines, murines, ovines, porcines, ranines, racines, vulpines, and the like, including livestock, zoological specimens, exotics, as well as companion animals, pets, and any animal under the care of a veterinary practitioner.

The phrase "pharmaceutically-acceptable" refers to molecular entities and compositions that preferably do not produce an allergic or similar untoward reaction when administered to a mammal, and in particular, when administered to a human. As used herein, "pharmaceutically acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkalis such as sodium and ammonia.

As used herein, the term "plasmid" or "vector" refers to a genetic construct that is composed of genetic material (i.e., nucleic acids). Typically, a plasmid or a vector contains an origin of replication that is functional in bacterial host cells, e.g., Escherichia coli, and selectable markers for detecting bacterial host cells including the plasmid. Plasmids and vectors of the present invention may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Additional conventions include: Asn or Asp (B; Asx), Gln or Glu (Z; Glx), Leu or Ile (J; Xle), Selenocysteine (U; Sec), Pyrrolysine (O; Pyl) and Unknown (X; Unk). Amino acid residues described herein are preferred to be in the "L" isomeric form. However, residues in the "D" isomeric form may be substituted for any L-amino acid residue provided the desired properties of the polypeptide are retained.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

The term "promoter," as used herein refers to a region or regions of a nucleic acid sequence that regulates transcription.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from two to about 20 amino acid residues in length, oligopeptides from about 10 to about 100 amino acid residues in length, and longer polypeptides including those of about 100 or more amino acid residues in length. Furthermore, the term is also intended to include enzymes, i.e., functional biomolecules including at least one amino acid polymer. Polypeptides and proteins of the present invention also include polypeptides and proteins that are or have been post-translationally modified, and include any sugar or other derivative(s) or conjugate(s) added to the backbone amino acid chain.

The term "pseudotyped" is meant a nucleic acid or genome derived from a first AAV serotype that is encapsidated (packaged) into an AAV capsid containing at least one AAV Cap protein of a second serotype differing from the first serotype.

As used herein, the term "rcAAV vector" refers to a replication-competent AAV-derived nucleic acid capable of DNA replication in a cell without any additional AAV genes or gene products.

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "RNA segment" refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

The terms "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

As used herein, the term "structural gene" is intended to generally describe a polynucleotide, such as a gene, that is expressed to produce an encoded peptide, polypeptide, protein, ribozyme, catalytic RNA molecule, or antisense molecule.

The term "subject," as used herein, describes an organism, including a mammal such as a human primate, to which treatment with one or more of the disclosed compositions may be provided. Mammalian species that may benefit from the disclosed treatment methods include, without limitation, humans, non-human primates such as apes; chimpanzees;

monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

As used herein, the terms "terminal repeat" or "TR" mean a nucleic acid sequence derived from an AAV that is required in cis for replication and packaging of AAV.

"Transcriptional regulatory element" refers to a polynucleotide sequence that activates transcription alone or in combination with one or more other nucleic acid sequences. A transcriptional regulatory element may include, for example, one or more promoters, one or more response elements, one or more negative regulatory elements, one or more enhancers, or any combination thereof As used herein, a "transcription factor recognition site" and a "transcription factor binding site" refer to a polynucleotide sequence(s) or sequence motif(s) that are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted based on known consensus sequence motifs, or by other methods known to one of ordinary skill in the relevant molecular biological and virology arts.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

As used herein, the term "transformed cell" is intended to mean a host cell whose nucleic acid complement has been altered by the introduction of one or more exogenous polynucleotides into that cell.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

As used herein, the terms "treat," "treating," and "treatment" refer to the administration of one or more compounds (either alone or as contained in one or more pharmaceutical compositions) after the onset of clinical symptoms of a disease state so as to reduce, or eliminate any symptom, aspect or characteristic of the disease state. Such treating need not be absolute to be deemed medically useful. As such, the terms "treatment," "treat," "treated," or "treating" may refer to therapy, or to the amelioration or the reduction, in the extent or severity of disease, of one or more symptom thereof, whether before or after its development afflicts a patient.

As used herein, the term "vector" refers to a nucleic acid molecule capable of transporting another nucleic acid to which it has been linked, e.g., a plasmid. One type of preferred vector is an episome, i.e., a nucleic acid capable of extra-chromosomal replication. Preferred vectors are those capable of autonomous replication and/or expression of nucleic acids to which they are linked. An "rAAV vector" is a recombinant AAV-derived nucleic acid containing at least one terminal repeat (TR) sequence.

The use of "virion" is meant to describe a virus particle that contains a nucleic acid and a protein coat (capsid). An "rAAV virion" is a virion that includes nucleic acid sequences and/or proteins derived from a rAAV vector.

As used herein, the term "tropism" refers to the cells and/or tissues of a host which support growth of a particular serotype of AAV. Some serotypes may have a broad tissue tropism and can infect many types of cells and tissues. Other serotypes may infect primarily a single tissue or cell type.

The term "a sequence essentially as set forth in SEQ ID NO: X" means that the sequence substantially corresponds to a portion of SEQ ID NO: X and has relatively few nucleotides (or amino acids in the case of polypeptide sequences) that are not identical to, or a biologically functional equivalent of, the nucleotides (or amino acids) of SEQ ID NO: X. The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions for the present invention include, for example, hybridization in 50% formamide, 5×Denhardt's solution, 5× SSC, 25 mM sodium phosphate, 0.1% SDS and 100 µg/ml of denatured salmon sperm DNA at 42° C. for 16 h followed by 1 hr sequential washes with 0.1× SSC, 0.1% SDS solution at 60° C. to remove the desired amount of background signal. Lower stringency hybridization conditions for the present invention include, for example, hybridization in 35% formamide, 5×Denhardt's solution, 5× SSC, 25 mM sodium phosphate, 0.1% SDS and 100 µg/ml denatured salmon sperm DNA or E. coli DNA at 42° C. for 16 h followed by sequential washes with 0.8× SSC, 0.1% SDS at 55° C. Those of skill in the art will recognize that conditions can be readily adjusted to obtain the desired level of stringency.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to bp 40, from the second bp of the sequence to bp 41, from the third bp to bp 42, and so forth, while for 50-mers, such probes or primers may correspond to a nucleotide sequence extending from bp 1 to bp 50, from bp 2 to bp 51, from bp 3 to bp 52, from bp 4 to bp 53, and so forth.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernable from the first label. The use of multiplexing assays, particularly in the context of genetic amplification/detection protocols are well-known to those of ordinary skill in the molecular genetic arts.

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure appreciate that many changes can be made in the specific embodiments which are disclosed and still obtain a like or similar result without departing from the spirit and scope of the invention.

Example 1

Step 1: Sub-Libraries Assembly.

Using pITR3-R3C3-AatII as a template, the following ten PCR reactions were conducted:

| Primers | PCR fragment size |
|---|---|
| A3CL-A (VRs-I, V, VI): | |
| 1. A3CL-F + A3CL-A1R (before VR-I) | 86 bp |
| 2. A3CL-A1F + A3CL-A2R (VR-I to most of VR-V) | 747 bp |
| 3. A3CL-A2F + A3CL-A3R (part of VR-V to VR-VI) | 136 bp |
| 4. A3CL-A3F + A3CL-R (after VR-VI) | 281 bp |
| A3CL-B (VR-IV): | |
| 5. A3CL-F + A3CL-B1R (before VR-IV) | 647 bp |
| 6. A3CL-B1F + A3CL-R (VR-IV to end) | 556 bp |
| A3CL-C (VR-VII): | |
| 7. A3CL-F + A3CL-C1R (before VR-VII) | 935 bp |
| 8. A3CL-C1F + A3CL-R (VR-VII to end) | 266 bp |
| A3CL-D (VR-VIII): | |
| 9. A3CL-F + A3CL-D1R (before VR-VIII) | 1055 bp |
| 10. A3CL-D1F + A3CL-R (VR-VIII to end) | 147 bp |

The respective PCR fragments were eluted from the agarose gel, mixed at equimolar ratios as indicated above for sub-libraries A, B, C, and D, and subjected to 15 cycles of overlap extension (OE) without primers, followed by 20 cycles of PCR using A3CL-F forward and A3CL-R reverse primers. The resulting fragments of 1140 bp for each of the A (I+V+VI), B (IV), C (VII), or D (VIII) sub-libraries were purified on agarose gel and eluted in small volume H$_2$O. Using isothermal DNA assembly protocol, the respective fragments were individually sub-cloned into gel-purified pTR3-R3C3-AatII digested with AatII+ApaI. Four plasmid libraries A, B, C, and D, incorporating the respective VRs were derived. The estimated plasmid libraries' complexities were the following: A—4.4×10$^7$; B—1.7×10$^7$; C—1×10$^8$; D—1×10$^8$.

Step 2: Pre-Selecting Structurally Compatible Parent Viral Libraries.

Using plasmid libraries from Step 1, viral sub-libraries A, B, C, and D were packaged, AAV virus from each preparation was purified using iodixanol density gradients, and the viral DNAs were isolated. Next, using viral DNAs as templates, the following PCR reactions were conducted:
1. VR-I, primers A3CL-F+VR-I_IV-R, template A, size 644 bp.
2. VR-IV, primers VR-I_IV-F+VR-IV_V-R, template B, size 145 bp.
3. VR-V+VI, primers VR-IV_V-F+VR-VI_VII-R, template A, size 194 bp.
4. VR-VII, primers VR-VI_VR-VII-F+A3CL-R, template C, size 274 bp.
5. VR-VIII, primers A3CL-F and A3CL-R, template D, size 1140 bp.

The respective PCR fragments were gel-purified and used as the templates in the OE/PCR to derive two PCR fragments, each of 1140 bp: A+B+C (VR-I, IV, V, VI, VII) and D (VR-VIII).

Step 3: Packaging Master Libraries.

Using isothermal DNA assembly protocol, the respective fragments were individually sub-cloned into gel-purified pTR3-R3C3-AatII digested with AatII+ApaI. The estimated plasmid library A+B+C complexity was $2.5 \times 10^7$, plasmid library D complexity was $4 \times 10^7$. Using these plasmid libraries, two TABLE 3-continued Synthetic oligonucleotides used to assemble the AAV3B capsid library

| Name | Sequence |
|---|---|
| A3 CL-D1F | GAACTGTGGCAAATAACTTGCAGRVSVVSMRSRVCVVSCCCACGDHTVVSRNSGTC VMSCATCAGGGGGCCTTACCTG (SEQ ID NO: 19) |
| VR-I_IV-F | CAGTATCTGTACTACCTGAACAGAACGC (SEQ ID NO: 20) |
| VR-I_IV-R | GCGTTCTGTTCAGGTAGTACAGATACTG (SEQ ID NO: 21) |
| VR-IV_V-F | CCTGGGCCCTGCTACCGGCAACAGAG (SEQ ID NO: 22) |
| VR-IV_V-R | CTCTGTTGCCGGTAGCAGGGCCCAGG (SEQ ID NO: 23) |
| VR-VI_VII-F | CCCTATGCACGGCAATCTAATATTTGGC (SEQ ID NO: 24) |
| VR-VI_VII-R | GCCAAATATTAGATTGCCGTGCATAGGG (SEQ ID NO: 25) |

NGS Sequencing.
Number of sequences processed: 1817050
Number of distinct sequences (complexity): 1708473 (0.94)

Copy number distribution

| Copy number | Number of sequences |
|---|---|
| 1 | 1603700 |
| 2 | 101430 |
| 3 | 3257 |
| 4 | 83 |
| 5 | 2 |
| 377 | 1 |

TABLE 4

Examples of the most representative variants within VRs IV, V, VI, and VII from the master viral library ABC as deduced from the NGS sequencing (the dots in each of sequences 1-86 corresponding to SEQ ID NOs: 26 and 27-112 below represent amino acid residues that are identical to those listed in wild type as shown below).

| | 450 | 491 | 528 | 546 | | |
|---|---|---|---|---|---|---|
| Wild type | GTTSGTTNQSRLL | KTANDNNNSNFPWTAASK | KDDEEK | EGTTASNAELDN | cn | % |
| 1 | ............. | .................. | ...... | ............ | 377 | 0.0 |
| 2 | .N.G...SP...R | .IYDR............T | G..TGR | Q...GEG.V.VGK | 5 | 0.0 |
| 3 | S......G.RK.A | .AYGH....D...P...T | G...DR | QDSGENDVAIGR | 5 | 0.0 |
| 4 | ..A....AN.N.K | ..YS.............. | G..DDR | ...DGA.V.I.R | 4 | 0.0 |
| 5 | ..P...AAHKT.E | ..SAE............. | G..AGR | .DAEGGD.AIGG | 4 | 0.0 |
| 6 | S.AG..AT.KA.T | .VHAH............. | E..TGR | QDA.R...VAFEE | 4 | 0.0 |
| 7 | .NP....GLRG.T | T.D.E........P.... | ...AG. | Q..DGN.IAFGE | 4 | 0.0 |
| 8 | .N.....SKRP.M | T....E............T | E..N.R | .DAKGTDT.F.R | 4 | 0.0 |
| 9 | SNA....GIHQ.K | TAPDR....E......... | E..NGR | QNGATADT.VER | 4 | 0.0 |
| 10 | SN.G...AMRE.E | .AP........K.....T | E..TG. | .S.AETDV.DGR | 4 | 0.0 |
| 11 | SNA...AGLQ..K | .IPDQ............. | ...NG. | QSGG.ADIDNG. | 4 | 0.0 |
| 12 | .NP....APH... | TIH.G........P...T | ...DGR | QDGGT..IDI.G | 4 | 0.0 |
| 13 | ..P....DLRE.A | .IP..............T | E...DR | ............ | 4 | 0.0 |

TABLE 4-continued

Examples of the most representative variants within VRs IV, V, VI, and VII from the master viral library ABC as deduced from the NGS sequencing (the dots in each of sequences 1-86 corresponding to SEQ ID NOs: 26 and 27-112 below represent amino acid residues that are identical to those listed in wild type as shown below).

| | | | | |
|---|---|---|---|---|
| 14 | SNP...A.PRT.M .IDAH....E...P...T E...NG. QSS.TGDV.D.D | 4 | 0.0 |
| 15 | .NA....DTK..T .ASGG...........T ...DD. ..SNRDD..V.R | 4 | 0.0 |
| 16 | .N.G...DIR..R ..HSE....E.......T ...N.R QD.RETDVAI.R | 4 | 0.0 |
| 17 | .NA...AGMRE.M .A..H........... E...D. .SGS.DDVAIGR | 4 | 0.0 |
| 18 | SN.G...ATPKQ.Q .ASAH....E........ .....R ...S.RNDIANEH | 4 | 0.0 |
| 19 | SN.G...A.IKE.T ...S.............T R..ND. QSASKNDI.YEQ | 4 | 0.0 |
| 20 | SNAG...SNRE.R T.SSQ............T R..DDR QDAGGNDV.VGD | 4 | 0.0 |
| 21 | SN....ATT.A.K ..YGH............ G..T.. Q.GS.N.V.VES | 4 | 0.0 |
| 22 | SNAG..AATN... .IYDR............T R...D. ..GEKG.VDI.R | 4 | 0.0 |
| 23 | S.P....ATKG.T TAHTG............ G..DG. ...S..TDVAIGS | 4 | 0.0 |
| 24 | .N.G...DLR..M T.D.H....E...P...T G..KGR .NGAKNDIAFEG | 4 | 0.0 |
| 25 | S......TLKA.Q IP.R.............T G...DR .NSKGA.T.I.E | 4 | 0.0 |
| 26 | .......DPKD.V T.HG.....D.......T ...DD. .D.A.D.V.FGR | 4 | 0.0 |
| 27 | S.AG...TIKD.V .VPD.....K........ E...D.R QDSG.T.V.FGR | 4 | 0.0 |
| 28 | ...G...TMRK.G .VYGG............T E...A.R QSSGRNDV.YGD | 4 | 0.0 |
| 29 | .N.G...ASTR..T .IPDQ........P.... E...GR QSAEKGDI.YGR | 4 | 0.0 |
| 30 | .N......ATHT.A .IHSR....D...P.... E..AG. Q.A...G.IDVEQ | 4 | 0.0 |
| 31 | SNPG...SIRG.Q TIP.R........P...T R..TD. Q.GG.G.TDF.H | 4 | 0.0 |
| 32 | S.....AAPRG.V TVYGH....E........ ....GR ...AG...VAIEE | 4 | 0.0 |
| 33 | .NA...ATKQG.M .VP.Q....D........ ...DDR QSSDKN...D.S | 4 | 0.0 |
| 34 | SNAG...ATT.Q.R TAPAE........P...T R..ADR .SGRGD.VDFEK | 4 | 0.0 |
| 35 | SN.G...AGIRA.Q .VDTG....D.......T E..T.. .NSARND.DIGR | 4 | 0.0 |
| 36 | .NA...AA.NG.R .IP.E....K.......T ....G. .SSSGDD..FGG | 4 | 0.0 |
| 37 | SN....AGPQQ.R ..HAQ............ E..TG. ...AR.NDIAF.Q | 4 | 0.0 |
| 38 | S.P....SMRT.E .APAR....E.......T R..AG. Q.SRENDT.F.G | 4 | 0.0 |
| 39 | S.AG...ALKG.K TI.DH....E...P...T R..K.. .DS.GA.IAD.R | 4 | 0.0 |
| 40 | S.P....ASTRT.M ..H.H....E.......T ....D. ...E.T.VAIGG | 4 | 0.0 |
| 41 | .NPG....NQA.R .IHGQ....D.......T R..ND. ...SARGDVAYEK | 4 | 0.0 |
| 42 | SNA....DTRE.V TI.D.....E.......T R..TD. Q.SAGADV.VEK | 4 | 0.0 |
| 43 | SNPG....LRE.R TIHTE....E.......T R..KDR Q.GGGT.V.IGS | 4 | 0.0 |
| 44 | ...G..A.NNT.. .I.SG.............T ...KGR ..AEKNDTAVG. | 4 | 0.0 |
| 45 | .......DKQQ.M ..H.G....D........ E..TG. QSAEGN.VAY.G | 4 | 0.0 |
| 46 | ..AG..ATL.T.V .ISAG....D........ G..NG. QNS...DVAI.G | 4 | 0.0 |
| 47 | SN....AGLRT.T .ADA.....D...P...T G..NG. .DASGN.V.DGR | 4 | 0.0 |
| 48 | SNA...ATP.T.R ..DTH....E...P.... R..NDR ..ARG..IDVGD | 4 | 0.0 |
| 49 | S.A...ASLRA.M .VP.R.............T G..ND. .NAR..D..V.R | 4 | 0.0 |
| 50 | ..A...ATTKG.. .ISTQ............. E..AD. Q.GETD.VDVGD | 4 | 0.0 |

TABLE 4-continued

Examples of the most representative variants within VRs IV, V, VI, and VII from the master viral library ABC as deduced from the NGS sequencing (the dots in each of sequences 1-86 corresponding to SEQ ID NOs: 26 and 27-112 below represent amino acid residues that are identical to those listed in wild type as shown below).

| | | | |
|---|---|---|---|
| 51 | ..A...AALKQ.A .ADS.............T E..ADR Q.GETG.I.Y.G | 4 | 0.0 |
| 52 | .NA...ATT.N.M .ADDR............T ....DR Q.AKR.DTAVEE | 4 | 0.0 |
| 53 | ..AG..A.MKD.R T..SE....D.......T E..KD. ..ANGGDVAIGQ | 4 | 0.0 |
| 54 | S.PG...TIRD.K TVST.....D...P...T ...DDR ..SGRN.VAVEE | 4 | 0.0 |
| 55 | S.P...A.INT.R ..P.R............T E...GR QSA.KDDVDIGG | 4 | 0.0 |
| 56 | .N.G..AGLQK.M ..HGG........P...T ...DG. QSSRGNDVAV.D | 4 | 0.0 |
| 57 | .N.....TPRT.A .IPSH....E........ ...... Q.SNG..I.FGS | 4 | 0.0 |
| 58 | SNAG..AGLRQ.T .APAE....D.......T E..AG. ..GGGA.IAVEE | 4 | 0.0 |
| 59 | ..A...AAK.T.V .ISTR............T E..... ...SKNDV.VE. | 4 | 0.0 |
| 60 | .......TTR..M IYGG.............T E..AGR Q..ATA.V.VES | 4 | 0.0 |
| 61 | ..AG..AGMRE.A TIYTG............. ....GR ..SSTGD.DVGR | 4 | 0.0 |
| 62 | S..G..A.PKE.R TA..H....E.......T E...D. Q.AGE..VAI.G | 4 | 0.0 |
| 63 | .......GT.T.R ..DTG............. G....R ..AGTAD.AV.G | 4 | 0.0 |
| 64 | .NAG....KRD.. TAYTR....D.......T ...D.. Q..GKTD.DNGG | 4 | 0.0 |
| 65 | .NA....DMKH.T .ISDR........P...T R..N.R QS.RGG...I.G | 4 | 0.0 |
| 66 | SN.G..ADLRD.. TIPTQ....E........ ...NDR QSAK.NDV.V.R | 4 | 0.0 |
| 67 | S.A....ATQQ.V T.DSQ....E.......T R..NDR .NAEGG.V.IGQ | 4 | 0.0 |
| 68 | .NAG...ANKT.M .I.AH....E.......T R..DG. QDSS.D.I.YGK | 4 | 0.0 |
| 69 | .NAG...GTKE.R TI..E............T ...D.. .DAKRN.VDY.G | 4 | 0.0 |
| 70 | SNP....GK.S.K ..S.E............. ...NG. .DSR.GD.DFEK | 4 | 0.0 |
| 71 | .N....ASIRQ.Q ..PDG....K........ R..NGR ..S.EG.I.IEG | 4 | 0.0 |
| 72 | .N.G...TL.A.G TAHTQ............. R..ND. QSS.GGDTAF.G | 4 | 0.0 |
| 73 | SNP....TTQ..Q ..D......D...P...T R..TDR ..S.GGD..IER | 4 | 0.0 |
| 74 | SNA....TMRK.G TISSG........P.... G..N.. QDSSENDVADER | 4 | 0.0 |
| 75 | S.AG..ATMQ..M T.DTG............T R..N.R Q.GEGGDI.D.R | 4 | 0.0 |
| 76 | ..AG..ATTRD.Q T.DDH....D........ ...NGR Q.GRGA.TAYEG | 4 | 0.0 |
| 77 | ...G..AAM.A.R T.DDG....K...P.... ...... .DGGT...AIGD | 4 | 0.0 |
| 78 | .N.....TNRE.M .IP..............T R...D. .D.GRADV.VGR | 4 | 0.0 |
| 79 | SNAG..ADKQD.V TAHSE............. E..DDR Q.AAGGDI.VGS | 4 | 0.0 |
| 80 | .NA...AATHE.. T.HDH....D........ R..A.R ..GAK.DVDFGS | 4 | 0.0 |
| 81 | SNA...ADTRH.M T.PGE....D...P...T G..TG. Q.SATTDI.YGE | 4 | 0.0 |
| 82 | SN.....A..K.Q .IH.R....D.......T R..DDR Q.AEG.DVAVGD | 4 | 0.0 |
| 83 | .NP...AD.RA.Q .IPTG....D.......T R..T.. Q..GG.DI.IGG | 4 | 0.0 |
| 84 | SNA...AGLNA.K .AYTH....D.......T G..D.R .NAK.G..AI.G | 4 | 0.0 |
| 85 | .NP.....LQ..M .IDDQ........P...T ....D. .SGGTADVAV.K | 4 | 0.0 |
| 86 | ......ASIQ..Q ..YA.....E.......T ....D. .SAAG.DT.V.G | 4 | 0.0 |

Calculated plasmid library complexity based on colony count (2.5×10⁷) and NGS sequencing (0.94 of unique sequences) is 2.35×10⁷. WT AAV3 contamination is 0.02%.

Example 2

Q5 PCR:

50 µl: 10 µp 5×B Q5
    0.4 µl 25 mM dNTPs
    2.5 µl F
    2.5 µl R
    1 µl (1 ng) pITR3-R3C3-AatII
    0.5 µl Q5 Pol
    H₂O up to 50 µl

| | | |
|---|---|---|
| 98° C. | 30 sec | 30 cycles |
| 98° C. | 10 sec | |
| 65° C. | 20 sec | |
| 72° C. | 30 sec | |
| 72° C. | 2 min | |

Figure 6:
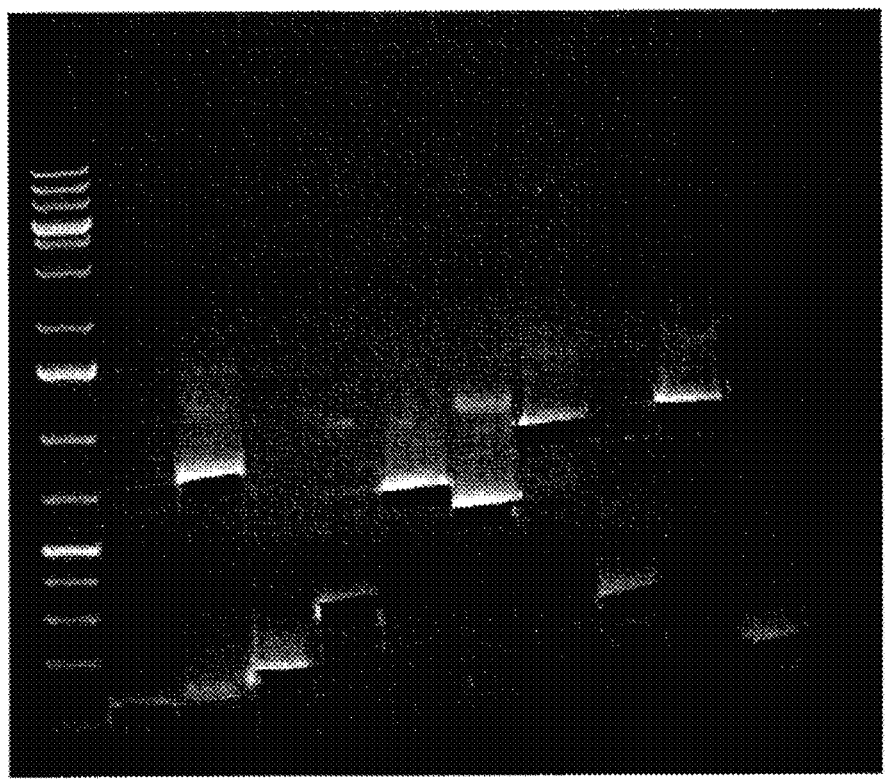
FIGS. 6-9 are photographs of agarose gels showing products of PCR reactions as per Example 2.

See FIG. 6.

TABLE 5

| Fragment | | Size (bp) | Conc. (µg/ml) | nM | µl/5 × 10⁹ copies |
|---|---|---|---|---|---|
| A | 1 | 86 | 10.4 | 186 | 2.2 |
| I + V + VI | 2 | 747 | 33.3 | 69 | 6 |
| | 3 | 136 | 13.2 | 149 | 2.8 |
| | 4 | 281 | 35.4 | 194 | 2.1 |
| B | 5 | 647 | 48 | 114 | 3.6 |
| IV | 6 | 556 | 29.4 | 81 | 5.1 |
| C | 7 | 935 | 22.5 | 37 | 11.2 |
| VII | 8 | 266 | 11.2 | 65 | 6.4 |
| D | 9 | 1055 | 38.8 | 57 | 7.3 |
| VIII | 10 | 147 | 35.9 | 376 | 1.1 |

TABLE 6

| | OE Q5 PCR | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 5xB | dNTP | A3CL-F | A3CL-R | Q5 | H₂O |
| A | 2.2 | 6 | 2.8 | 2.1 | | | | | | | 10 | 0.4 | 2.5 | 2.5 | 0.5 | 26 |
| B | | | | | 3.6 | 5.1 | | | | | 10 | 0.4 | 2.5 | 2.5 | 0.5 | 30.4 |
| C | | | | | | | 11.2 | 6.4 | | | 10 | 0.4 | 2.5 | 2.5 | 0.5 | 21.5 |
| D | | | | | | | | | 7.3 | 1.1 | 10 | 0.4 | 2.5 | 2.5 | 0.5 | 30.7 |

1. Assays A, B, C, and D are assembled without primers, substituting H₂O for the primers' volumes (5 µl) and subjected to the following overlap extension:

| | | |
|---|---|---|
| 98° C. | 30 sec | 15 cycles |
| 98° C. | 10 sec | |
| 65° C. | 20 sec | |
| 72° C. | 60 sec | |
| 72° C. | 2 min | |

2. 40 µl each A, B, C, and D from Step 1 transferred to 10 µl containing:

| | X5 |
|---|---|
| 2.5 µl A3CL-F | 12.5 |
| 2.5 µl A3CL-R | 12.5 |
| 2 µl 5 × B Q5 | 10 |
| 0.08 µl dNTPs | 0.4 |
| 0.1 µl Q5 | 0.5 |
| 2.82 µl H₂O | 14.1 |

Assays are subjected to the following PCRs:

| | | |
|---|---|---|
| 98° C. | 30 sec | 20 cycles |
| 98° C. | 10 sec | |
| 59° C. | 20 sec | |
| 72° C. | 60 sec | |
| 72° C. | 2 min | |

Figure 7:
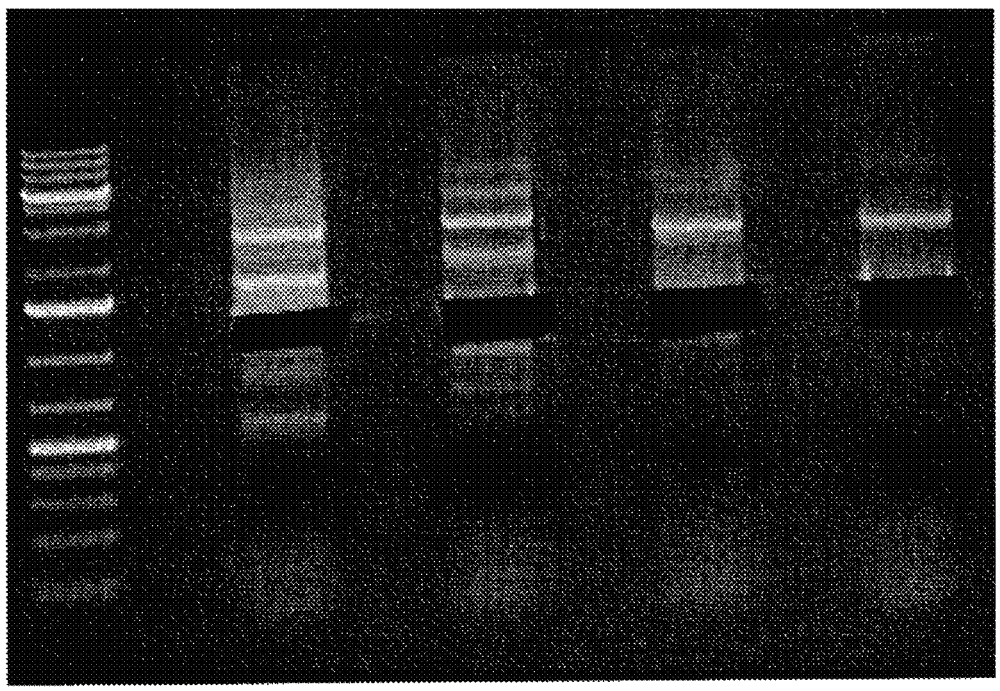

See FIG. 7: Eluted in 50 µl each A, B, C, or D; pTR3-R3C3-AatII/AatII+ApaI eluted in 75 µl.

TABLE 7

|   | Size (bp) | Conc. (ng/μl) | Molarity (nM) | Conc. (pmoles/μl) | μl/40 μl assay | pmoles/40 μl assay (3:1) |
|---|---|---|---|---|---|---|
| A | 1091 | 47.5 | 67 | 0.067 | 2.1 (100 ng) | 0.144 |
| B | 1091 | 58.3 | 82 | 0.082 | 1.8 (100 ng) | 0.144 |
| C | 1091 | 49.9 | 70 | 0.07 | 2.1 (100 ng) | 0.144 |
| D | 1091 | 60.9 | 86 | 0.086 | 1.7 (100 ng) | 0.144 |
| pITR3-R3C3-AatII AatII-ApaI cut | 6594 | 54.3 | 13 | 0.013 | 3.7 (200 ng) | 0.048 |

| 40 μl assay: | | | | | | |
|---|---|---|---|---|---|---|
| 20 μl 2xGibson Master Mix (NEB) + | | | | | | |
| A | B | C | D | pITR3 | H$_2$O | |
| 2.1 |   |   |   | 3.7 | 14.2 | A |
|   | 1.8 |   |   | 3.7 | 14.5 | B |
|   |   | 2.1 |   | 3.7 | 14.2 | C |
|   |   |   | 1.7 | 3.7 | 14.6 | D |

Large-Scale IDA for the Loop A

300 μl assay: 150 μl 2xGibson Master Mix 27.6 μl pITR3-R3C3-AatII AatII-ApaI cut (1.5 μg)

15.8 μl A (0.75 μg)

106.6 μl H$_2$O

Incubated 2 h, 50° C., Zymo-purified, eluted in 100 μl H$_2$O, combined with 47.5 μl of A from the pilot IDA above. Total—1.7 μg of vector plasmid DNA.

Lucigen competent cells were prepared from 4 L LB, resuspended in 8.5 ml H$_2$O final volume. The cell density (10 μl in 3 ml H$_2$O) was A$_{550}$=0.79.

Combined DNA (147.5 μl) was mixed with the whole volume of competent cells and aliquoted (385 μl/aliquot, ~10 ng plasmid DNA/50 μl competent cells) into electroporation cuvettes (total of ~20, with outside tall electrodes) and zapped at 2.9 KV.

Cells were transferred into 1 L LB, incubated shaking at 37° C. for 1 h. Carbenicillin was added up 100 μg/ml, cell were grown at 30° C., o/n.

Total complexity from the large-scale IDA/transformation is $4.4 \times 10^7$ clones.

Repeat IDA for the Loop C

100 μl assay: 50 μl 2xGibson Master Mix 9.25 μl pITR3-R3C3-AatII AatII-ApaI cut (0.5 μg)

5.25 μl C (0.25 μg)

35.5 μl H$_2$O

Zymo, 50 μl H$_2$O.

Competent cells were prepared from 4 L LB (grown to A$_{550}$=0.6) and resuspended in a final volume 8 ml H$_2$O. The cell density (10 μl in 3 ml H$_2$O) was A$_{550}$=1.46.

180 ng vector with fragment B from the pilot IDA were electroporated with 1 ml of comp. cells, whereas 0.68 μg with fragment C—with 3 ml of cells.

After electroporation the complexity of B was ~$1.7 \times 10^7$ (~5 times over theoretical complexity), while C ~$1 \times 10^8$ (~2.5 times over theoretical complexity).

TABLE 8

|   | Pilot | | | | Large-scale | | | |
|---|---|---|---|---|---|---|---|---|
|   | A | B | C | D | A | B | C | D |
| Complexity total | $0.9 \times 10^5$ | $0.7 \times 10^5$ | $1.4 \times 10^5$ | $0.9 \times 10^5$ | $4.4 \times 10^7$ | $1.7 \times 10^7$ | $1 \times 10^8$ | $1 \times 10^8$ |
| Volume (μl) | 400 | 400 | 400 | 400 | 1000 | 100 | 500 | 1000 |
| Complexity/μl | 225 | 175 | 525 | 225 | $4.4 \times 10^4$ | $1.7 \times 10^5$ | $2 \times 10^5$ | $10^5$ |
| DNA concentration (ng/μl) | 342 | 220 | 241 | 334 | 1690 | 1100 | 2100 | 2000 |
| Copies/μl | $4.2 \times 10^{10}$ | $2.6 \times 10^{10}$ | $2.9 \times 10^{10}$ | $4 \times 10^{10}$ | $2 \times 10^{11}$ | $1.3 \times 10^{11}$ | $2.5 \times 10^{11}$ | $2.4 \times 10^{11}$ |
| Representation (copies/variant/μl) | $1.9 \times 10^8$ | $1.5 \times 10^8$ | $0.6 \times 10^8$ | $1.8 \times 10^8$ | $4.5 \times 10^6$ | $7.6 \times 10^5$ | $1.3 \times 10^6$ | $2.4 \times 10^6$ |
| Dilution factor | 42.2 | 197.4 | 46.2 | 75 | | | | |
| Final DNA concentration after mixing equal volumes (μg/μl) | | | | | | 0.55 | 1.1 | 1 |
| Viral DNA concentration, 80 μl (μg/ml) | | | | | 27.6 | 22.8 | 23.2 | 85.5 |
| Titer (copies/μl) | | | | | | $4.5 \times 10^9$ | $4.6 \times 10^9$ | $1.6 \times 10^{10}$ |

Q5 PCR of Viral DNA

Conditions, as above, except: 50 ng viral DNA/50 μl assay, 20 PCR cycles

5 μl out of 50

1. Loop I, primers A3CL-F+VR-I_IV-R, template A, size 644 bp
2. Loop IV, primers VR-I_IV-F+VR-IV_V-R, template B, size 145 bp
3. Loops V+VI, primers VR-IV_V-F+VR-VI_VII-R, tempi A, size 194 bp 4. Loop VII, primers VR-VI_VR-VII-F+A3CL-R, template C, size 274 bp Remaining 45 µl were purified using preparative gel, all four gel cutouts were pooled in one tube and purified using one column, final volume 50 µl H$_2$O.

Figure 8:
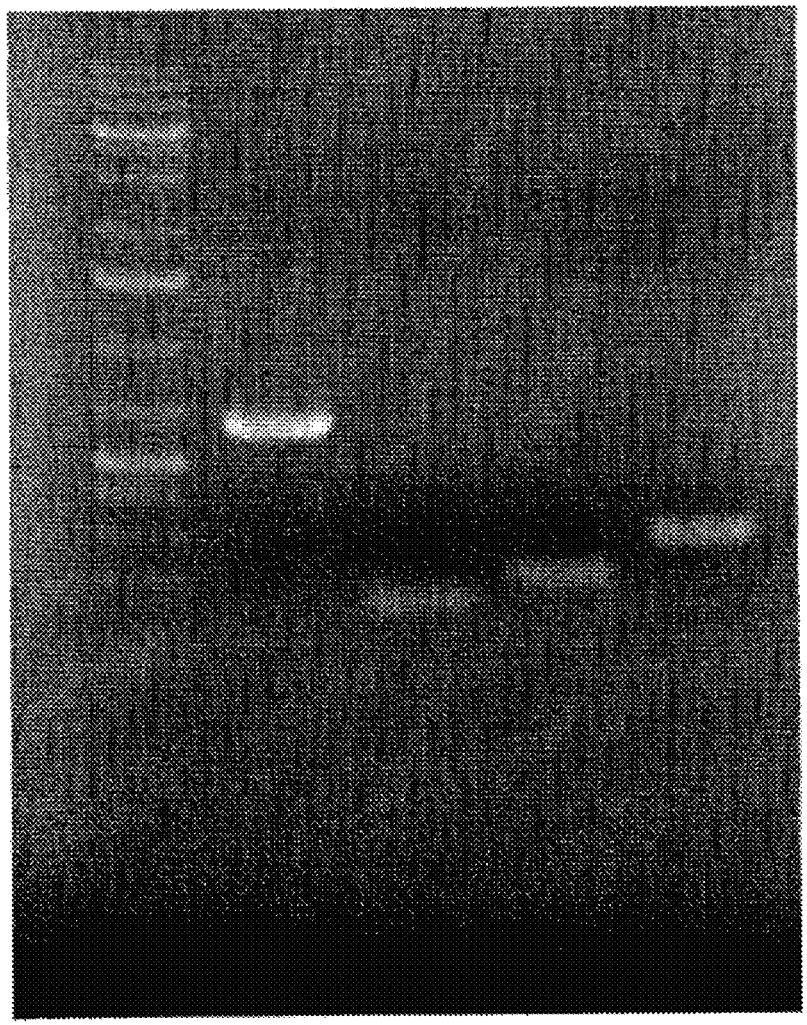

See FIG. 8.

Overlap Extension

Full-length fragment was assembled without primers, substituting H$_2$O for the primers' volumes (5 µl) and subjected to the following overlap extension:

50 µl: 10 µl 5×B Q5
    0.4 µl 25 mM dNTPs
    25 µl (out of 50 µl) individual overlap 4 fragments mix (p. 12)
    0.5 µl Q5 Pol
    14.1 µl H$_2$O

| | | |
|---|---|---|
| 98° C. | 30 sec | 15 cycles |
| 98° C. | 10 sec | |
| 65° C. | 20 sec | |
| 72° C. | 60 sec | |
| 72° C. | 2 min | |

After primer-less extension, the assay was split into 2×25 µl assays supplemented with A3CL-F, and A3CL-R primers, DNTPs, and fresh Q5, total volume 50 µl each.

Assays are subjected to the following PCRs:

| | | |
|---|---|---|
| 98° C. | 30 sec | 20 cycles |
| 98° C. | 10 sec | |
| 59° C. | 20 sec | |
| 72° C. | 60 sec | |
| 72° C. | 2 min | |

ABC fragment was eluted in 50 µl, concentration 60 ng/µl (0.085 pmoles/µl).

D fragment was eluted in 50 µl, concentration 46 ng/µl (0.065 pmoles/µl).

Figure 9:
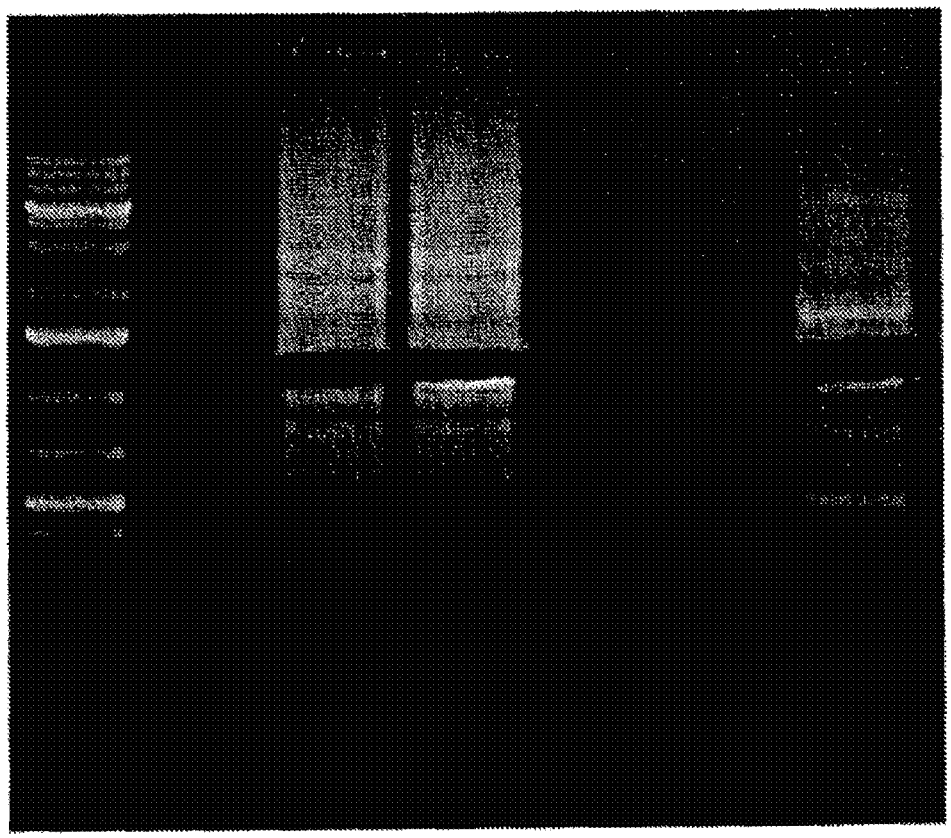

See FIG. 9.

IDA Using NE Builder Master Mix
    Total volume—200 µl, plasmid 1.5 µg (0.348 pmoles), insert—0.5 µg (0.7 pmoles), total DNA amount ~1 pmole/200 µl assay.
    Reaction 60 min @ 50° C. Lucigen electrocompetent E. coli cells, 8 ml, final density 0.8 A550. Library's complexity 2.5×10$^7$.

SEQUENCE LISTING

```
<160> NUMBER OF SEQ ID NOS: 142

<210> SEQ ID NO 1
<211> LENGTH: 1085
<212> TYPE: DNA
<213> ORGANISM: Parvo-like virus
<220> FEATURE:
<221> NAME/KEY: misc_feature
<222> LOCATION: (611)..(611)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t

<400> SEQUENCE: 1
tgcccactta caacaaccat ctctacaagc aaatctccag cvvmdcagga gctascaacg      60
acaaccacta ctttggctac agcacccctt gggggtattt tgactttaac agattccact     120
gccacttctc accacgtgac tggcagcgac tcattaacaa caactgggga ttccggccca     180
agaaactcag cttcaagctc ttcaacatcc aagttagagg ggtcacgcag aacgatggca     240
cgacgactat tgccaataac cttaccagca cggttcaagt gtttacggac tcggagtatc     300
agctcccgta cgtgctcggg tcggcgcacc aaggctgtct cccgccgttt ccagcggacg     360
tcttcatggt ccctcagtat ggatacctca ccctgaacaa cggaagtcaa gcggtgggac     420
gctcatcctt ttactgcctg gagtacttcc cttcgcagat gctaaggact ggaaataact     480
tccaattcag ctataccttc gaggatgtac cttttcacag cagctacgct cacagccaga     540
gtttggatcg cttgatgaat cctcttattg atcagtatct gtactacctg aacagaacgc     600
aargcamcvc nrgcggaaca rccrvcmhsm rsvvsctgvn gtttagccag gctgggcctc     660
agtctatgtc tttgcaggcc agaaattggc tacctgggcc ctgctaccgg caacagagac     720
tttcaamary cbmcrvcsrs aacaacaaca gtrasttcc ttggmcagcg gccagcamat     780
```

```
atcatctcaa tggccgcgac tcgctggtga atccaggacc agctatggcc agtcacrrgg    840
acgatrmsgr sarattttc cctatgcacg gcaatctaat atttggcaaa saarrcrscr     900
vsrvarvcra trycgmsdwc grsvrsgtaa tgattacgga tgaagaagag attcgtacca    960
ccaatcctgt ggcaacagag cagtatggaa ctgtggcaaa taacttgcag rvsvvsmrsr   1020
vcvvscccac gdhtvvsrns gtcvmscatc aggggggcctt acctggcatg gtgtggcaag  1080
atcgt                                                               1085

<210> SEQ ID NO 2
<211> LENGTH: 620
<212> TYPE: PRT
<213> ORGANISM: Parvo-like virus
<220> FEATURE:
<221> NAME/KEY: misc_feature
<222> LOCATION: (263)..(264)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (450)..(453)
<223> OTHER INFORMATION: Xaa can be any naturally occurring amino acid
<220> FEATURE:
<221> NAME/KEY: misc_feature
<222> LOCATION: (456)..(460)
<223> OTHER INFORMATION: Xaa can be any naturally occurring amino acid
<220> FEATURE:
<221> NAME/KEY: misc_feature
<222> LOCATION: (462)..(462)
<223> OTHER INFORMATION: Xaa can be any naturally occurring amino acid
<220> FEATURE:
<221> NAME/KEY: misc_feature
<222> LOCATION: (491)..(495)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid
<220> FEATURE:
<221> NAME/KEY: misc_feature
<222> LOCATION: (504)..(504)
<223> OTHER INFORMATION: Xaa can be any naturally occurring amino acid
<220> FEATURE:
<221> NAME/KEY: misc_feature
<222> LOCATION: (508)..(508)
<223> OTHER INFORMATION: Xaa can be any naturally occurring amino acid
<220> FEATURE:
<221> NAME/KEY: misc_feature
<222> LOCATION: (528)..(528)
<223> OTHER INFORMATION: Xaa can be any naturally occurring amino acid
<220> FEATURE:
<221> NAME/KEY: misc_feature
<222> LOCATION: (531)..(533)
<223> OTHER INFORMATION: Xaa can be any naturally occurring amino acid
<220> FEATURE:
<221> NAME/KEY: misc_feature
<222> LOCATION: (546)..(557)
<223> OTHER INFORMATION: Xaa can be any naturally occurring amino acid
<220> FEATURE:
<221> NAME/KEY: misc_feature
<222> LOCATION: (586)..(590)
<223> OTHER INFORMATION: Xaa can be any naturally occurring amino acid
<220> FEATURE:
<221> NAME/KEY: misc_feature
<222> LOCATION: (593)..(595)
<223> OTHER INFORMATION: Xaa can be any naturally occurring amino acid
<220> FEATURE:
<221> NAME/KEY: misc_feature
<222> LOCATION: (597)..(597)
<223> OTHER INFORMATION: Xaa can be any naturally occurring amino acid

<400> SEQUENCE: 2
```

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Ile Leu Glu Pro
            115                 120                 125

Leu Gly Leu Val Glu Glu Ala Ala Lys Thr Ala Pro Gly Lys Lys Gly
        130                 135                 140

Ala Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Xaa Xaa Gly Ala Xaa Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
        290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415
```

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Leu Asn Arg Thr
        435                 440                 445

Gln Xaa Xaa Xaa Gly Thr Xaa Xaa Xaa Xaa Xaa Leu Xaa Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Xaa Xaa Xaa Xaa Asn
                485                 490                 495

Asn Asn Ser Xaa Phe Pro Trp Xaa Ala Ala Ser Xaa Tyr His Leu Asn
            500                 505                 510

Gly Arg Asp Ser Leu Val Asn Pro Gly Pro Ala Met Ala Ser His Xaa
        515                 520                 525

Asp Asp Xaa Xaa Xaa Phe Phe Pro Met His Gly Asn Leu Ile Phe Gly
        530                 535                 540

Lys Xaa Xaa Xaa Xaa Xaa Xaa Xaa Xaa Xaa Xaa Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Xaa Xaa Xaa Xaa Pro Thr
        580                 585                 590

Xaa Xaa Xaa Val Xaa His Gln Gly Ala Leu Pro Gly Met Val Trp Gln
    595                 600                 605

Asp Arg Asp Val Tyr Leu Gln Gly Pro Ile Trp Ala
610                 615                 620

<210> SEQ ID NO 3
<211> LENGTH: 1491
<212> TYPE: DNA
<213> ORGANISM: Parvo-like virus

<400> SEQUENCE: 3
accaccagca ccagaacctg ggccctgccc acttacaaca accatctcta caagcaaatc        60
tccagccaat caggagcttc aaacgacaac cactactttg ctacagcac cccttggggg       120 tattttgact ttaacagatt ccactgccac ttctcaccac gtgactggca gcgactcatt       180
aacaacaact ggggattccg gcccaagaaa ctcagcttca agctcttcaa catccaagtt       240 agagggtca cgcagaacga tggcacgacg actattgcca ataaccttac cagcacggtt       300
caagtgttta cggactcgga gtatcagctc ccgtacgtgc tcgggtcggc gccaccaagc       360
tgtctcccgc cgtttccagc ggacgtcttc atggtccctc agtatggata cctcaccctg       420
aacaacggaa gtcaagcgt gggacgctca tccttttact gcctggagta cttcccttcg       480
cagatgctaa ggactggaaa taacttccaa ttcagctata ccttcgagga tgtacctttt       540
cacagcagct acgctcacag ccagagtttg atcgcttga tgaatcctct tattgatcag       600
tatctgtact acctgaacag aacgcaagga acaacctctg aacaaccaa ccaatcacgg       660 ctgctttta gccaggctgg gcctcagtct atgtctttgc aggccagaaa ttggctacct       720
gggccctgct accggcaaca gagactttca agactgcta cgacaacaa caacagtaac       780 tttccttgga cagcggccag caaatatcat ctcaatggcc gcgactcgct ggtgaatcca       840
ggaccagcta tggccagtca caggacgat gaagaaaaat tttcccctat gcacggcaat       900
ctaatatttg gcaagaagg gacaacggca agtaacgcag aattagataa tgtaatgatt       960

```
acggatgaag aagagattcg taccaccaat cctgtggcaa cagagcagta tggaactgtg    1020
gcaaataact tgcagagctc aaatacagct cccacgactg aactgtcaa tcatcagggg     1080 gccttacctg gcatggtgtg gcaagatcgt gacgtctacc ttcaaggacc tatctgggca    1140
aagattcctc acacggatgg acactttcat ccttctcctc tgatgggagg ctttggactg    1200
aaacatccgc tcctcaaat catgatcaaa atactccgg taccggcaaa tcctccgacg      1260
actttcagcc cggccaagtt tgcttcattt atcactcagt actccactgg acaggtcagc    1320
gtggaaattg agtgggagct acagaaagaa aacagcaaac gttggaatcc agagattcag    1380
tacacttcca actacaacaa gtctgttaat gtggacttta ctgtagacac taatggtgtt    1440
tatagtgaac ctcgccctat tggaacccgg tatctcacac gaaacttgtg a             1491
```

<210> SEQ ID NO 4
<211> LENGTH: 496
<212> TYPE: PRT
<213> ORGANISM: Parvo-like virus

<400> SEQUENCE: 4

```
Thr Thr Ser Thr Arg Thr Trp Ala Leu Pro Thr Tyr Asn Asn His Leu
1               5                   10                  15

Tyr Lys Gln Ile Ser Ser Gln Ser Gly Ala Ser Asn Asp Asn His Tyr
            20                  25                  30

Phe Gly Tyr Ser Thr Pro Trp Gly Tyr Phe Asp Phe Asn Arg Phe His
        35                  40                  45

Cys His Phe Ser Pro Arg Asp Trp Gln Arg Leu Ile Asn Asn Asn Trp
    50                  55                  60

Gly Phe Arg Pro Lys Lys Leu Ser Phe Lys Leu Phe Asn Ile Gln Val
65                  70                  75                  80

Arg Gly Val Thr Gln Asn Asp Gly Thr Thr Thr Ile Ala Asn Asn Leu
                85                  90                  95

Thr Ser Thr Val Gln Val Phe Thr Asp Ser Glu Tyr Gln Leu Pro Tyr
            100                 105                 110

Val Leu Gly Ser Ala His Gln Gly Cys Leu Pro Pro Phe Pro Ala Asp
        115                 120                 125

Val Phe Met Val Pro Gln Tyr Gly Tyr Leu Thr Leu Asn Asn Gly Ser
    130                 135                 140

Gln Ala Val Gly Arg Ser Ser Phe Tyr Cys Leu Glu Tyr Phe Pro Ser
145                 150                 155                 160

Gln Met Leu Arg Thr Gly Asn Asn Phe Gln Phe Ser Tyr Thr Phe Glu
                165                 170                 175

Asp Val Pro Phe His Ser Ser Tyr Ala His Ser Gln Ser Leu Asp Arg
            180                 185                 190

Leu Met Asn Pro Leu Ile Asp Gln Tyr Leu Tyr Tyr Leu Asn Arg Thr
        195                 200                 205

Gln Gly Thr Thr Ser Gly Thr Thr Asn Gln Ser Arg Leu Leu Phe Ser
    210                 215                 220

Gln Ala Gly Pro Gln Ser Met Ser Leu Gln Ala Arg Asn Trp Leu Pro
225                 230                 235                 240

Gly Pro Cys Tyr Arg Gln Gln Arg Leu Ser Lys Thr Ala Asn Asp Asn
                245                 250                 255

Asn Asn Ser Asn Phe Pro Trp Thr Ala Ala Ser Lys Tyr His Leu Asn
            260                 265                 270

Gly Arg Asp Ser Leu Val Asn Pro Gly Pro Ala Met Ala Ser His Lys
        275                 280                 285
```

```
Asp Asp Glu Glu Lys Phe Phe Pro Met His Gly Asn Leu Ile Phe Gly
        290                 295                 300

Lys Glu Gly Thr Thr Ala Ser Asn Ala Glu Leu Asp Asn Val Met Ile
305                 310                 315                 320

Thr Asp Glu Glu Ile Arg Thr Thr Asn Pro Val Ala Thr Glu Gln
            325                 330                 335

Tyr Gly Thr Val Ala Asn Asn Leu Gln Ser Ser Asn Thr Ala Pro Thr
                340                 345                 350

Thr Gly Thr Val Asn His Gln Gly Ala Leu Pro Gly Met Val Trp Gln
        355                 360                 365

Asp Arg Asp Val Tyr Leu Gln Gly Pro Ile Trp Ala Lys Ile Pro His
    370                 375                 380

Thr Asp Gly His Phe His Pro Ser Pro Leu Met Gly Gly Phe Gly Leu
385                 390                 395                 400

Lys His Pro Pro Pro Gln Ile Met Ile Lys Asn Thr Pro Val Pro Ala
                405                 410                 415

Asn Pro Pro Thr Thr Phe Ser Pro Ala Lys Phe Ala Ser Phe Ile Thr
                420                 425                 430

Gln Tyr Ser Thr Gly Gln Val Ser Val Glu Ile Glu Trp Glu Leu Gln
        435                 440                 445

Lys Glu Asn Ser Lys Arg Trp Asn Pro Glu Ile Gln Tyr Thr Ser Asn
450                 455                 460

Tyr Asn Lys Ser Val Asn Val Asp Phe Thr Val Asp Thr Asn Gly Val
465                 470                 475                 480

Tyr Ser Glu Pro Arg Pro Ile Gly Thr Arg Tyr Leu Thr Arg Asn Leu
                485                 490                 495

<210> SEQ ID NO 5
<211> LENGTH: 1140
<212> TYPE: DNA
<213> ORGANISM: Parvo-like virus
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (1064)..(1064)
<223> OTHER INFORMATION: n is a, c, g, or t

<400> SEQUENCE: 5
accaccagca ccagaacctg ggccctgccc acttacaaca accatctcta caagcaaatc      60
tccagcvvmd caggagctas caacgacaac cactactttg gctacagcac cccttggggg     120
tattttgact ttaacagatt ccactgccac ttctcaccac gtgactggca gcgactcatt     180
aacaacaact ggggattccg gcccaagaaa ctcagcttca gctcttcaa catccaagtt      240 agagggtca cgcagaacga tggcacgacg actattgcca ataaccttac cagcacggtt      300
caagtgttta cggactcgga gtatcagctc ccgtacgtgc tcgggtcggc gcaccaaggc     360
tgtctcccgc cgtttccagc ggacgtcttc atggtccctc agtatggata cctcaccctg     420
aacaacggaa gtcaagcggt gggacgctca tccttttact gcctggagta cttcccttcg     480
cagatgctaa ggactggaaa taacttccaa ttcagctata ccttcgagga tgtacccttt     540
cacagcagct acgctcacag ccagagtttg gatcgcttga tgaatcctct tattgatcag     600
```

```
tatctgtact acctgaacag aacgcaargc amcvcnrgcg gaacarccrv cmhsmrsvvs    660
ctgvngttta gccaggctgg gcctcagtct atgtctttgc aggccagaaa ttggctacct    720
gggccctgct accggcaaca gagactttca amarycbmcr vcsrsaacaa caacagtras    780
tttccttggm cagcggccag camatatcat ctcaatggcc gcgactcgct ggtgaatcca    840
ggaccagcta tggccagtca crrggacgat rmsgrsarat ttttccctat gcacggcaat    900
ctaatatttg gcaaasaarr crscrvsrva rvcratrycg msdwcgrsvr sgtaatgatt    960
acggatgaag aagagattcg taccaccaat cctgtggcaa cagagcagta tggaactgtg   1020
gcaaataact tgcagrvsvv smrsrvcvvs cccacgdhtv vsrnsgtcvm scatcagggg   1080
gccttacctg gcatggtgtg gcaagatcgt gacgtctacc ttcaaggacc tatctgggca   1140
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ggctgggcga cagagtcatc                                                 20

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
gctggagatt tgcttgtaga gatg                                            24

<210> SEQ ID NO 8
<211> LENGTH: 60
<212> TYPE: DNA
<213> ORGANISM: Artificial Sequence
<220> FEATURE:
<223> OTHER INFORMATION: Synthetic

<400> SEQUENCE: 8
catctctaca agcaaatctc cagcvvmdca ggagctasca acgacaacca ctactttggc    60

<210> SEQ ID NO 9
<211> LENGTH: 56
<212> TYPE: DNA
<213> ORGANISM: Artificial Sequence
<220> FEATURE:
<223> OTHER INFORMATION: Synthetic

<400> SEQUENCE: 9
ccaaggaaas tyactgttgt tgttsysgby gkvgrytktt gaaagtctct gttgcc        56

<210> SEQ ID NO 10
<211> LENGTH: 52
<212> TYPE: DNA
<213> ORGANISM: Artificial Sequence
<220> FEATURE:
<223> OTHER INFORMATION: Synthetic

<400> SEQUENCE: 10
aacaacaaca gtrastttcc ttggmcagcg gccagcamat atcatctcaa tg            52
```

<210> SEQ ID NO 11
<211> LENGTH: 58
<212> TYPE: DNA
<213> ORGANISM: Artificial Sequence
<220> FEATURE:
<223> OTHER INFORMATION: Synthetic

<400> SEQUENCE: 11
gattgccgtg catagggaaa aatytsycsk yatcgtccyy gtgactggcc atagctgg        58

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12
atttttccct atgcacggca atc        23

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
catccgtgtg aggaatcttt gc        22

<210> SEQ ID NO 14
<211> LENGTH: 25
<212> TYPE: DNA
<213> ORGANISM: Artificial Sequence
<220> FEATURE:
<223> OTHER INFORMATION: Synthetic

<400> SEQUENCE: 14
ttgcgttctg ttcaggtagt acaga        25

<210> SEQ ID NO 15
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t

<400> SEQUENCE: 15
ctgtactacc tgaacagaac gcaargcamc vcnrgcggaa carccrvcmh smrsvvsctg        60
vngtttagcc aggctgggcc        80

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16

```
tttgccaaat attagattgc c                                              21

<210> SEQ ID NO 17
<211> LENGTH: 80
<212> TYPE: DNA
<213> ORGANISM: Artificial Sequence
<220> FEATURE:
<223> OTHER INFORMATION: Synthetic

<400> SEQUENCE: 17
cggcaatcta atatttggca aasaarrcrs crvsrvarvc ratrycgmsd wcgrsvrsgt     60
aatgattacg gatgaagaag                                                80

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
ctgcaagtta tttgccacag ttc                                            23

<210> SEQ ID NO 19
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (52)..(52)
<223> OTHER INFORMATION: n is a, c, g, or t

<400> SEQUENCE: 19
gaactgtggc aaataacttg cagrvsvvsm rsrvcvvscc cacgdhtvvs rnsgtcvmsc     60 atcaggggc cttacctg                                                   78

<210> SEQ ID NO 20
<211> LENGTH: 28
<212> TYPE: DNA
<213> ORGANISM: Artificial Sequence
<220> FEATURE:
<223> OTHER INFORMATION: Synthetic

<400> SEQUENCE: 20
cagtatctgt actacctgaa cagaacgc                                       28

<210> SEQ ID NO 21
<211> LENGTH: 28
<212> TYPE: DNA
<213> ORGANISM: Artificial Sequence
<220> FEATURE:
<223> OTHER INFORMATION: Synthetic

<400> SEQUENCE: 21
gcgttctgtt caggtagtac agatactg                                       28

<210> SEQ ID NO 22
<211> LENGTH: 26
<212> TYPE: DNA
<213> ORGANISM: Artificial Sequence
<220> FEATURE:
<223> OTHER INFORMATION: Synthetic
```

<400> SEQUENCE: 22
cctgggccct gctaccggca acagag					26

<210> SEQ ID NO 23
<211> LENGTH: 26
<212> TYPE: DNA
<213> ORGANISM: Artificial Sequence
<220> FEATURE:
<223> OTHER INFORMATION: Synthetic

<400> SEQUENCE: 23
ctctgttgcc ggtagcaggg cccagg					26

<210> SEQ ID NO 24
<211> LENGTH: 28
<212> TYPE: DNA
<213> ORGANISM: Artificial Sequence
<220> FEATURE:
<223> OTHER INFORMATION: Synthetic

<400> SEQUENCE: 24
ccctatgcac ggcaatctaa tatttggc					28

<210> SEQ ID NO 25
<211> LENGTH: 28
<212> TYPE: DNA
<213> ORGANISM: Artificial Sequence
<220> FEATURE:
<223> OTHER INFORMATION: Synthetic

<400> SEQUENCE: 25
gccaaatatt agattgccgt gcataggg					28

<210> SEQ ID NO 26
<211> LENGTH: 49
<212> TYPE: PRT
<213> ORGANISM: Artificial Sequence
<220> FEATURE:
<223> OTHER INFORMATION: Synthetic

<400> SEQUENCE: 26

Gly Thr Thr Ser Gly Thr Thr Asn Gln Ser Arg Leu Leu Lys Thr Ala
1               5                   10                  15

Asn Asp Asn Asn Asn Ser Asn Phe Pro Trp Thr Ala Ala Ser Lys Lys
            20                  25                  30

Asp Asp Glu Glu Lys Glu Gly Thr Thr Ala Ser Asn Ala Glu Leu Asp
        35                  40                  45

Asn

<210> SEQ ID NO 27
<211> LENGTH: 49
<212> TYPE: PRT
<213> ORGANISM: Artificial Sequence
<220> FEATURE:
<223> OTHER INFORMATION: Synthetic

<400> SEQUENCE: 27

Gly Thr Thr Ser Gly Thr Thr Asn Gln Ser Arg Leu Leu Lys Thr Ala
1               5                   10                  15

Asn Asp Asn Asn Asn Ser Asn Phe Pro Trp Thr Ala Ala Ser Lys Lys
            20                  25                  30

Asp Asp Glu Glu Lys Glu Gly Thr Thr Ala Ser Asn Ala Glu Leu Asp
        35                  40                  45

Asn

<210> SEQ ID NO 28
<211> LENGTH: 49
<212> TYPE: PRT
<213> ORGANISM: Artificial Sequence
<220> FEATURE:
<223> OTHER INFORMATION: Synthetic

<400> SEQUENCE: 28

Gly Asn Thr Gly Gly Thr Thr Ser Pro Ser Arg Leu Arg Lys Ile Tyr
1               5                   10                  15

Asp Arg Asn Asn Asn Ser Asn Phe Pro Trp Thr Ala Ala Ser Thr Gly
            20                  25                  30

Asp Asp Thr Gly Arg Gln Gly Thr Gly Glu Gly Asn Val Glu Val Gly
        35                  40                  45

Lys

<210> SEQ ID NO 29
<211> LENGTH: 49
<212> TYPE: PRT
<213> ORGANISM: Artificial Sequence
<220> FEATURE:
<223> OTHER INFORMATION: Synthetic

<400> SEQUENCE: 29

Ser Thr Thr Ser Gly Thr Thr Gly Gln Arg Lys Leu Ala Lys Ala Tyr
1               5                   10                  15

Gly His Asn Asn Asn Ser Asp Phe Pro Trp Pro Ala Ala Ser Thr Gly
            20                  25                  30

Asp Asp Glu Asp Arg Gln Asp Ser Gly Glu Asn Asp Val Ala Ile Gly
        35                  40                  45

Arg

<210> SEQ ID NO 30
<211> LENGTH: 49
<212> TYPE: PRT
<213> ORGANISM: Artificial Sequence
<220> FEATURE:
<223> OTHER INFORMATION: Synthetic

<400> SEQUENCE: 30

Gly Thr Ala Ser Gly Thr Thr Ala Asn Ser Asn Leu Lys Lys Thr Tyr
1               5                   10                  15

Ser Asp Asn Asn Asn Ser Asn Phe Pro Trp Thr Ala Ala Ser Lys Gly
            20                  25                  30

Asp Asp Asp Asp Arg Glu Gly Thr Asp Gly Ala Asn Val Glu Ile Asp
        35                  40                  45

Arg

<210> SEQ ID NO 31
<211> LENGTH: 49
<212> TYPE: PRT
<213> ORGANISM: Artificial Sequence
<220> FEATURE:
<223> OTHER INFORMATION: Synthetic

<400> SEQUENCE: 31

Gly Thr Pro Ser Gly Thr Ala Ala His Lys Thr Leu Glu Lys Thr Ser
1               5                   10                  15

Ala Glu Asn Asn Asn Ser Asn Phe Pro Trp Thr Ala Ala Ser Lys Gly
            20                  25                  30

Asp Asp Ala Gly Arg Glu Asp Ala Glu Gly Gly Asp Ala Ala Ile Gly
        35                  40                  45

Gly

<210> SEQ ID NO 32
<211> LENGTH: 49
<212> TYPE: PRT
<213> ORGANISM: Artificial Sequence
<220> FEATURE:
<223> OTHER INFORMATION: Synthetic

<400> SEQUENCE: 32

Ser Thr Ala Gly Gly Thr Ala Thr Gln Lys Ala Leu Thr Lys Val His
1               5                   10                  15

Ala His Asn Asn Asn Ser Asn Phe Pro Trp Thr Ala Ala Ser Lys Glu
            20                  25                  30

Asp Asp Thr Gly Arg Gln Asp Ala Thr Arg Ser Asn Val Ala Phe Glu
        35                  40                  45

Glu

<210> SEQ ID NO 33
<211> LENGTH: 49
<212> TYPE: PRT
<213> ORGANISM: Artificial Sequence
<220> FEATURE:
<223> OTHER INFORMATION: Synthetic

<400> SEQUENCE: 33

Gly Asn Pro Ser Gly Thr Thr Gly Leu Arg Gly Leu Thr Thr Thr Asp
1               5                   10                  15

Asn Glu Asn Asn Asn Ser Asn Phe Pro Trp Pro Ala Ala Ser Lys Lys
            20                  25                  30

Asp Asp Ala Gly Lys Gln Gly Thr Asp Gly Asn Asn Ile Ala Phe Gly
        35                  40                  45

Glu

<210> SEQ ID NO 34
<211> LENGTH: 49
<212> TYPE: PRT
<213> ORGANISM: Artificial Sequence
<220> FEATURE:
<223> OTHER INFORMATION: Synthetic

<400> SEQUENCE: 34

Gly Asn Thr Ser Gly Thr Thr Ser Lys Arg Pro Leu Met Thr Thr Ala
1               5                   10                  15

Asn Glu Asn Asn Asn Ser Asn Phe Pro Trp Thr Ala Ala Ser Thr Glu
            20                  25                  30

Asp Asp Asn Glu Arg Glu Asp Ala Lys Gly Thr Asp Thr Glu Phe Asp
        35                  40                  45

Arg

<210> SEQ ID NO 35
<211> LENGTH: 49
<212> TYPE: PRT
<213> ORGANISM: Artificial Sequence
<220> FEATURE:
<223> OTHER INFORMATION: Synthetic

<400> SEQUENCE: 35

Ser Asn Ala Ser Gly Thr Thr Gly Ile His Gln Leu Lys Thr Ala Pro
1               5                   10                  15

Asp Arg Asn Asn Asn Ser Glu Phe Pro Trp Thr Ala Ala Ser Lys Glu
                20                  25                  30

Asp Asp Asn Gly Arg Gln Asn Gly Ala Thr Ala Asp Thr Glu Val Glu
            35                  40                  45

Arg

<210> SEQ ID NO 36
<211> LENGTH: 49
<212> TYPE: PRT
<213> ORGANISM: Artificial Sequence
<220> FEATURE:
<223> OTHER INFORMATION: Synthetic

<400> SEQUENCE: 36

Ser Asn Thr Gly Gly Thr Thr Ala Met Arg Glu Leu Glu Lys Ala Pro
1               5                   10                  15

Asn Asp Asn Asn Asn Ser Lys Phe Pro Trp Thr Ala Ala Ser Thr Glu
                20                  25                  30

Asp Asp Thr Gly Lys Glu Ser Thr Ala Glu Thr Asp Val Glu Asp Gly
            35                  40                  45

Arg

<210> SEQ ID NO 37
<211> LENGTH: 49
<212> TYPE: PRT
<213> ORGANISM: Artificial Sequence
<220> FEATURE:
<223> OTHER INFORMATION: Synthetic

<400> SEQUENCE: 37

Ser Asn Ala Ser Gly Thr Ala Gly Leu Gln Arg Leu Lys Lys Ile Pro
1               5                   10                  15

Asp Gln Asn Asn Asn Ser Asn Phe Pro Trp Thr Ala Ala Ser Lys Lys
                20                  25                  30

Asp Asp Asn Gly Lys Gln Ser Gly Ala Ala Asp Ile Asp Asn Gly
            35                  40                  45

Asn

<210> SEQ ID NO 38
<211> LENGTH: 49
<212> TYPE: PRT
<213> ORGANISM: Artificial Sequence
<220> FEATURE:
<223> OTHER INFORMATION: Synthetic

<400> SEQUENCE: 38

Gly Asn Pro Ser Gly Thr Thr Ala Pro His Arg Leu Leu Thr Ile His
1               5                   10                  15

Asn Gly Asn Asn Asn Ser Asn Phe Pro Trp Pro Ala Ala Ser Thr Lys
                20                  25                  30

Asp Asp Asp Gly Arg Gln Asp Gly Gly Thr Ser Asn Ile Asp Ile Asp
            35                  40                  45

Gly

<210> SEQ ID NO 39
<211> LENGTH: 49

```
<212> TYPE: PRT
<213> ORGANISM: Artificial Sequence
<220> FEATURE:
<223> OTHER INFORMATION: Synthetic

<400> SEQUENCE: 39

Gly Thr Pro Ser Gly Thr Thr Asp Leu Arg Glu Leu Ala Lys Ile Pro
1               5                   10                  15

Asn Asp Asn Asn Asn Ser Asn Phe Pro Trp Thr Ala Ala Ser Thr Glu
            20                  25                  30

Asp Asp Glu Asp Arg Glu Gly Thr Thr Ala Ser Asn Ala Glu Leu Asp
        35                  40                  45

Asn

<210> SEQ ID NO 40
<211> LENGTH: 49
<212> TYPE: PRT
<213> ORGANISM: Artificial Sequence
<220> FEATURE:
<223> OTHER INFORMATION: Synthetic

<400> SEQUENCE: 40

Ser Asn Pro Ser Gly Thr Ala Asn Pro Arg Thr Leu Met Lys Ile Asp
1               5                   10                  15

Ala His Asn Asn Asn Ser Glu Phe Pro Trp Pro Ala Ala Ser Thr Glu
            20                  25                  30

Asp Asp Asn Gly Lys Gln Ser Ser Thr Thr Gly Asp Val Glu Asp Asp
        35                  40                  45

Asp

<210> SEQ ID NO 41
<211> LENGTH: 49
<212> TYPE: PRT
<213> ORGANISM: Artificial Sequence
<220> FEATURE:
<223> OTHER INFORMATION: Synthetic

<400> SEQUENCE: 41

Gly Asn Ala Ser Gly Thr Thr Asp Thr Lys Arg Leu Thr Lys Ala Ser
1               5                   10                  15

Gly Gly Asn Asn Asn Ser Asn Phe Pro Trp Thr Ala Ala Ser Thr Lys
            20                  25                  30

Asp Asp Asp Asp Lys Glu Gly Ser Asn Arg Asp Ala Glu Val Asp
        35                  40                  45

Arg

<210> SEQ ID NO 42
<211> LENGTH: 49
<212> TYPE: PRT
<213> ORGANISM: Artificial Sequence
<220> FEATURE:
<223> OTHER INFORMATION: Synthetic

<400> SEQUENCE: 42

Gly Asn Thr Gly Gly Thr Thr Asp Ile Arg Arg Leu Arg Lys Thr His
1               5                   10                  15

Ser Glu Asn Asn Asn Ser Glu Phe Pro Trp Thr Ala Ala Ser Thr Lys
            20                  25                  30

Asp Asp Asn Glu Arg Gln Asp Thr Arg Glu Thr Asp Val Ala Ile Asp
        35                  40                  45
```

Arg

<210> SEQ ID NO 43
<211> LENGTH: 49
<212> TYPE: PRT
<213> ORGANISM: Artificial Sequence
<220> FEATURE:
<223> OTHER INFORMATION: Synthetic

<400> SEQUENCE: 43

Gly Asn Ala Ser Gly Thr Ala Gly Met Arg Glu Leu Met Lys Ala Ala
1               5                   10                  15

Asn His Asn Asn Asn Ser Asn Phe Pro Trp Thr Ala Ala Ser Lys Glu
            20                  25                  30

Asp Asp Glu Asp Lys Glu Ser Gly Ser Ala Asp Asp Val Ala Ile Gly
        35                  40                  45

Arg

<210> SEQ ID NO 44
<211> LENGTH: 49
<212> TYPE: PRT
<213> ORGANISM: Artificial Sequence
<220> FEATURE:
<223> OTHER INFORMATION: Synthetic

<400> SEQUENCE: 44

Ser Asn Thr Gly Gly Thr Ala Thr Pro Lys Gln Leu Gln Lys Ala Ser
1               5                   10                  15

Ala His Asn Asn Asn Ser Glu Phe Pro Trp Thr Ala Ala Ser Lys Lys
            20                  25                  30

Asp Asp Glu Glu Arg Glu Gly Ser Thr Arg Asn Asp Ile Ala Asn Glu
        35                  40                  45

His

<210> SEQ ID NO 45
<211> LENGTH: 49
<212> TYPE: PRT
<213> ORGANISM: Artificial Sequence
<220> FEATURE:
<223> OTHER INFORMATION: Synthetic

<400> SEQUENCE: 45

Ser Asn Thr Gly Gly Thr Ala Asn Ile Lys Glu Leu Thr Lys Thr Ser
1               5                   10                  15

Asn Asp Asn Asn Asn Ser Asn Phe Pro Trp Thr Ala Ala Ser Thr Arg
            20                  25                  30

Asp Asp Asn Asp Lys Gln Ser Ala Ser Lys Asn Asp Ile Glu Tyr Glu
        35                  40                  45

Gln

<210> SEQ ID NO 46
<211> LENGTH: 49
<212> TYPE: PRT
<213> ORGANISM: Artificial Sequence
<220> FEATURE:
<223> OTHER INFORMATION: Synthetic

<400> SEQUENCE: 46

Ser Asn Ala Gly Gly Thr Thr Ser Asn Arg Glu Leu Arg Thr Thr Ser
1               5                   10                  15

Ser Gln Asn Asn Asn Ser Asn Phe Pro Trp Thr Ala Ala Ser Thr Arg

```
                20                  25                  30
Asp Asp Asp Asp Arg Gln Asp Ala Gly Gly Asn Asp Val Glu Val Gly
        35                  40                  45

Asp

<210> SEQ ID NO 47
<211> LENGTH: 49
<212> TYPE: PRT
<213> ORGANISM: Artificial Sequence
<220> FEATURE:
<223> OTHER INFORMATION: Synthetic

<400> SEQUENCE: 47

Ser Asn Thr Ser Gly Thr Ala Thr Thr Ser Ala Leu Lys Lys Thr Tyr
1               5                   10                  15

Gly His Asn Asn Asn Ser Asn Phe Pro Trp Thr Ala Ala Ser Lys Gly
                20                  25                  30

Asp Asp Thr Glu Lys Gln Gly Gly Ser Ala Asn Asn Val Glu Val Glu
        35                  40                  45

Ser

<210> SEQ ID NO 48
<211> LENGTH: 49
<212> TYPE: PRT
<213> ORGANISM: Artificial Sequence
<220> FEATURE:
<223> OTHER INFORMATION: Synthetic

<400> SEQUENCE: 48

Ser Asn Ala Gly Gly Thr Ala Ala Thr Asn Arg Leu Leu Lys Ile Tyr
1               5                   10                  15

Asp Arg Asn Asn Asn Ser Asn Phe Pro Trp Thr Ala Ala Ser Thr Arg
                20                  25                  30

Asp Asp Glu Asp Lys Glu Gly Gly Glu Lys Gly Asn Val Asp Ile Asp
        35                  40                  45

Arg

<210> SEQ ID NO 49
<211> LENGTH: 49
<212> TYPE: PRT
<213> ORGANISM: Artificial Sequence
<220> FEATURE:
<223> OTHER INFORMATION: Synthetic

<400> SEQUENCE: 49

Ser Thr Pro Ser Gly Thr Thr Ala Thr Lys Gly Leu Thr Thr Ala His
1               5                   10                  15

Thr Gly Asn Asn Asn Ser Asn Phe Pro Trp Thr Ala Ala Ser Lys Gly
                20                  25                  30

Asp Asp Asp Gly Lys Glu Gly Ser Thr Ala Thr Asp Val Ala Ile Gly
        35                  40                  45

Ser

<210> SEQ ID NO 50
<211> LENGTH: 49
<212> TYPE: PRT
<213> ORGANISM: Artificial Sequence
<220> FEATURE:
<223> OTHER INFORMATION: Synthetic

<400> SEQUENCE: 50
```

-continued

Gly Asn Thr Gly Gly Thr Thr Asp Leu Arg Arg Leu Met Thr Thr Asp
1               5                   10                  15

Asn His Asn Asn Asn Ser Glu Phe Pro Trp Pro Ala Ala Ser Thr Gly
                20                  25                  30

Asp Asp Lys Gly Arg Glu Asn Gly Ala Lys Asn Asp Ile Ala Phe Glu
        35                  40                  45

Gly

<210> SEQ ID NO 51
<211> LENGTH: 49
<212> TYPE: PRT
<213> ORGANISM: Artificial Sequence
<220> FEATURE:
<223> OTHER INFORMATION: Synthetic

<400> SEQUENCE: 51

Ser Thr Thr Ser Gly Thr Thr Thr Leu Lys Ala Leu Gln Lys Ile Pro
1               5                   10                  15

Asn Arg Asn Asn Asn Ser Asn Phe Pro Trp Thr Ala Ala Ser Thr Gly
                20                  25                  30

Asp Asp Glu Asp Arg Glu Asn Ser Lys Gly Ala Asn Thr Glu Ile Asp
        35                  40                  45

Glu

<210> SEQ ID NO 52
<211> LENGTH: 49
<212> TYPE: PRT
<213> ORGANISM: Artificial Sequence
<220> FEATURE:
<223> OTHER INFORMATION: Synthetic

<400> SEQUENCE: 52

Gly Thr Thr Ser Gly Thr Thr Asp Pro Lys Asp Leu Val Thr Thr His
1               5                   10                  15

Gly Asp Asn Asn Asn Ser Asp Phe Pro Trp Thr Ala Ala Ser Thr Lys
                20                  25                  30

Asp Asp Asp Asp Lys Glu Asp Thr Ala Ala Asp Asn Val Glu Phe Gly
        35                  40                  45

Arg

<210> SEQ ID NO 53
<211> LENGTH: 49
<212> TYPE: PRT
<213> ORGANISM: Artificial Sequence
<220> FEATURE:
<223> OTHER INFORMATION: Synthetic

<400> SEQUENCE: 53

Ser Thr Ala Gly Gly Thr Thr Thr Ile Lys Asp Leu Val Lys Val Pro
1               5                   10                  15

Asp Asp Asn Asn Asn Ser Lys Phe Pro Trp Thr Ala Ala Ser Lys Glu
                20                  25                  30

Asp Asp Asp Glu Arg Gln Asp Ser Gly Ala Thr Asn Val Glu Phe Gly
        35                  40                  45

Arg

<210> SEQ ID NO 54
<211> LENGTH: 49
<212> TYPE: PRT

<213> ORGANISM: Artificial Sequence
<220> FEATURE:
<223> OTHER INFORMATION: Synthetic

<400> SEQUENCE: 54

Gly Thr Thr Gly Gly Thr Thr Thr Met Arg Lys Leu Gly Lys Val Tyr
1               5                   10                  15

Gly Gly Asn Asn Asn Ser Asn Phe Pro Trp Thr Ala Ala Ser Thr Glu
            20                  25                  30

Asp Asp Ala Glu Arg Gln Ser Ser Gly Arg Asn Asp Val Glu Tyr Gly
        35                  40                  45

Asp

<210> SEQ ID NO 55
<211> LENGTH: 49
<212> TYPE: PRT
<213> ORGANISM: Artificial Sequence
<220> FEATURE:
<223> OTHER INFORMATION: Synthetic

<400> SEQUENCE: 55

Gly Asn Thr Gly Gly Thr Ala Ser Thr Arg Arg Leu Thr Lys Ile Pro
1               5                   10                  15

Asp Gln Asn Asn Asn Ser Asn Phe Pro Trp Pro Ala Ala Ser Lys Glu
            20                  25                  30

Asp Asp Glu Gly Arg Gln Ser Ala Glu Lys Gly Asp Ile Glu Tyr Gly
        35                  40                  45

Arg

<210> SEQ ID NO 56
<211> LENGTH: 49
<212> TYPE: PRT
<213> ORGANISM: Artificial Sequence
<220> FEATURE:
<223> OTHER INFORMATION: Synthetic

<400> SEQUENCE: 56

Gly Asn Thr Ser Gly Thr Thr Ala Thr His Thr Leu Ala Lys Ile His
1               5                   10                  15

Ser Arg Asn Asn Asn Ser Asp Phe Pro Trp Pro Ala Ala Ser Lys Glu
            20                  25                  30

Asp Asp Ala Gly Lys Gln Gly Ala Thr Ala Gly Asn Ile Asp Val Glu
        35                  40                  45

Gln

<210> SEQ ID NO 57
<211> LENGTH: 49
<212> TYPE: PRT
<213> ORGANISM: Artificial Sequence
<220> FEATURE:
<223> OTHER INFORMATION: Synthetic

<400> SEQUENCE: 57

Ser Asn Pro Gly Gly Thr Thr Ser Ile Arg Gly Leu Gln Thr Ile Pro
1               5                   10                  15

Asn Arg Asn Asn Asn Ser Asn Phe Pro Trp Pro Ala Ala Ser Thr Arg
            20                  25                  30

Asp Asp Thr Asp Lys Gln Gly Gly Ala Gly Asn Thr Asp Phe Asp
        35                  40                  45

His

<210> SEQ ID NO 58
<211> LENGTH: 49
<212> TYPE: PRT
<213> ORGANISM: Artificial Sequence
<220> FEATURE:
<223> OTHER INFORMATION: Synthetic

<400> SEQUENCE: 58

Ser Thr Thr Ser Gly Thr Ala Ala Pro Arg Gly Leu Val Thr Val Tyr
1               5                   10                  15

Gly His Asn Asn Asn Ser Glu Phe Pro Trp Thr Ala Ala Ser Lys Lys
            20                  25                  30

Asp Asp Glu Gly Arg Glu Gly Ala Gly Ala Ser Asn Val Ala Ile Glu
        35                  40                  45

Glu

<210> SEQ ID NO 59
<211> LENGTH: 49
<212> TYPE: PRT
<213> ORGANISM: Artificial Sequence
<220> FEATURE:
<223> OTHER INFORMATION: Synthetic

<400> SEQUENCE: 59

Gly Asn Ala Ser Gly Thr Ala Thr Lys Gln Gly Leu Met Lys Val Pro
1               5                   10                  15

Asn Gln Asn Asn Asn Ser Asp Phe Pro Trp Thr Ala Ala Ser Lys Lys
            20                  25                  30

Asp Asp Asp Asp Arg Gln Ser Ser Asp Lys Asn Asn Ala Glu Asp Asp
        35                  40                  45

Ser

<210> SEQ ID NO 60
<211> LENGTH: 49
<212> TYPE: PRT
<213> ORGANISM: Artificial Sequence
<220> FEATURE:
<223> OTHER INFORMATION: Synthetic

<400> SEQUENCE: 60

Ser Asn Ala Gly Gly Thr Ala Thr Ser Gln Leu Arg Thr Ala Pro
1               5                   10                  15

Ala Glu Asn Asn Asn Ser Asn Phe Pro Trp Pro Ala Ala Ser Thr Arg
            20                  25                  30

Asp Asp Ala Asp Arg Glu Ser Gly Arg Gly Asp Asn Val Asp Phe Glu
        35                  40                  45

Lys

<210> SEQ ID NO 61
<211> LENGTH: 49
<212> TYPE: PRT
<213> ORGANISM: Artificial Sequence
<220> FEATURE:
<223> OTHER INFORMATION: Synthetic

<400> SEQUENCE: 61

Ser Asn Thr Gly Gly Thr Ala Gly Ile Arg Ala Leu Gln Lys Val Asp
1               5                   10                  15

Thr Gly Asn Asn Asn Ser Asp Phe Pro Trp Thr Ala Ala Ser Thr Glu
            20                  25                  30

Asp Asp Thr Glu Lys Glu Asn Ser Ala Arg Asn Asp Ala Asp Ile Gly
        35                  40                  45
Arg

<210> SEQ ID NO 62
<211> LENGTH: 49
<212> TYPE: PRT
<213> ORGANISM: Artificial Sequence
<220> FEATURE:
<223> OTHER INFORMATION: Synthetic

<400> SEQUENCE: 62

Gly Asn Ala Ser Gly Thr Ala Ala Gln Asn Gly Leu Arg Lys Ile Pro
1               5                   10                  15

Asn Glu Asn Asn Asn Ser Lys Phe Pro Trp Thr Ala Ser Thr Lys
            20                  25                  30

Asp Asp Glu Gly Lys Glu Ser Ser Gly Asp Asp Ala Glu Phe Gly
        35                  40                  45
Gly

<210> SEQ ID NO 63
<211> LENGTH: 49
<212> TYPE: PRT
<213> ORGANISM: Artificial Sequence
<220> FEATURE:
<223> OTHER INFORMATION: Synthetic

<400> SEQUENCE: 63

Ser Asn Thr Ser Gly Thr Ala Gly Pro Gln Gln Leu Arg Lys Thr His
1               5                   10                  15

Ala Gln Asn Asn Asn Ser Asn Phe Pro Trp Thr Ala Ala Ser Lys Glu
            20                  25                  30

Asp Asp Thr Gly Lys Glu Gly Ala Arg Ala Asn Asp Ile Ala Phe Asp
        35                  40                  45
Gln

<210> SEQ ID NO 64
<211> LENGTH: 49
<212> TYPE: PRT
<213> ORGANISM: Artificial Sequence
<220> FEATURE:
<223> OTHER INFORMATION: Synthetic

<400> SEQUENCE: 64

Ser Thr Pro Ser Gly Thr Thr Ser Met Arg Thr Leu Glu Lys Ala Pro
1               5                   10                  15

Ala Arg Asn Asn Asn Ser Glu Phe Pro Trp Thr Ala Ala Ser Thr Arg
            20                  25                  30

Asp Asp Ala Gly Lys Gln Gly Ser Arg Glu Asn Asp Thr Glu Phe Asp
        35                  40                  45
Gly

<210> SEQ ID NO 65
<211> LENGTH: 49
<212> TYPE: PRT
<213> ORGANISM: Artificial Sequence
<220> FEATURE:
<223> OTHER INFORMATION: Synthetic

<400> SEQUENCE: 65

Ser Thr Ala Gly Gly Thr Thr Ala Leu Lys Gly Leu Lys Thr Ile Ala
1               5                   10                  15

Asp His Asn Asn Asn Ser Glu Phe Pro Trp Pro Ala Ala Ser Thr Arg
            20                  25                  30

Asp Asp Lys Glu Lys Glu Asp Ser Thr Gly Ala Asn Ile Ala Asp Asp
        35                  40                  45

Arg

<210> SEQ ID NO 66
<211> LENGTH: 49
<212> TYPE: PRT
<213> ORGANISM: Artificial Sequence
<220> FEATURE:
<223> OTHER INFORMATION: Synthetic

<400> SEQUENCE: 66

Ser Thr Pro Ser Gly Thr Ala Ser Thr Arg Thr Leu Met Lys Thr His
1               5                   10                  15

Asn His Asn Asn Asn Ser Glu Phe Pro Trp Thr Ala Ala Ser Thr Lys
            20                  25                  30

Asp Asp Glu Asp Lys Glu Gly Thr Glu Ala Thr Asn Val Ala Ile Gly
        35                  40                  45

Gly

<210> SEQ ID NO 67
<211> LENGTH: 49
<212> TYPE: PRT
<213> ORGANISM: Artificial Sequence
<220> FEATURE:
<223> OTHER INFORMATION: Synthetic

<400> SEQUENCE: 67

Gly Asn Pro Gly Gly Thr Thr Asn Asn Gln Ala Leu Arg Lys Ile His
1               5                   10                  15

Gly Gln Asn Asn Asn Ser Asp Phe Pro Trp Thr Ala Ala Ser Thr Arg
            20                  25                  30

Asp Asp Asn Asp Lys Glu Gly Ser Ala Arg Gly Asp Val Ala Tyr Glu
        35                  40                  45

Lys

<210> SEQ ID NO 68
<211> LENGTH: 49
<212> TYPE: PRT
<213> ORGANISM: Artificial Sequence
<220> FEATURE:
<223> OTHER INFORMATION: Synthetic

<400> SEQUENCE: 68

Ser Asn Ala Ser Gly Thr Thr Asp Thr Arg Glu Leu Val Thr Ile Ala
1               5                   10                  15

Asp Asp Asn Asn Asn Ser Glu Phe Pro Trp Thr Ala Ala Ser Thr Arg
            20                  25                  30

Asp Asp Thr Asp Lys Gln Gly Ser Ala Gly Ala Asp Val Glu Val Glu
        35                  40                  45

Lys

<210> SEQ ID NO 69
<211> LENGTH: 49
<212> TYPE: PRT
<213> ORGANISM: Artificial Sequence
<220> FEATURE:
<223> OTHER INFORMATION: Synthetic

<400> SEQUENCE: 69

Ser Asn Pro Gly Gly Thr Thr Asn Leu Arg Glu Leu Arg Thr Ile His
1               5                   10                  15

Thr Glu Asn Asn Asn Ser Glu Phe Pro Trp Thr Ala Ala Ser Thr Arg
            20                  25                  30

Asp Asp Lys Asp Arg Gln Gly Gly Gly Thr Asn Val Glu Ile Gly
        35                  40                  45

Ser

<210> SEQ ID NO 70
<211> LENGTH: 49
<212> TYPE: PRT
<213> ORGANISM: Artificial Sequence
<220> FEATURE:
<223> OTHER INFORMATION: Synthetic

<400> SEQUENCE: 70

Gly Thr Thr Gly Gly Thr Ala Asn Asn Thr Leu Leu Lys Ile Ala
1               5                   10                  15

Ser Gly Asn Asn Asn Ser Asn Phe Pro Trp Thr Ala Ala Ser Thr Lys
            20                  25                  30

Asp Asp Lys Gly Arg Glu Gly Ala Glu Lys Asn Asp Thr Ala Val Gly
        35                  40                  45

Asn

<210> SEQ ID NO 71
<211> LENGTH: 49
<212> TYPE: PRT
<213> ORGANISM: Artificial Sequence
<220> FEATURE:
<223> OTHER INFORMATION: Synthetic

<400> SEQUENCE: 71

Gly Thr Thr Ser Gly Thr Thr Asp Lys Gln Gln Leu Met Lys Thr His
1               5                   10                  15

Asn Gly Asn Asn Asn Ser Asp Phe Pro Trp Thr Ala Ala Ser Lys Glu
            20                  25                  30

Asp Asp Thr Gly Lys Gln Ser Ala Glu Gly Asn Val Ala Tyr Asp
        35                  40                  45

Gly

<210> SEQ ID NO 72
<211> LENGTH: 49
<212> TYPE: PRT
<213> ORGANISM: Artificial Sequence
<220> FEATURE:
<223> OTHER INFORMATION: Synthetic

<400> SEQUENCE: 72

Gly Thr Ala Gly Gly Thr Ala Thr Leu Ser Thr Leu Val Lys Ile Ser
1               5                   10                  15

Ala Gly Asn Asn Asn Ser Asp Phe Pro Trp Thr Ala Ala Ser Lys Gly
            20                  25                  30

Asp Asp Asn Gly Lys Gln Asn Ser Thr Ala Ser Asp Val Ala Ile Asp
        35                  40                  45

Gly

```
<210> SEQ ID NO 73
<211> LENGTH: 49
<212> TYPE: PRT
<213> ORGANISM: Artificial Sequence
<220> FEATURE:
<223> OTHER INFORMATION: Synthetic

<400> SEQUENCE: 73

Ser Asn Thr Ser Gly Thr Ala Gly Leu Arg Thr Leu Thr Lys Ala Asp
1               5                   10                  15

Ala Asp Asn Asn Asn Ser Asp Phe Pro Trp Pro Ala Ala Ser Thr Gly
            20                  25                  30

Asp Asp Asn Gly Lys Glu Asp Ala Ser Gly Asn Asn Val Glu Asp Gly
        35                  40                  45

Arg

<210> SEQ ID NO 74
<211> LENGTH: 49
<212> TYPE: PRT
<213> ORGANISM: Artificial Sequence
<220> FEATURE:
<223> OTHER INFORMATION: Synthetic

<400> SEQUENCE: 74

Ser Asn Ala Ser Gly Thr Ala Thr Pro Ser Thr Leu Arg Lys Thr Asp
1               5                   10                  15

Thr His Asn Asn Asn Ser Glu Phe Pro Trp Pro Ala Ala Ser Lys Arg
            20                  25                  30

Asp Asp Asn Asp Arg Glu Gly Ala Arg Gly Ser Asn Ile Asp Val Gly
        35                  40                  45

Asp

<210> SEQ ID NO 75
<211> LENGTH: 49
<212> TYPE: PRT
<213> ORGANISM: Artificial Sequence
<220> FEATURE:
<223> OTHER INFORMATION: Synthetic

<400> SEQUENCE: 75

Ser Thr Ala Ser Gly Thr Ala Ser Leu Arg Ala Leu Met Lys Val Pro
1               5                   10                  15

Asn Arg Asn Asn Asn Ser Asn Phe Pro Trp Thr Ala Ala Ser Thr Gly
            20                  25                  30

Asp Asp Asn Asp Lys Glu Asn Ala Arg Ala Ser Asp Ala Glu Val Asp
        35                  40                  45

Arg

<210> SEQ ID NO 76
<211> LENGTH: 49
<212> TYPE: PRT
<213> ORGANISM: Artificial Sequence
<220> FEATURE:
<223> OTHER INFORMATION: Synthetic

<400> SEQUENCE: 76

Gly Thr Ala Ser Gly Thr Ala Thr Thr Lys Gly Leu Leu Lys Ile Ser
1               5                   10                  15

Thr Gln Asn Asn Asn Ser Asn Phe Pro Trp Thr Ala Ala Ser Lys Glu
            20                  25                  30
```

Asp Asp Ala Asp Lys Gln Gly Gly Glu Thr Asp Asn Val Asp Val Gly
            35                  40                  45

Asp

<210> SEQ ID NO 77
<211> LENGTH: 49
<212> TYPE: PRT
<213> ORGANISM: Artificial Sequence
<220> FEATURE:
<223> OTHER INFORMATION: Synthetic

<400> SEQUENCE: 77

Gly Thr Ala Ser Gly Thr Ala Ala Leu Lys Gln Leu Ala Lys Ala Asp
1               5                   10                  15

Ser Asp Asn Asn Asn Ser Asn Phe Pro Trp Thr Ala Ala Ser Thr Glu
            20                  25                  30

Asp Asp Ala Asp Arg Gln Gly Gly Glu Thr Gly Asn Ile Glu Tyr Asp
            35                  40                  45

Gly

<210> SEQ ID NO 78
<211> LENGTH: 49
<212> TYPE: PRT
<213> ORGANISM: Artificial Sequence
<220> FEATURE:
<223> OTHER INFORMATION: Synthetic

<400> SEQUENCE: 78

Gly Asn Ala Ser Gly Thr Ala Thr Thr Ser Asn Leu Met Lys Ala Asp
1               5                   10                  15

Asp Arg Asn Asn Asn Ser Asn Phe Pro Trp Thr Ala Ala Ser Thr Lys
            20                  25                  30

Asp Asp Glu Asp Arg Gln Gly Ala Lys Arg Ser Asp Thr Ala Val Glu
            35                  40                  45

Glu

<210> SEQ ID NO 79
<211> LENGTH: 49
<212> TYPE: PRT
<213> ORGANISM: Artificial Sequence
<220> FEATURE:
<223> OTHER INFORMATION: Synthetic

<400> SEQUENCE: 79

Gly Thr Ala Gly Gly Thr Ala Asn Met Lys Asp Leu Arg Thr Thr Ala
1               5                   10                  15

Ser Glu Asn Asn Asn Ser Asp Phe Pro Trp Thr Ala Ala Ser Thr Glu
            20                  25                  30

Asp Asp Lys Asp Lys Glu Gly Ala Asn Gly Gly Asp Val Ala Ile Gly
            35                  40                  45

Gln

<210> SEQ ID NO 80
<211> LENGTH: 49
<212> TYPE: PRT
<213> ORGANISM: Artificial Sequence
<220> FEATURE:
<223> OTHER INFORMATION: Synthetic

<400> SEQUENCE: 80

Ser Thr Pro Gly Gly Thr Thr Thr Ile Arg Asp Leu Lys Thr Val Ser

```
              1               5                  10                 15
Thr Asp Asn Asn Asn Ser Asp Phe Pro Trp Pro Ala Ala Ser Thr Lys
            20                  25                 30
Asp Asp Asp Asp Arg Glu Gly Ser Gly Arg Asn Asn Val Ala Val Glu
            35                  40                 45
Glu
```

<210> SEQ ID NO 81
<211> LENGTH: 49
<212> TYPE: PRT
<213> ORGANISM: Artificial Sequence
<220> FEATURE:
<223> OTHER INFORMATION: Synthetic

<400> SEQUENCE: 81

```
Ser Thr Pro Ser Gly Thr Ala Asn Ile Asn Thr Leu Arg Lys Thr Pro
1               5                  10                 15
Asn Arg Asn Asn Asn Ser Asn Phe Pro Trp Thr Ala Ala Ser Thr Glu
            20                  25                 30
Asp Asp Glu Gly Arg Gln Ser Ala Thr Lys Asp Asp Val Asp Ile Gly
            35                  40                 45
Gly
```

<210> SEQ ID NO 82
<211> LENGTH: 49
<212> TYPE: PRT
<213> ORGANISM: Artificial Sequence
<220> FEATURE:
<223> OTHER INFORMATION: Synthetic

<400> SEQUENCE: 82

```
Gly Asn Thr Gly Gly Thr Ala Gly Leu Gln Lys Leu Met Lys Thr His
1               5                  10                 15
Gly Gly Asn Asn Asn Ser Asn Phe Pro Trp Pro Ala Ala Ser Thr Lys
            20                  25                 30
Asp Asp Asp Gly Lys Gln Ser Ser Arg Gly Asn Asp Val Ala Val Asp
            35                  40                 45
Asp
```

<210> SEQ ID NO 83
<211> LENGTH: 49
<212> TYPE: PRT
<213> ORGANISM: Artificial Sequence
<220> FEATURE:
<223> OTHER INFORMATION: Synthetic

<400> SEQUENCE: 83

```
Gly Asn Thr Ser Gly Thr Thr Thr Pro Arg Thr Leu Ala Lys Ile Pro
1               5                  10                 15
Ser His Asn Asn Asn Ser Glu Phe Pro Trp Thr Ala Ala Ser Lys Lys
            20                  25                 30
Asp Asp Glu Glu Lys Gln Gly Ser Asn Gly Ser Asn Ile Glu Phe Gly
            35                  40                 45
Ser
```

<210> SEQ ID NO 84
<211> LENGTH: 49
<212> TYPE: PRT
<213> ORGANISM: Artificial Sequence
<220> FEATURE:

<223> OTHER INFORMATION: Synthetic

<400> SEQUENCE: 84

Ser Asn Ala Gly Gly Thr Ala Gly Leu Arg Gln Leu Thr Lys Ala Pro
1               5                   10                  15

Ala Glu Asn Asn Asn Ser Asp Phe Pro Trp Thr Ala Ala Ser Thr Glu
            20                  25                  30

Asp Asp Ala Gly Lys Glu Gly Gly Gly Ala Asn Ile Ala Val Glu
        35                  40                  45

Glu

<210> SEQ ID NO 85
<211> LENGTH: 49
<212> TYPE: PRT
<213> ORGANISM: Artificial Sequence
<220> FEATURE:
<223> OTHER INFORMATION: Synthetic

<400> SEQUENCE: 85

Gly Thr Ala Ser Gly Thr Ala Ala Lys Ser Thr Leu Val Lys Ile Ser
1               5                   10                  15

Thr Arg Asn Asn Asn Ser Asn Phe Pro Trp Thr Ala Ala Ser Thr Glu
            20                  25                  30

Asp Asp Glu Glu Lys Glu Gly Thr Ser Lys Asn Asp Val Glu Val Glu
        35                  40                  45

Asn

<210> SEQ ID NO 86
<211> LENGTH: 49
<212> TYPE: PRT
<213> ORGANISM: Artificial Sequence
<220> FEATURE:
<223> OTHER INFORMATION: Synthetic

<400> SEQUENCE: 86

Gly Thr Thr Ser Gly Thr Thr Thr Thr Arg Arg Leu Met Lys Ile Tyr
1               5                   10                  15

Gly Gly Asn Asn Asn Ser Asn Phe Pro Trp Thr Ala Ala Ser Thr Glu
            20                  25                  30

Asp Asp Ala Gly Arg Gln Gly Thr Ala Thr Ala Asn Val Glu Val Glu
        35                  40                  45

Ser

<210> SEQ ID NO 87
<211> LENGTH: 49
<212> TYPE: PRT
<213> ORGANISM: Artificial Sequence
<220> FEATURE:
<223> OTHER INFORMATION: Synthetic

<400> SEQUENCE: 87

Gly Thr Ala Gly Gly Thr Ala Gly Met Arg Glu Leu Ala Thr Ile Tyr
1               5                   10                  15

Thr Gly Asn Asn Asn Ser Asn Phe Pro Trp Thr Ala Ala Ser Lys Lys
            20                  25                  30

Asp Asp Glu Gly Arg Glu Gly Ser Ser Thr Gly Asp Ala Asp Val Gly
        35                  40                  45

Arg

-continued

```
<210> SEQ ID NO 88
<211> LENGTH: 49
<212> TYPE: PRT
<213> ORGANISM: Artificial Sequence
<220> FEATURE:
<223> OTHER INFORMATION: Synthetic

<400> SEQUENCE: 88

Ser Thr Thr Gly Gly Thr Ala Asn Pro Lys Glu Leu Arg Thr Ala Ala
1               5                   10                  15

Asn His Asn Asn Ser Glu Phe Pro Trp Thr Ala Ala Ser Thr Glu
            20                  25                  30

Asp Asp Glu Asp Lys Gln Gly Ala Gly Glu Ser Asn Val Ala Ile Asp
        35                  40                  45

Gly

<210> SEQ ID NO 89
<211> LENGTH: 49
<212> TYPE: PRT
<213> ORGANISM: Artificial Sequence
<220> FEATURE:
<223> OTHER INFORMATION: Synthetic

<400> SEQUENCE: 89

Gly Thr Thr Ser Gly Thr Thr Gly Thr Ser Thr Leu Arg Lys Thr Asp
1               5                   10                  15

Thr Gly Asn Asn Asn Ser Asn Phe Pro Trp Thr Ala Ala Ser Lys Gly
            20                  25                  30

Asp Asp Glu Glu Arg Glu Gly Ala Gly Thr Ala Asp Ala Ala Val Asp
        35                  40                  45

Gly

<210> SEQ ID NO 90
<211> LENGTH: 49
<212> TYPE: PRT
<213> ORGANISM: Artificial Sequence
<220> FEATURE:
<223> OTHER INFORMATION: Synthetic

<400> SEQUENCE: 90

Gly Asn Ala Gly Gly Thr Thr Asn Lys Arg Asp Leu Leu Thr Ala Tyr
1               5                   10                  15

Thr Arg Asn Asn Asn Ser Asp Phe Pro Trp Thr Ala Ala Ser Thr Lys
            20                  25                  30

Asp Asp Asp Glu Lys Gln Gly Thr Gly Lys Thr Asp Ala Asp Asn Gly
        35                  40                  45

Gly

<210> SEQ ID NO 91
<211> LENGTH: 49
<212> TYPE: PRT
<213> ORGANISM: Artificial Sequence
<220> FEATURE:
<223> OTHER INFORMATION: Synthetic

<400> SEQUENCE: 91

Gly Asn Ala Ser Gly Thr Thr Asp Met Lys His Leu Thr Lys Ile Ser
1               5                   10                  15

Asp Arg Asn Asn Asn Ser Asn Phe Pro Trp Pro Ala Ala Ser Thr Arg
            20                  25                  30

Asp Asp Asn Glu Arg Gln Ser Thr Arg Gly Gly Asn Ala Glu Ile Asp
```

<210> SEQ ID NO 92
<211> LENGTH: 49
<212> TYPE: PRT
<213> ORGANISM: Artificial Sequence
<220> FEATURE:
<223> OTHER INFORMATION: Synthetic

<400> SEQUENCE: 92

Ser Asn Thr Gly Gly Thr Ala Asp Leu Arg Asp Leu Leu Thr Ile Pro
1               5                   10                  15

Thr Gln Asn Asn Asn Ser Glu Phe Pro Trp Thr Ala Ala Ser Lys Lys
                20                  25                  30

Asp Asp Asn Asp Arg Gln Ser Ala Lys Ala Asn Asp Val Glu Val Asp
            35                  40                  45

Arg

<210> SEQ ID NO 93
<211> LENGTH: 49
<212> TYPE: PRT
<213> ORGANISM: Artificial Sequence
<220> FEATURE:
<223> OTHER INFORMATION: Synthetic

<400> SEQUENCE: 93

Ser Thr Ala Ser Gly Thr Thr Ala Thr Gln Gln Leu Val Thr Thr Asp
1               5                   10                  15

Ser Gln Asn Asn Asn Ser Glu Phe Pro Trp Thr Ala Ala Ser Thr Arg
                20                  25                  30

Asp Asp Asn Asp Arg Glu Asn Ala Glu Gly Gly Asn Val Glu Ile Gly
            35                  40                  45

Gln

<210> SEQ ID NO 94
<211> LENGTH: 49
<212> TYPE: PRT
<213> ORGANISM: Artificial Sequence
<220> FEATURE:
<223> OTHER INFORMATION: Synthetic

<400> SEQUENCE: 94

Gly Asn Ala Gly Gly Thr Thr Ala Asn Lys Thr Leu Met Lys Ile Ala
1               5                   10                  15

Ala His Asn Asn Asn Ser Glu Phe Pro Trp Thr Ala Ala Ser Thr Arg
                20                  25                  30

Asp Asp Asp Gly Lys Gln Asp Ser Ser Ala Asp Asn Ile Glu Tyr Gly
            35                  40                  45

Lys

<210> SEQ ID NO 95
<211> LENGTH: 49
<212> TYPE: PRT
<213> ORGANISM: Artificial Sequence
<220> FEATURE:
<223> OTHER INFORMATION: Synthetic

<400> SEQUENCE: 95

Gly Asn Ala Gly Gly Thr Thr Gly Thr Lys Glu Leu Arg Thr Ile Ala
1               5                   10                  15

Asn Glu Asn Asn Asn Ser Asn Phe Pro Trp Thr Ala Ala Ser Thr Lys
                20                  25                  30

Asp Asp Asp Glu Lys Glu Asp Ala Lys Arg Asn Asn Val Asp Tyr Asp
            35                  40                  45

Gly

<210> SEQ ID NO 96
<211> LENGTH: 49
<212> TYPE: PRT
<213> ORGANISM: Artificial Sequence
<220> FEATURE:
<223> OTHER INFORMATION: Synthetic

<400> SEQUENCE: 96

Ser Asn Pro Ser Gly Thr Thr Gly Lys Ser Ser Leu Lys Lys Thr Ser
1               5                   10                  15

Asn Glu Asn Asn Asn Ser Asn Phe Pro Trp Thr Ala Ala Ser Lys Lys
                20                  25                  30

Asp Asp Asn Gly Lys Glu Asp Ser Arg Ala Gly Asp Ala Asp Phe Glu
            35                  40                  45

Lys

<210> SEQ ID NO 97
<211> LENGTH: 49
<212> TYPE: PRT
<213> ORGANISM: Artificial Sequence
<220> FEATURE:
<223> OTHER INFORMATION: Synthetic

<400> SEQUENCE: 97

Gly Asn Thr Ser Gly Thr Ala Ser Ile Arg Gln Leu Gln Lys Thr Pro
1               5                   10                  15

Asp Gly Asn Asn Asn Ser Lys Phe Pro Trp Thr Ala Ala Ser Lys Arg
                20                  25                  30

Asp Asp Asn Gly Arg Glu Gly Ser Thr Glu Gly Asn Ile Glu Ile Glu
            35                  40                  45

Gly

<210> SEQ ID NO 98
<211> LENGTH: 49
<212> TYPE: PRT
<213> ORGANISM: Artificial Sequence
<220> FEATURE:
<223> OTHER INFORMATION: Synthetic

<400> SEQUENCE: 98

Gly Asn Thr Gly Gly Thr Thr Thr Leu Ser Ala Leu Gly Thr Ala His
1               5                   10                  15

Thr Gln Asn Asn Asn Ser Asn Phe Pro Trp Thr Ala Ala Ser Lys Arg
                20                  25                  30

Asp Asp Asn Asp Lys Gln Ser Ser Thr Gly Gly Asp Thr Ala Phe Asp
            35                  40                  45

Gly

<210> SEQ ID NO 99
<211> LENGTH: 49
<212> TYPE: PRT
<213> ORGANISM: Artificial Sequence
<220> FEATURE:
<223> OTHER INFORMATION: Synthetic

<400> SEQUENCE: 99

Ser Asn Pro Ser Gly Thr Thr Thr Gln Arg Leu Gln Lys Thr Asp
1               5                   10                  15

Asn Asp Asn Asn Asn Ser Asp Phe Pro Trp Pro Ala Ala Ser Thr Arg
            20                  25                  30

Asp Thr Asp Arg Glu Gly Ser Thr Gly Gly Asp Ala Glu Ile Glu
        35                  40                  45

Arg

<210> SEQ ID NO 100
<211> LENGTH: 49
<212> TYPE: PRT
<213> ORGANISM: Artificial Sequence
<220> FEATURE:
<223> OTHER INFORMATION: Synthetic

<400> SEQUENCE: 100

Ser Asn Ala Ser Gly Thr Thr Thr Met Arg Lys Leu Gly Thr Ile Ser
1               5                   10                  15

Ser Gly Asn Asn Asn Ser Asn Phe Pro Trp Pro Ala Ala Ser Lys Gly
            20                  25                  30

Asp Asp Asn Glu Lys Gln Asp Ser Ser Glu Asn Asp Val Ala Asp Glu
        35                  40                  45

Arg

<210> SEQ ID NO 101
<211> LENGTH: 49
<212> TYPE: PRT
<213> ORGANISM: Artificial Sequence
<220> FEATURE:
<223> OTHER INFORMATION: Synthetic

<400> SEQUENCE: 101

Ser Thr Ala Gly Gly Thr Ala Thr Met Gln Arg Leu Met Thr Thr Asp
1               5                   10                  15

Thr Gly Asn Asn Asn Ser Asn Phe Pro Trp Thr Ala Ala Ser Thr Arg
            20                  25                  30

Asp Asp Asn Glu Arg Gln Gly Gly Glu Gly Gly Asp Ile Glu Asp Asp
        35                  40                  45

Arg

<210> SEQ ID NO 102
<211> LENGTH: 49
<212> TYPE: PRT
<213> ORGANISM: Artificial Sequence
<220> FEATURE:
<223> OTHER INFORMATION: Synthetic

<400> SEQUENCE: 102

Gly Thr Ala Gly Gly Thr Ala Thr Thr Arg Asp Leu Gln Thr Thr Asp
1               5                   10                  15

Asp His Asn Asn Asn Ser Asp Phe Pro Trp Thr Ala Ala Ser Lys Lys
            20                  25                  30

Asp Asp Asn Gly Arg Gln Gly Gly Arg Gly Ala Asn Thr Ala Tyr Glu
        35                  40                  45

Gly

<210> SEQ ID NO 103

```
<211> LENGTH: 49
<212> TYPE: PRT
<213> ORGANISM: Artificial Sequence
<220> FEATURE:
<223> OTHER INFORMATION: Synthetic

<400> SEQUENCE: 103

Gly Thr Thr Gly Gly Thr Ala Ala Met Ser Ala Leu Arg Thr Thr Asp
1               5                   10                  15

Asp Gly Asn Asn Asn Ser Lys Phe Pro Trp Pro Ala Ala Ser Lys Lys
            20                  25                  30

Asp Asp Glu Glu Lys Glu Asp Gly Gly Thr Ser Asn Ala Ala Ile Gly
        35                  40                  45

Asp

<210> SEQ ID NO 104
<211> LENGTH: 49
<212> TYPE: PRT
<213> ORGANISM: Artificial Sequence
<220> FEATURE:
<223> OTHER INFORMATION: Synthetic

<400> SEQUENCE: 104

Gly Asn Thr Ser Gly Thr Thr Thr Asn Arg Glu Leu Met Lys Ile Pro
1               5                   10                  15

Asn Asp Asn Asn Asn Ser Asn Phe Pro Trp Thr Ala Ala Ser Thr Arg
            20                  25                  30

Asp Asp Glu Asp Lys Glu Asp Thr Gly Arg Ala Asp Val Glu Val Gly
        35                  40                  45

Arg

<210> SEQ ID NO 105
<211> LENGTH: 49
<212> TYPE: PRT
<213> ORGANISM: Artificial Sequence
<220> FEATURE:
<223> OTHER INFORMATION: Synthetic

<400> SEQUENCE: 105

Ser Asn Ala Gly Gly Thr Ala Asp Lys Gln Asp Leu Val Thr Ala His
1               5                   10                  15

Ser Glu Asn Asn Asn Ser Asn Phe Pro Trp Thr Ala Ala Ser Lys Glu
            20                  25                  30

Asp Asp Asp Asp Arg Gln Gly Ala Ala Gly Gly Asp Ile Glu Val Gly
        35                  40                  45

Ser

<210> SEQ ID NO 106
<211> LENGTH: 49
<212> TYPE: PRT
<213> ORGANISM: Artificial Sequence
<220> FEATURE:
<223> OTHER INFORMATION: Synthetic

<400> SEQUENCE: 106

Gly Asn Ala Ser Gly Thr Ala Ala Thr His Glu Leu Leu Thr Thr His
1               5                   10                  15

Asp His Asn Asn Asn Ser Asp Phe Pro Trp Thr Ala Ala Ser Lys Arg
            20                  25                  30

Asp Asp Ala Glu Arg Glu Gly Gly Ala Lys Ser Asp Val Asp Phe Gly
        35                  40                  45
```

Ser

<210> SEQ ID NO 107
<211> LENGTH: 49
<212> TYPE: PRT
<213> ORGANISM: Artificial Sequence
<220> FEATURE:
<223> OTHER INFORMATION: Synthetic

<400> SEQUENCE: 107

Ser Asn Ala Ser Gly Thr Ala Asp Thr Arg His Leu Met Thr Thr Pro
1               5                   10                  15

Gly Glu Asn Asn Asn Ser Asp Phe Pro Trp Pro Ala Ala Ser Thr Gly
            20                  25                  30

Asp Asp Thr Gly Lys Gln Gly Ser Ala Thr Thr Asp Ile Glu Tyr Gly
        35                  40                  45

Glu

<210> SEQ ID NO 108
<211> LENGTH: 49
<212> TYPE: PRT
<213> ORGANISM: Artificial Sequence
<220> FEATURE:
<223> OTHER INFORMATION: Synthetic

<400> SEQUENCE: 108

Ser Asn Thr Ser Gly Thr Thr Ala Gln Ser Lys Leu Gln Lys Ile His
1               5                   10                  15

Asn Arg Asn Asn Asn Ser Asp Phe Pro Trp Thr Ala Ala Ser Thr Arg
            20                  25                  30

Asp Asp Asp Asp Arg Gln Gly Ala Glu Gly Ser Asp Val Ala Val Gly
        35                  40                  45

Asp

<210> SEQ ID NO 109
<211> LENGTH: 49
<212> TYPE: PRT
<213> ORGANISM: Artificial Sequence
<220> FEATURE:
<223> OTHER INFORMATION: Synthetic

<400> SEQUENCE: 109

Gly Asn Pro Ser Gly Thr Ala Asp Gln Arg Ala Leu Gln Lys Ile Pro
1               5                   10                  15

Thr Gly Asn Asn Asn Ser Asp Phe Pro Trp Thr Ala Ala Ser Thr Arg
            20                  25                  30

Asp Asp Thr Glu Lys Gln Gly Thr Gly Gly Ser Asp Ile Glu Ile Gly
        35                  40                  45

Gly

<210> SEQ ID NO 110
<211> LENGTH: 49
<212> TYPE: PRT
<213> ORGANISM: Artificial Sequence
<220> FEATURE:
<223> OTHER INFORMATION: Synthetic

<400> SEQUENCE: 110

Ser Asn Ala Ser Gly Thr Ala Gly Leu Asn Ala Leu Lys Lys Ala Tyr
1               5                   10                  15

Thr His Asn Asn Asn Ser Asp Phe Pro Trp Thr Ala Ala Ser Thr Gly
            20                  25                  30

Asp Asp Asp Glu Arg Glu Asn Ala Lys Ala Gly Asn Ala Ala Ile Asp
            35                  40                  45

Gly

<210> SEQ ID NO 111
<211> LENGTH: 49
<212> TYPE: PRT
<213> ORGANISM: Artificial Sequence
<220> FEATURE:
<223> OTHER INFORMATION: Synthetic

<400> SEQUENCE: 111

Gly Asn Pro Ser Gly Thr Thr Asn Leu Gln Arg Leu Met Lys Ile Asp
1               5                   10                  15

Asp Gln Asn Asn Asn Ser Asn Phe Pro Trp Pro Ala Ala Ser Thr Lys
            20                  25                  30

Asp Asp Glu Asp Lys Glu Ser Gly Gly Thr Ala Asp Val Ala Val Asp
            35                  40                  45

Lys

<210> SEQ ID NO 112
<211> LENGTH: 49
<212> TYPE: PRT
<213> ORGANISM: Artificial Sequence
<220> FEATURE:
<223> OTHER INFORMATION: Synthetic

<400> SEQUENCE: 112

Gly Thr Thr Ser Gly Thr Ala Ser Ile Gln Arg Leu Gln Lys Thr Tyr
1               5                   10                  15

Ala Asp Asn Asn Asn Ser Glu Phe Pro Trp Thr Ala Ala Ser Thr Lys
            20                  25                  30

Asp Asp Glu Asp Lys Glu Ser Ala Ala Gly Ser Asp Thr Glu Val Asp
            35                  40                  45

Gly

<210> SEQ ID NO 113
<211> LENGTH: 12
<212> TYPE: PRT
<213> ORGANISM: Artificial Sequence
<220> FEATURE:
<223> OTHER INFORMATION: Synthetic

<400> SEQUENCE: 113

Gln Asn Lys Thr Ser Arg His Pro Asp Glu Ala Gly
1               5                   10

<210> SEQ ID NO 114
<211> LENGTH: 6
<212> TYPE: PRT
<213> ORGANISM: Artificial Sequence
<220> FEATURE:
<223> OTHER INFORMATION: Synthetic

<400> SEQUENCE: 114

Asn Thr Ser Asp Ala Gly
1               5

<210> SEQ ID NO 115
<211> LENGTH: 9

```
<212> TYPE: PRT
<213> ORGANISM: Artificial Sequence
<220> FEATURE:
<223> OTHER INFORMATION: Synthetic

<400> SEQUENCE: 115

Gln His Pro Leu Lys Asn Thr Met Ile
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic

<400> SEQUENCE: 116

Ser Gln His Arg Lys Asn
1               5

<210> SEQ ID NO 117
<211> LENGTH: 12
<212> TYPE: PRT
<213> ORGANISM: Artificial Sequence
<220> FEATURE:
<223> OTHER INFORMATION: Synthetic

<400> SEQUENCE: 117

Arg Lys Asn Thr Ser Gln His Pro Glu Asp Ala Gly
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic

<400> SEQUENCE: 118

Leu Lys Thr Arg Met Gln Pro Glu Ala Gly Val
1               5                   10

<210> SEQ ID NO 119
<211> LENGTH: 4
<212> TYPE: PRT
<213> ORGANISM: Artificial Sequence
<220> FEATURE:
<223> OTHER INFORMATION: Synthetic

<400> SEQUENCE: 119

Thr Ile Ala Val
1

<210> SEQ ID NO 120
<211> LENGTH: 6
<212> TYPE: PRT
<213> ORGANISM: Artificial Sequence
<220> FEATURE:
<223> OTHER INFORMATION: Synthetic

<400> SEQUENCE: 120

Ala Pro His Asp Ser Tyr
1               5

<210> SEQ ID NO 121
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 121

Asp Glu Gly Gln His Arg
1               5

<210> SEQ ID NO 122
<211> LENGTH: 4
<212> TYPE: PRT
<213> ORGANISM: Artificial Sequence
<220> FEATURE:
<223> OTHER INFORMATION: Synthetic

<400> SEQUENCE: 122

Asn Lys Glu Asp
1

<210> SEQ ID NO 123
<211> LENGTH: 4
<212> TYPE: PRT
<213> ORGANISM: Artificial Sequence
<220> FEATURE:
<223> OTHER INFORMATION: Synthetic

<400> SEQUENCE: 123

Lys Arg Glu Gly
1

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Glu Thr Lys Asn Ala Asp
1               5

<210> SEQ ID NO 125
<211> LENGTH: 4
<212> TYPE: PRT
<213> ORGANISM: Artificial Sequence
<220> FEATURE:
<223> OTHER INFORMATION: Synthetic

<400> SEQUENCE: 125

Gly Asn Ser Asp
1

<210> SEQ ID NO 126
<211> LENGTH: 4
<212> TYPE: PRT
<213> ORGANISM: Artificial Sequence
<220> FEATURE:
<223> OTHER INFORMATION: Synthetic

<400> SEQUENCE: 126

Thr Ser Gly Ala
1

<210> SEQ ID NO 127
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 127

Thr Lys Asn Arg Ser Glu Asp Ala Gly
1               5

<210> SEQ ID NO 128
<211> LENGTH: 6
<212> TYPE: PRT
<213> ORGANISM: Artificial Sequence
<220> FEATURE:
<223> OTHER INFORMATION: Synthetic

<400> SEQUENCE: 128

Ala Lys Thr Arg Glu Gly
1               5

<210> SEQ ID NO 129
<211> LENGTH: 6
<212> TYPE: PRT
<213> ORGANISM: Artificial Sequence
<220> FEATURE:
<223> OTHER INFORMATION: Synthetic

<400> SEQUENCE: 129

Ser Asn Thr Asp Ala Gly
1               5

<210> SEQ ID NO 130
<211> LENGTH: 4
<212> TYPE: PRT
<213> ORGANISM: Artificial Sequence
<220> FEATURE:
<223> OTHER INFORMATION: Synthetic

<400> SEQUENCE: 130

Ala Thr Ile Val
1

<210> SEQ ID NO 131
<211> LENGTH: 7
<212> TYPE: PRT
<213> ORGANISM: Artificial Sequence
<220> FEATURE:
<223> OTHER INFORMATION: Synthetic

<400> SEQUENCE: 131

Leu Asn Ile Asp Val Tyr Phe
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic

<400> SEQUENCE: 132

Asn Lys Arg Ser Gln His Glu Asp Gly
1               5

<210> SEQ ID NO 133
<211> LENGTH: 9
<212> TYPE: PRT
<213> ORGANISM: Artificial Sequence
<220> FEATURE:
```

<223> OTHER INFORMATION: Synthetic

<400> SEQUENCE: 133

Ser Lys Asn Thr Arg Glu Asp Ala Gly
1               5

<210> SEQ ID NO 134
<211> LENGTH: 12
<212> TYPE: PRT
<213> ORGANISM: Artificial Sequence
<220> FEATURE:
<223> OTHER INFORMATION: Synthetic

<400> SEQUENCE: 134

Ser Lys Asn Thr Arg Gln His Pro Glu Asp Ala Gly
1               5                   10

<210> SEQ ID NO 135
<211> LENGTH: 6
<212> TYPE: PRT
<213> ORGANISM: Artificial Sequence
<220> FEATURE:
<223> OTHER INFORMATION: Synthetic

<400> SEQUENCE: 135

Asn Gln His Arg Lys Ser
1               5

<210> SEQ ID NO 136
<211> LENGTH: 6
<212> TYPE: PRT
<213> ORGANISM: Artificial Sequence
<220> FEATURE:
<223> OTHER INFORMATION: Synthetic

<400> SEQUENCE: 136

Thr Asn Ser Asp Ala Gly
1               5

<210> SEQ ID NO 137
<211> LENGTH: 12
<212> TYPE: PRT
<213> ORGANISM: Artificial Sequence
<220> FEATURE:
<223> OTHER INFORMATION: Synthetic

<400> SEQUENCE: 137

Ala Lys Asn Thr Arg Ser Gln His Pro Glu Asp Gly
1               5                   10

<210> SEQ ID NO 138
<211> LENGTH: 9
<212> TYPE: PRT
<213> ORGANISM: Artificial Sequence
<220> FEATURE:
<223> OTHER INFORMATION: Synthetic

<400> SEQUENCE: 138

Thr Asn Ile Asp Ala Val Tyr Ser Phe
1               5

<210> SEQ ID NO 139
<211> LENGTH: 12
<212> TYPE: PRT
<213> ORGANISM: Artificial Sequence
<220> FEATURE:
<223> OTHER INFORMATION: Synthetic

```
<400> SEQUENCE: 139

Gly Lys Asn Thr Arg Ser Gln His Pro Glu Asp Ala
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic

<400> SEQUENCE: 140

Thr Lys Asn Arg Ser Met Ile Glu Asp Ala Gly Val
1               5                   10

<210> SEQ ID NO 141
<211> LENGTH: 9
<212> TYPE: PRT
<213> ORGANISM: Artificial Sequence
<220> FEATURE:
<223> OTHER INFORMATION: Synthetic

<400> SEQUENCE: 141

Asn Thr Lys Pro Gln His Ala Glu Asp
1               5

<210> SEQ ID NO 142
<211> LENGTH: 632
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (263)..(264)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (450)..(453)
<223> OTHER INFORMATION: Xaa can be any naturally occurring amino acid
<220> FEATURE:
<221> NAME/KEY: misc_feature
<222> LOCATION: (456)..(460)
<223> OTHER INFORMATION: Xaa can be any naturally occurring amino acid
<220> FEATURE:
<221> NAME/KEY: misc_feature
<222> LOCATION: (462)..(462)
<223> OTHER INFORMATION: Xaa can be any naturally occurring amino acid
<220> FEATURE:
<221> NAME/KEY: misc_feature
<222> LOCATION: (491)..(495)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid
<220> FEATURE:
<221> NAME/KEY: misc_feature
<222> LOCATION: (504)..(504)
<223> OTHER INFORMATION: Xaa can be any naturally occurring amino acid
<220> FEATURE:
<221> NAME/KEY: misc_feature
<222> LOCATION: (508)..(508)
<223> OTHER INFORMATION: Xaa can be any naturally occurring amino acid
<220> FEATURE:
<221> NAME/KEY: misc_feature
<222> LOCATION: (528)..(528)
<223> OTHER INFORMATION: Xaa can be any naturally occurring amino acid
```

```
-continued

<220> FEATURE:
<221> NAME/KEY: misc_feature
<222> LOCATION: (531)..(533)
<223> OTHER INFORMATION: Xaa can be any naturally occurring amino acid
<220> FEATURE:
<221> NAME/KEY: misc_feature
<222> LOCATION: (546)..(546)
<223> OTHER INFORMATION: Xaa is E or Q
<220> FEATURE:
<221> NAME/KEY: misc_feature
<222> LOCATION: (547)..(547)
<223> OTHER INFORMATION: Xaa is G, N, S or D
<220> FEATURE:
<221> NAME/KEY: misc_feature
<222> LOCATION: (548)..(548)
<223> OTHER INFORMATION: Xaa is T, S, G or A
<220> FEATURE:
<221> NAME/KEY: misc_feature
<222> LOCATION: (549)..(549)
<223> OTHER INFORMATION: Xaa is T, K, N, R, S, E, D, A or G
<220> FEATURE:
<221> NAME/KEY: misc_feature
<222> LOCATION: (550)..(550)
<223> OTHER INFORMATION: Xaa is A, K, T, R, E or G
<220> FEATURE:
<221> NAME/KEY: misc_feature
<222> LOCATION: (551)..(551)
<223> OTHER INFORMATION: Xaa is S, N, T, D, A or G
<220> FEATURE:
<221> NAME/KEY: misc_feature
<222> LOCATION: (552)..(552)
<223> OTHER INFORMATION: Xaa is N or D
<220> FEATURE:
<221> NAME/KEY: misc_feature
<222> LOCATION: (553)..(553)
<223> OTHER INFORMATION: Xaa is A, T, I or V
<220> FEATURE:
<221> NAME/KEY: misc_feature
<222> LOCATION: (554)..(554)
<223> OTHER INFORMATION: Xaa is E, A or D
<220> FEATURE:
<221> NAME/KEY: misc_feature
<222> LOCATION: (555)..(555)
<223> OTHER INFORMATION: Xaa is L, N, I, D, V, Y or F
<220> FEATURE:
<221> NAME/KEY: misc_feature
<222> LOCATION: (556)..(556)
<223> OTHER INFORMATION: Xaa is D, E or G
<220> FEATURE:
<221> NAME/KEY: misc_feature
<222> LOCATION: (557)..(557)
<223> OTHER INFORMATION: Xaa is N, K, R, S, Q, H, E, D or G
<220> FEATURE:
<221> NAME/KEY: misc_feature
<222> LOCATION: (558)..(569)
<223> OTHER INFORMATION: Xaa can be any naturally occurring amino acid
<220> FEATURE:
<221> NAME/KEY: misc_feature
<222> LOCATION: (586)..(590)
<223> OTHER INFORMATION: Xaa can be any naturally occurring amino acid
<220> FEATURE:
<221> NAME/KEY: misc_feature
<222> LOCATION: (593)..(595)
<223> OTHER INFORMATION: Xaa can be any naturally occurring amino acid
<220> FEATURE:
<221> NAME/KEY: misc_feature
<222> LOCATION: (597)..(597)
<223> OTHER INFORMATION: Xaa can be any naturally occurring amino acid
<220> FEATURE:
<221> NAME/KEY: misc_feature
<222> LOCATION: (598)..(602)
<223> OTHER INFORMATION: Xaa can be any naturally occurring amino acid
<220> FEATURE:
<221> NAME/KEY: misc_feature
<222> LOCATION: (605)..(607)
<223> OTHER INFORMATION: Xaa can be any naturally occurring amino acid
<220> FEATURE:
<221> NAME/KEY: misc_feature
<222> LOCATION: (609)..(609)
```

<223> OTHER INFORMATION: Xaa can be any naturally occurring amino acid

<400> SEQUENCE: 142

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Xaa Xaa Gly Ala Xaa Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400
```

-continued

```
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
        435                 440                 445
Gln Xaa Xaa Xaa Gly Thr Xaa Xaa Xaa Xaa Leu Xaa Phe Ser
    450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Xaa Xaa Xaa Xaa Asn
                485                 490                 495
Asn Asn Ser Xaa Phe Pro Trp Xaa Ala Ala Ser Xaa Tyr His Leu Asn
            500                 505                 510
Gly Arg Asp Ser Leu Val Asn Pro Gly Pro Ala Met Ala Ser His Xaa
            515                 520                 525
Asp Asp Xaa Xaa Xaa Phe Phe Pro Met His Gly Asn Leu Ile Phe Gly
    530                 535                 540
Lys Xaa Xaa Xaa Xaa Xaa Xaa Xaa Xaa Xaa Xaa Xaa Xaa Xaa Xaa
545                 550                 555                 560
Xaa Xaa Xaa Xaa Xaa Xaa Xaa Xaa Val Met Ile Thr Asp Glu Glu
                565                 570                 575
Glu Ile Arg Thr Thr Asn Pro Val Ala Thr Glu Gln Tyr Gly Thr Val
            580                 585                 590
Ala Asn Asn Leu Gln Xaa Xaa Xaa Xaa Xaa Pro Thr Xaa Xaa Xaa Val
        595                 600                 605
Xaa His Gln Gly Ala Leu Pro Gly Met Val Trp Gln Asp Arg Asp Val
    610                 615                 620
Tyr Leu Gln Gly Pro Ile Trp Ala
625                 630
```

The invention claimed is:

1. A non-naturally occurring nucleic acid molecule comprising:
    (a) a first nucleic acid sequence encoding at least one AAV Rep protein from serotype 3; and
    (b) a second nucleic acid sequence encoding an AAV3B VP1 Cap protein;
    wherein the AAV3B VP1 Cap protein comprises a variant variable region VII (VR-VII) comprising a plurality of amino acid substitutions relative to the wildtype AAV3B VP1 Cap protein VR-VII sequence set forth in amino acids 306-317 of SEQ ID NO: 4, wherein the variant VR-VII comprises:

a first amino acid that corresponds to amino acid 306 of SEQ ID NO: 4 and is E;

a second amino acid that corresponds to amino acid 307 of SEQ ID NO: 4 and is independently selected from the group consisting of N, S and D;

a third amino acid that corresponds to amino acid 308 of SEQ ID NO: 4 and is independently selected from the group consisting of S, G and A;

a fourth amino acid that corresponds to amino acid 309 of SEQ ID NO: 4 and is independently selected from the group consisting of T, K, N, R, S, E, D and A;

a fifth amino acid that corresponds to amino acid 310 of SEQ ID NO: 4 and is independently selected from the group consisting of K, T, R, E and G;

a sixth amino acid that corresponds to amino acid 311 of SEQ ID NO: 4 and is independently selected from the group consisting of N, T, D, A and G;

a seventh amino acid that corresponds to amino acid 312 of SEQ ID NO: 4 and is D;

an eighth amino acid that corresponds to amino acid 313 of SEQ ID NO: 4 and is independently selected from the group consisting of A, T and I;

a ninth amino acid that corresponds to amino acid 314 of SEQ ID NO: 4 and is independently selected from the group consisting of E and A;

a tenth amino acid that corresponds to amino acid 315 of SEQ ID NO: 4 and is independently selected from the group consisting of N, I, D, V, Y and F;

an eleventh amino acid that corresponds to amino acid 316 of SEQ ID NO: 4 and is independently selected from the group consisting of E and G; and a twelfth amino acid that corresponds to amino acid 317 of SEQ ID NO: 4 and is independently selected from the group consisting of K, R, S, Q, H, E, D and G.

2. The non-naturally occurring nucleic acid molecule of claim 1, wherein the nucleic acid molecule further comprises a third nucleic acid sequence encoding at least one molecule providing helper function.

3. The non-naturally occurring nucleic acid molecule of claim 2, wherein the third nucleic acid sequence encoding at least one molecule providing helper function is a polynucleotide from a virus selected from the group consisting of adenovirus and herpesvirus.

4. The non-naturally occurring nucleic acid molecule of claim 1, wherein the second nucleic acid sequence comprises the sequence set forth as:

(SEQ ID NO: 1)
TGCCCACTTACAACAACCATCTCTACAAGCAAATC

TCCAGCVVMDCAGGAGCTASCAACGACAACCACTACTTTGGCTACAGCAC

CCCTTGGGGGTATTTTGACTTTAACAGATTCCACTGCCACTTCTCACCAC

GTGACTGGCAGCGACTCATTAACAACAACTGGGGATTCCGGCCCAAGAAA

CTCAGCTTCAAGCTCTTCAACATCCAAGTTAGAGGGGTCACGCAGAACGA

TGGCACGACGACTATTGCCAATAACCTTACCAGCACGGTTCAAGTGTTTA

CGGACTCGGAGTATCAGCTCCCGTACGTGCTCGGGTCGGCGCACCAAGGC

TGTCTCCCGCCGTTTCCAGCGGACGTCTTCATGGTCCCTCAGTATGGATA

CCTCACCCTGAACAACGGAAGTCAAGCGGTGGGACGCTCATCCTTTTACT

GCCTGGAGTACTTCCCTTCGCAGATGCTAAGGACTGGAAATAACTTCCAA

-continued

TTCAGCTATACCTTCGAGGATGTACCTTTTCACAGCAGCTACGCTCACAG

CCAGAGTTTGGATCGCTTGATGAATCCTCTTATTGATCAGTATCTGTACT

ACCTGAACAGAACGCAARGCAMCVCNRGCGGAACARCCRVCMHSMRSVVS

CTGVNGTTTAGCCAGGCTGGGCCTCAGTCTATGTCTTTGCAGGCCAGAAA

TTGGCTACCTGGGCCCTGCTACCGGCAACAGAGACTTTCAAMARYCBMCR

VCSRSAACAACAACAGTRASTTTCCTTGGMCAGCGGCCAGCAMATATCAT

CTCAATGGCCGCGACTCGCTGGTGAATCCAGGACCAGCTATGGCCAGTCA

CRRGGACGATRMSGRSARATTTTTCCCTATGCACGGCAATCTAATATTTG

GCAAASAARRCRSCRVSRVARVCRATRYCGMSDWCGRSVRSGTAATGATT

ACGGATGAAGAAGAGATTCGTACCACCAATCCTGTGGCAACAGAGCAGTA

TGGAACTGTGGCAAATAACTTGCAGRVSVVSMRSRVCVVSCCCACGDHTV

VSRNSGTCVMSCATCAGGGGGCCTTACCTGGCATGGTGTGGCAAGATCG

T.

* * * * *